(12) United States Patent
Diogenes et al.

(10) Patent No.: US 7,507,716 B2
(45) Date of Patent: Mar. 24, 2009

(54) METHOD FOR TREATING PAIN WITH PROLACTIN ANTAGONISTS

(75) Inventors: Anibal Diogenes, San Antonio, TX (US); Kenneth Hargreaves, San Antonio, TX (US); Armen Akopian, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/482,096

(22) Filed: Jul. 6, 2006

(65) Prior Publication Data

US 2007/0087966 A1  Apr. 19, 2007

Related U.S. Application Data

(60) Provisional application No. 60/696,902, filed on Jul. 6, 2005.

(51) Int. Cl.
*A61K 38/16* (2006.01)
*A61K 38/00* (2006.01)
*C07K 14/435* (2006.01)
*C07K 14/00* (2006.01)

(52) U.S. Cl. .............................. 514/12; 514/2; 530/350
(58) Field of Classification Search ........................ None
See application file for complete search history.

(56) References Cited

U.S. PATENT DOCUMENTS 5,905,083 A * 5/1999 Cincotta et al. ............. 514/288

2001/0036662 A1 11/2001 Walker
2002/0068043 A1 6/2002 Chen et al.
2003/0022833 A1 1/2003 Chen et al.
2004/0127407 A1 7/2004 Chen

OTHER PUBLICATIONS

Wells, J.A. (1990). Addivity of mutational effects in proteins. Biochemistry. 29(37):8509-8517.*
Ngo et al. (1994). Computational complexity, protein structure predicition, and the Levinthal paradox. In Merz and Le Grand (Eds.) The Protein Folding Problem and Tertiary Structure Predicition. Birkhauser:Boston, pp. 491-495.*
Skolnick et al. (2000). From genes to proteins structure and function: novel applications of computational approaches in the genomic era. Trends in Biotechnology. 18:34-39.*

(Continued)

*Primary Examiner*—Christine J Saoud
*Assistant Examiner*—Jon M Lockard
(74) *Attorney, Agent, or Firm*—Meyertons, Hood, Kivlin, Kowert & Goetzel, P.C.; Eric B. Meyertons

(57) ABSTRACT

The embodiments disclosed herein provide methods for inhibiting, reducing and/or treating pain in a subject by administering to a subject in need thereof a pharmaceutical formulation that includes a pharmacologically active compound that is adapted to disrupt PRL signaling in pain neurons. In certain embodiments, the compound is a PRL-R antagonist. In certain embodiments, the compound is adapted to alter the expression of one or more components involved in PRL signaling. Also provided for herein are methods to diagnose a pain disorder in a subject, comprising obtaining a measure of the amount of PRL or PRL mRNA in a biological sample.

10 Claims, 8 Drawing Sheets

OTHER PUBLICATIONS

Goffin et al., "Development and Potential Clinical Uses of Human Prolactin Receptor Antagonists" Endocrine Reviews, 57 pages, Apr. 6, 2006.
Hills, "Healthy Living Newsletter", vol. 2, No. 5, Mar. 16, 2005, 5 pages.
Price et al. "Treatment of trigeminal ganglion neurons in vitro with NGF, GDNF or BDNF: effects on neuronal survival, neurochemical properties and TRPV1-mediated neuropeptide secretion" Jan. 25, 2005, BMC Neuroscience, vol. 6, No. 5, 15 pages.
ABE (1998) "Headache associated with pituitary adenomas" Headache 38: 782-6.
Ahonen (2002) "PRL signal transduction in the epithelial compartment of rat prostate maintained as long-term organ cultures in vitro" Endocrinology 143(1): 228-38.
Amadesi (2004) "Protease-activated receptor 2 sensitizes the capsaicin receptor transient receptor potential vanilloid receptor 1 to induce hyperalgesia" J Neurosci 24: 4300-12.
Amaral (2004) "Participation of prolactin receptors and phosphatidylinositol 3-kinase and MAP kinase pathways in the increase in pancreatic islet mass and sensitivity to glucose during pregnancy" J Endocrinol 183(3): 469-76.
Amaral (2003) "Prolactin-signal transduction in neonatal rat pancreatic islets and interaction with the insulin-signaling pathway" Horm Metab Res 35(5): 282-9.
Asano (2002) "Evaluation of clinical factors affecting knee pain after anterior cruciate ligament reconstruction" The Journal of Knee Surgery 15(1): 23-8.
Bakowska (2003) "The distribution of mRNA for the short form of the prolactin receptor in the forebrain of the female rat" Brain Res Mol Brain Res 116(1-2): 50-8.
Barsky (2001) "Somatic symptom reporting in women and men" Journal of General Internal Medicine 16(4): 266-75.
Ben-Jonathan (2002) "Prolactin as an autocrine-paracrine growth factor in human cancer." Trends Endocrinol Metab 13(6): 245-50.
Bernabei (1998) "Management of pain in elderly patients with cancer. SAGE Study Group. Systematic Assessment of Geriatric Drug Use via Epidemiology" Jama 279(23); 1877-82.
Bernichtein (2001). "S179D-human PRL, a pseudophosphorylated human PRL analog, is an agonist and not an antagonist." Endocrinology 142(9): 3950-53.
Bhatavdekar (2000) "Prolactin as a local growth promoter in patients with locally advanced tongue cancer: GCRI experience" Head Neck 22(3): 257-64.
Binart (2003) "A short form of the prolactin (PRL) receptor is able to rescue mammopoiesis in heterozygous PRL receptor mice" Mol Endocrinol 17(6): 1066-74.
Bole-Feysot (1998) "Prolactin (PRL) and its receptor: actions, signal transduction pathways and phenotypes observed in PRL receptor knockout mice" Endocr Rev 19(3): 225-68.
Bonifacino (1998) "Metabolic labeling with amino acids" Curr. Protocols Mol. Biol Unit 10: 18:10.18.11-10.18.10.
Bonnington (2003) "Signalling pathways involved in the sensitisation of mouse nociceptive neurones by nerve growth factor" J Physiol 551: 433-46.
Borum, M. L. (2002). "Physician perception of IBS management in women and men." Digestive Diseases & Sciences 47(1): 236-7.
Bowsher (1999) "The lifetime occurrence of Herpes zoster and prevalence of post-herpetic neuralgia: A retrospective survey in an elderly population." European Journal of Pain: Ejp 3(4): 335-342.
Brain (1991) "Evidence that calcitonin gene-related peptide contributes to inflammation in the skin and joint" Ann. NY Acad. Sci 112: 412-9.
Brain (1985) "Calcitonin gene-related peptide is a potent vasodilator" Nature 313: 54-56.
Brown (2004) "Effects of cyclic steroid hormone replacement on prolactin and luteinizing hormone surges in female rats" Reproduction 128(3): 373-8.
Bulayeva (2005) "Mechanisms of membrane estrogen receptor-{alpha}-mediated rapid stimulation of Ca2+ levels and prolactin release in a pituitary cell line" Am J Physiol Endocrinol Metab 288(2): E388-97.
Byers (1993) "Effect of sensory denervation on the response of rat molar pulp to exposure injury" J Dent Res 72: 613-8.
Carlsson (1995) "Epidemiology of temporomandibular disorders" Seattle, IASP Press.
Carlton (2001) "Peripheral capsaicin receptors increase in the inflamed rat hindpaw: a possible mechanism for peripheral sensitization." Neuroscience 310: 53-6.
Caterina (1997) "The capsaicin receptor: a heat activated ion channel in the pain pathway" Nature 389: 816-24.
Chakravarti (2005) "Prolactin and heregulin override DNA damage-induced growth arrest and promote phosphatidylinositol-3 kinase-dependent proliferation in breast cancer cells" Int J Oncol 26(2): 509-14.
Chang (2000) "Prolactin-induced cell proliferation in PC12 cells depends on JNK but not ERK activation" J Biol Chem 275(30): 23326-32.
Chiu (2002) "A study on the prevalence of and risk factors for neck pain among university academic staff in Hong Kong" Journal of Occupational Rehabilitation 12(2): 77-91.
Christian (2002) "Rapid actions of 17beta-oestradiol on a subset of lactotrophs in the rat pituitary" J Physiol 539(Pt 2): 557-66.
Chuang (2001) "Bradykinin and nerve growth factor release the capsaicin receptor from PtdIns(4,5)P2-mediated inhibition" Nature 411: 957-62.
Ciereszko (2003) "Prolactin signalling in porcine theca cells: the involvement of protein kinases and phosphatases" Reprod Fertil Dev 15(1-2): 27-35.
Ciereszko (2001) "Luteotrophic action of prolactin during the early luteal phase in pigs: the involvement of protein kinases and phosphatases" Reprod Biol 1(2): 62-83.
Corbacho (2002) "Roles of prolactin and related members of the prolactin/growth hormone/placental lactogen family in angiogenesis" J Endocrinol 173(2): 219-38.
Coss (1999) "Dissociation of Janus kinase 2 and signal transducer and activator of transcription 5 activation after treatment of Nb2 cells with a molecular mimic of phosphorylated prolactin" Endocrinology 140(11): 5087-94.
Davis (2000) "Vanilloid receptor 1 is essential for inflammatory thermal hyperalgesia" Nature 405: 183-7.
Devor (2002) "Pathophysiology of trigeminal neuralgia: the ignition hypothesis" Clin J Pain 18: 4-13.
D'Isanto (2004) "Prolactin modulates IL-8 production induced by porins or LPS through different signaling mechanisms" Immunobiology 209(7): 523-33.
Dogusan (2001). "Cytokine-like effects of prolactin in human mononuclear and polymorphonuclear leukocytes," J Neuroimmunol 120(1-2): 58-66.
Dominguez-Caceres (2004) "Prolactin induces c-Myc expression and cell survival through activation of Src/Akt pathway in lymphoid cells" Oncogene 23(44): 7378-90.
Dorn (2004) "siRNA relives chronic neuropathic pain" Nucleic Acids Res. 32: e49.
Ducret (2002) "Effects of prolactin on intracellular calcium concentration and cell proliferation in human glioma cells" Glia 38(3): 200-14.
Ducret (2004) "Effects of prolactin on ionic membrane conductances in the human malignant astrocytoma cell line U87-MG" J Neurophysiol 91(3): 1203-16.
Dussor (2004) "Cholinergic modulation of nociceptive responses in vivo and neuropeptide release in vitro at the level of the primary sensory neuron" Pain 107(1-2): 22-32.
Feig (1993) "Pairing the cholinergic agonist carbachol with patterned Schaffer collateral stimulation initiates protein synthesis in hippocampal CA1 pyramidal cell dendrites via a muscarinic, NMDA-dependent mechanism" J Neurosci 13 (1010-21).
Flores (1996) "Neuronal nicotinic receptor expression in sensory neurons of the rat trigeminal ganglion: demonstration of alpha3beta4, a novel subtype in the mammalian nervous systems" J Neurosci 16(24): 7892-901.
Flores (2001) "Capsaicin-evocked CGRP release from rat buccal mucosa: development of a model system for studying trigeminal mechanisms of neurogenic inflammation" Eur J Neurosci 14(7): 1113-20.

Franklin (2000) "Protein kinase C alpha, epsilon and AP-1 mediate prolactin regulation of mitochondrial aspartate aminotransferase expression in the rat lateral prostate" Mol Cell Endocrinol 170(1-2): 153-61.

Frasor (2001) "PRL-induced ERalpha gene expression is mediated by Janus kinase 2 (Jak2) while signal transducer and activator of transcription 5b (Stat5b) phosphorylation involves Jak2 and a second tyrosine kinase" Mol Endocrinol 15(11); 1941-52.

Freeman (2000) "Prolactin: structure, function, and regulation of secretion" Physiol Rev 80(4): 1523-631.

Vara (2001) "Src family kinases are required for prolactin induction of cell proliferation" Mol Biol Cell 12(7): 2172-83.

Fristad (1997) "Dental innervation: functions and plasticity after peripheral injury" Acta Odonto Scand 55: 236-54.

Fujimoto (2004). "Identification of estrogen-responsive genes in the GH3 cell line by cDNA microarray analysis" J Steroid Biochem Mol Biol 91(3): 121-9.

Gamse (1985) "Potentiation of tachykinin-induced plasma protein extravasation by CGRP" Eur J Pharmacol 114: 61-66.

Garry (1994) "Sodium Nitroprusside Evokes the Release of Immunoreactive Calcitonin Gene-Related Peptide and Substance P from Dorsal Horn Slices via Nitric Oxide-Dependent and Nitric Odixe-Independent Mechanisms" J. Neuroscience 14: 4329-4337.

Gazelius (1987) "Vasodilatory effects and coexistence of CGRP and substance P in sensory nerves of cat dental pulp" Acta Physiol Scand 130: 33-40.

Gear (1996) "Kappa-opioids produce significantly greater analgesia in women than in men" Nature Med 2(11): 1248-50.

Gerr (2002) "A prospective study of computer users: I. Study design and incidence of musculoskeletal symptoms and disorders" American Journal of Industrial Medicine 41(4): 221-35.

Gibbs (2004) "Neuropeptide Y inhibits capsaicin-sensitive nociceptors via a Y1-receptor-mediated mechanism" Neuroscience 125(3): 703-9.

Goffin (2003) "Development of new prolactin analogs acting as pure prolactin receptor antagonists" Pituitary 6(2): 89-95.

Goodis (2002) "Prostaglandin E2 enhances bradykinin-evoked iCGRP release in bovine dental pulp" J Dent Res 79 (8): 1604-7.

Gordon (1999) "Quantifying analgesic onset in the oral surgery model" Clin Pharm Therap 29: 100.

Goupille (2000) "Effect of PRL on MAPK activation: negative regulatory role of the C-terminal part of the PRL receptor" Mol Cell Endocrinol 159(1-2): 133-46.

Gubbay (2002) "Prolactin induces ERK phosphorylation in epithelial and CD56(+) natural killer cells of the human endometrium" J Clin Endocrinol Metab 87(5): 2329-35.

Gutzman (2004) "Multiple kinase cascades mediate prolactin signals to activating protein-1 in breast cancer cells" Mol Endocrinol 18(12): 3064-75.

Hargreaves (1992) "An In vitro Method to Evaluate Regulation of Neuropeptide Release" J. Endo 18: 597-600.

Heden (1989) "Increased skin flap survival and arterial dilation by calcitonin gene-related peptide" Scand J Plast Reconstr Surg 23: 11-16.

Ho (1993) "Secretion of phosphorylated and non-phosphorylated rat prolactin isoform at different stages of the estrous cycle during rat pregnancy and psuedo-pregnancy" Endocrine J 1: 435-9.

Hovey et al. (2001). "Transcriptional and spatiotemporal regulation of prolactin receptor mRNA and cooperativity with progesterone receptor function during ductal branch growth in the mammary gland." Dev Dyn 222(2): 192-205.

Huang (2002) "Risk factors for diagnostic subgroups of painful temporomandibular disorders (TMD)" Journal of Dental Research 81(4): 284-8.

Igwe (2003) "c-Src kinase activation regulates preprotachykinin gene expression and substance P secretion in rat sensory ganglia" Eur J Neurosci 18: 1719-30.

Ikeda (2001) "Involvement of vanilloid receptor type I and prostanoids in the acid-induced writhing response of mice" Life Sci 69: 2911-9.

Jackson (1999) "Activation of exicatory amino acid receptors in bovine dental pulp evokes the release of iCGRP" J Dent Res 78(1): 54-60.

Jin (2003) "Enhanced gene silencing by the application of multiple specific small interfering RNAs" FEBS Letters 552: 247-52.

Jin (2004) "Modulation of TRPV1 by nonreceptor tyrosine kinase, c-Src kinase" Am J Physiol—Cell Physiol 287: C558-63.

Johansson (2003) "Gender difference in symptoms related to temporomandibular disorders in a population of 50-year-old subjects" Journal of Orofacial Pain 17(1): 29-35.

Kalkam (2003) "Preoperative prediction of severe postoperative pain" Pain 105: 415-423.

Kamei (2001) "Role of vanilloid receptor type I in thermal allodynia and hyperalgesia in diabetic mice" Eur J Pharmacol 422: 83-6.

Kapur (2003) "ral and craniofacial pain: diagnosis, pathophysiology, and treatment" Int Anesth Clin 41: 115-150.

Karadottir (2002) "Pain experienced by patients during periodontal maintenance treatment" Journal of Peridontology 73(5): 536-42.

Katusic (1990) "Incidence and clinical features of trigeminal neuralgia, Rochester, Minnesota, 1945-1984" Annals of Neurology 27(1): 89-95.

Kelly (1999) "Rapid effects of estrogen to modulate G protein-coupled receptors via activation of protein kinase A and protein kinase C pathways" Steriods 64: 64-75.

Kerezoudis (1994) "Involvement of substance P but not nitric oxide or calcitonin gene-related peptide in neurogenic plasma extravasation in rat incisor pulp and lip" Arch Oral Biol 39: 769-74.

Khouzam (2000) "Chronic pain and its management in primary care" South Med J 93: 946-951.

Kilo (1997) "Peripheral CGRP release as a marker for neurogenic inflammation: a model system for the study of neuropeptide secretion in rat paw skin" Pain 73(2): 201-7.

Kinoshita (2001) "Expression of ovarian prolactin receptor in relation to hormonal changes during induction of ovulation in the rat" Gynecol Obstet Invest 52(2): 132-8.

Kitt (2000) "Trigeminal neuralgia: opportunities for research and treatment" Pain 85(1-2): 3-7.

Kjartansson (1987) "Calcitonin gene-related peptide increases survival of a musculocutaneous critical flap in the rat" Eur J Pharmacol 142: 355-8.

Kostova (2001) "Back disorders (low back pain, cervicobrachial and lumbosacral radicular syndromes) and some related risk factors" Journal of the Neurological Sciences 192(1-2): 17-25.

Leondires (2002) "Estradiol stimulates expression of two human prolactin receptor isoform with alternative exons-1 in T47D breast cancer cells" J Steriod Biochem Mol Biol 82(2-3): 263-8.

Leresche (1997) "Use of exogenous hormones and risk of temporomandibular disorder pain" Pain 69(1-2): 153-60.

Lipton (1993) "Estimated prevalence and distribution of reported orofacial pain in the United States" J Am Dent Assoc 124: 115-121.

Livak (2001) "Analysis of relative gene expression data using real-time quantitative PCR and the 2(-Delta Delta C(T)) Method" Methods 25: 402-8.

Ma (2005) "Prolactin-regulated tyrosine hydroxylase activity and messenger ribonucleic acid expression in mediobasal hypothalamic cultures: the differential role of specific protein kinases" Endocrinology 146(1): 93-102.

Marfurt (1993) "Sensory and sympathetic nerve sprouting in rat cornea following neonatal administration of capsaicin" Somatosens Mot Res 10: 377-98.

Martin (2003) "Medical oophorectomy with and without estrogen add-back therapy in the prevention of migraine headache" Headache 43(4): 309-21.

McCleane (1999) "Topical application of doxepin hydrochloride, capsaicin and a combination of both produces analgesia in chronic human neuropathic pain: a randomized double-blind placebo-controlled study" Br J Clin Pharmacol 49: 574-9.

Morenilla-Palao (2004) "Regulated exocytosis contributes to protein kinase C potentiation of vanilloid receptor activity" J Biol Chem 279: 25665-72.

Motta (2004) "Leptin and prolactin modulate the expression of SOCS-1 in association with interleukin-6 and tumor necrosis factor-alpha in mammary cells: a role in differentiated secretory epithelium" Regul Pept 121(1-3): 163-70.

Nagafuchi (1999) "Prolactin locally produced by synovium infiltrating T lymphocytes induces excessive synovial cell functions in patients with rheumatoid arthritis" J Rheumatol 26(9): 1890-900.

Naylor (2003) "Prolactin regulates mammary epithelial cell proliferation via autocrine/paracrine mechanism" Endocrine 20(1-2): 111-4.

Neubert (2002) "Microdialysis in trigeminal ganglia" Brain Res Protoc 10: 102-8.

Norfleet (2000) "Antibodies to the estrogen receptor-alpha modulate rapid prolactin release from rat pituitary tumor cells through plasma membrane estrogen receptors" Faseb J 14(1): 175-65.

Nowak (1999) "Prolactin is an autocrine or paracrine growth factor for human myometrial and leiomyoma cells" Gynecol Obstet Invest 48(2): 127-32.

Numazaki (2003) "Structural determinant of TRPV1 desensitization interacts with calmodulin." Proc. Natl. Acad. Sci. U S A.;100(13):8002-6.

Numazaki (2002) "Direct phosphorylation of capsaicin receptor VR1 by protein kinase Cepsilon and identification of two target serine residues" J Biol Chem 277: 13375-8.

Oetting (1986) "Differential isoform distribution between stores and secreted prolactin" Endocrinology 119: 1377-81.

Ogueta (2002) "Prolactin is a component of the human synovial liquid and modulates the growth and chondrogenic differentiation of bone marrow-derived mesenchymal stem cells" Mol Cell Endocrinol 190(1-2): 51-63.

Oomizu (2003) "Ethanol and estradiol modulate alternative splicing of dopamine D2 receptor messenger RNA and abolish the inhibitory action of bromocriptine on prolactin release from the pituitary gland" Alcohol Clin Exp Res 27(6): 975-80.

Ossipov (1999) "Lack of involvement of capsaicin sensitive neurons in nerve-ligation induced tactile allodynia in rats" Pain 79: 127-33.

Pi (2002). "Sex difference and estrous cycle: expression of prolactin receptor mRNA in rat brain" Brain Res Mol Brain Res 103(1-2): 130-9.

Pi (2003). "Promoter usage and estrogen regulation of prolactin receptor gene in the brain of the female rat." Neuroendocrinology 77(3): 187-97.

Pi (1998) "Differential expression of the two forms of prolactin receptor mRNA within microdissected hypothalamic nuclei of the rat" Brain Res Mol Brain Res 59(1): 1-12.

Picazo (2004) "Cellular localization and changes in expression of prolactin receptor isoforms in sheep ovary throughout the estrous cycle" Reproduction 128(5): 545-53.

Price (2004) "Cannabinoid receptor-independent actions of the aminoalkylindole cannabinoid WIN 55,212-2 on trigeminal sensory neurons" Br J Pharmac 142: 257-66.

Price (2004) "Modulation of trigeminal sensory neuron activity by the dual cannabinoid-vanilloid agonists anandaminde, N-arachidonoyl-dopamine and arachidonyl-2-chloroethylamide" Br J Pharm 141: 1118-1130.

Price (2003) "The neuronal distribution of cannabinoid receptor type 1 in the trigeminal ganglion of the rat" Neuroscience 120(1): 155-62.

Royster (1995) "The prolactin receptor in the fetal rat: cellular localization of mRNA, immunoreactive protein and ligand binding activity and induction of expressin in late gestatin" Endocrinology 136: 3892-3900.

Schroeder (2003) "Inhibition of prolactin (PRL)-induced proliferative signals in breast cancer cells by a molecular mimic of phosphorylated PRL, S179D-PRL" Endocrinology 144(12): 5300-7.

Schuler (2001) "Prolactin receptor heterogeneity: processing and signalling of the long and short isoforms during development" Biochem Soc Trans 29(Pt 2): 52-6.

Secondo (2003) "Involvement of PI3'-K, mitogen-activated protein kinase and protein kinase B in the up-regulation of the expression of nNOSalpha and nNOSbeta splicing variants induced by PRL-receptor activation in GH3 cells" J Neurochem 84(6): 1367-77.

Skinner (2003) "Prolactin release during the estradiol-induced LH surge in ewes: modulation by progesterone but no evidence for prolactin-releasing peptide involvement" J Endocrinol 177(3): 453-60.

Sorin (2000) "Role of protein kinases in the prolactin-induced intracellular calcium rise in Chinese hamster ovary cells expressing the prolactin recpetor" J Neuroendocrinol 12(9): 910-8.

Southhall (2001) "Prostaglandin receptor subtypes, EP3C and EP4, mediate the prostaglandin E2-induced cAMP production and sensitization of sensory neurons" J Biol Chem 276: 16083-91.

Staud (2003) "Diffuse noxious inhibitory control (DNIC) attenuate temporal summation of second pain in normal males but not in normal females or fibromyalgia patients" Pain 101(1-2): 167-74.

Straub (2002) "In polymyalgia rheumatica serum prolactin is positively correlated with the number of typical symptoms but not with typical inflammatory markers" Rheumatology 41: 423-9.

Sweitzer (2004) "Protein kinase C epsilon and gamma: involvement in formalin-induced nociception in neonatal rats" J Pharm Exp Therap 309: 616-25.

Szawaka (2004) "A secondary surge of prolactin on the estrus afternoon" Life Sci 75(8): 911-22.

Takahashi "Molecular cloning and nucleotide sequence of DNA complementary to human decidual prolactin mRNA" J. Biochem. 95 (5), 1491-1499 (1984).

Tanaka (2002) "Identification of a novel first exon of prolactin receptor gene expressed in the rat brain" Endocrinology 143(6): 2080-4.

Torner (2002) "Increased hypothalamic expression of prolactin in lactation: involvement in behavioural and neuroendocrine stress responses" Eur J Neurosci 15(8): 1381-9.

Torner (2001) "Anxiolytic and anti-stress effects of brain prolactin: improved efficacy of antisense targeting of the prolactin receptor by molecular modeling" J Neurosci 21(9): 3207-14.

Tuchsen (2003) "Risk factor predicting hip pain in a 5-year prospective cohort study" Scandinavian Journal of Work, Environment & Health 29(1): 35-9.

Tusher (2001) "Significance analysis of microarrays applied to the ionizing radiation response" Proc Natl Acad Sci U S A 98: 5116-21.

Ulrich-Lai (2001) "Capsaicin-evoked release of immunoreactive caclitonin gene-related peptide from rat trigeminal ganglia: evidence for intraganglionic neurotransmission" Pain 91: 219-26.

Urtishak (2001) "Prolactin and prolactin receptor expression in rat, small intestine, intraepithelial lymphocytes during neonatal development" Dev Immunol 8(3-4): 319-30.

Van Coppenolle Van Coppenolle, F., R. Skryma, et al. (2004). "Prolactin stimulates cell proliferation through a long form of prolactin receptor and K+ channel activation." Biochem J 377 (Pt 3): 569-78.

Walker (2001) "Unmodified and phosphorylated prolactin and gamma delta T cell development and function" Lupus 10(10): 735-41.

Wallaschofski (2003) "Prolactin receptor signaling during platelet activation" Horm Metab Res 35(4): 228-35.

Warren (2001) "Temporomandibular disorders and hormones in women" Cells Tissues Organs 169(3): 187-92.

Watson (1999) "Rapid actions of estrogens in GH3/B6 pituitary tumor cells via a plasma membrane version of estrogen receptor-alpha" Steroids 64(1-2): 5-13.

Watters (2000) "Estrogen modulation of prolactin gene expression requires an intact mitogen-activated protein kinase signal transduction pathway in cultured rat pituitary cells" Mol Endocrinol 14(11): 1872-81.

Wicks (1995) "Biological activity of phosphorylated and dephosphorylated bovine prolactin" Mol Cell Endocrinol 112: 223-9.

Wu (2003) "Differnt biological effects of unmodified prolactin and a molecular mimic of phosphorylated prolactin involve different signaling pathways" Biochemistry 42(24): 7561-70.

Xu (2003) "Opposite effects of unmodified prolactin and a molecular mimic of phosphorylated prolactin on morphology and the expression of prostate specific genes in the norma rat prostate" Prostate 54(1): 25-33.

Yamamoto Yamamoto, I., M. Wakita, et al. (2003) "Tissue distribution of prolactin receptor mRNA during late stage embryogenesis of the chick." Poult Sci 82(1): 155-7.

Yamauchi (2000) "Constitutive tyrosine phosphorylation of ErbB-2 via Jak2 by autocrine secretion of prolactin in human breast cancer" J Biol Chem 275(43): 33937-44.

Yunus (2002) "Gender differences in fibromyalgia and other related syndromes" Journal of Gender Specific Medicine 5(2): 42-7.

Zakrzewska (2002) "Facial pain: neurological and non-neurological." J Neurol Neurosurg Psych 72(Suppl 2): ii27-ii32.

Zakrzewska (2002). "Trigeminal neuralgia." Clinical Evidence 7: 1221-31.

Zakrzewska (1996) "Women as dental patients: are there any gender differences?" International Dental Journal 46 (6): 548-57.

Zhang (2002) "Acute topical application of tumor necrosis factor alpha evokes protein kinase A-dependent responses in rat sensory neurons" J Neurophysiol 88: 1387-92.

Zhuang (2004) "Phosphatidylinositol 3-kinase activates ERK in primary sensory neurons and mediates inflammatory heat hyperalgesia throught TRPV1 sensitization" J Neurosci 24: 8300-09.

* cited by examiner

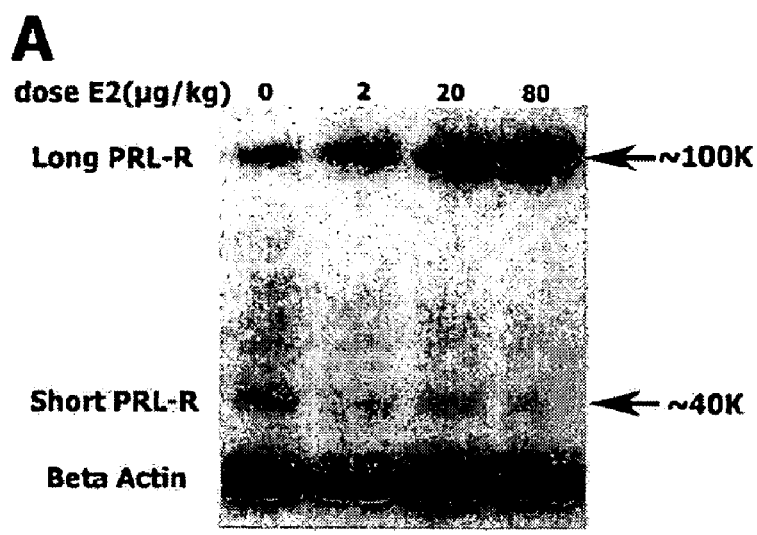
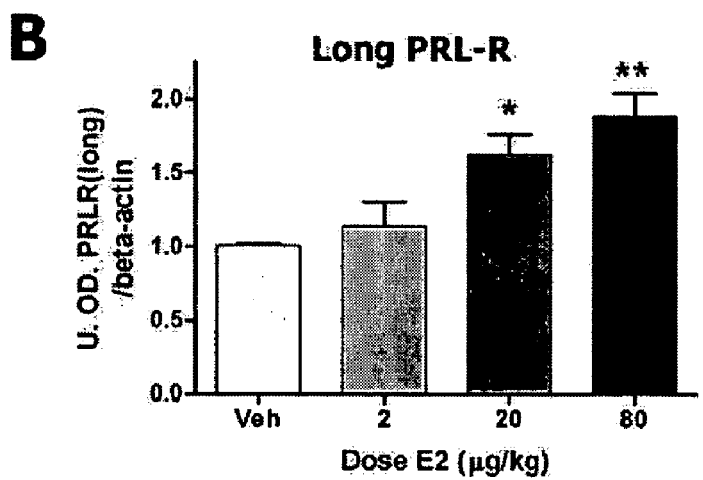
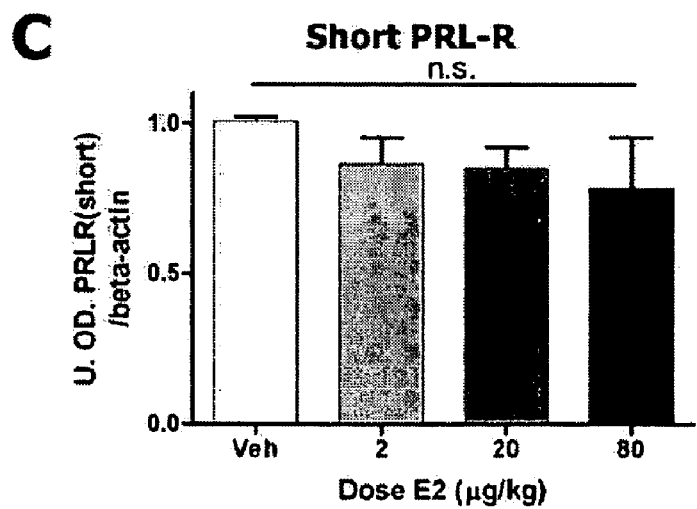
FIG. 3

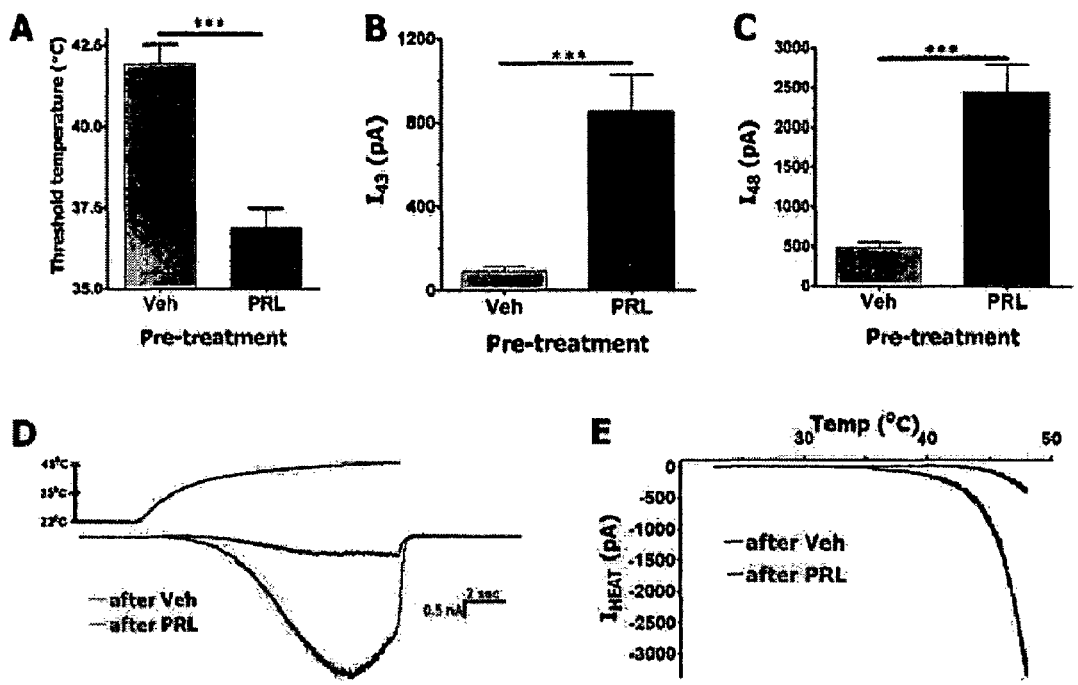
FIG. 6
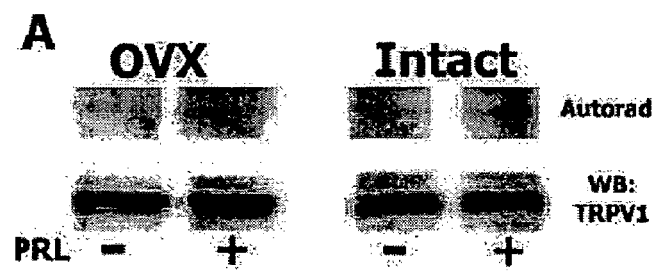
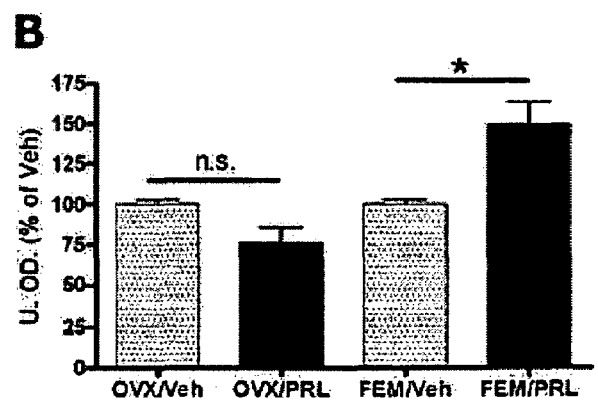
FIG. 7

```
1    mnikgspwkg  slllllvsnl  llcqsvapLP  ICPGGAARCQ  VTLRDLFDRA
51   VVLSHYIHNL  SSEMFSEFDK  RYTHGRGFIT  KAINSCHTSS  LATPEDKEQA
101  QQMNQKDFLS  LIVSILRSWN  EPLYHLVTEV  RGMQEAPEAI  LSKAVEIEEQ
151  TKRLLEGMEL  IVSQVHPETK  ENEIYPVWSG  LPSLQMADEE  SRLSAYYNLL
201  HCLRRDSHKI  DNYLKLLKCR  IIHNNNC
``` hPRL (SEQ ID NO: 47)
(Prior Art)

FIG. 9A

```
1    LPICPGGAAR  CQVTLRDLFD  RAVVLSHYIH  NLSSEMFSEF  DKRYTHGRGF
51   ITKAINSCHT  SSLATPEDKE  QAQQMNQKDF  LSLIVSILRS  WNEPLYHLVT
101  EVRGMQEAPE  AILSKAVEIE  EQTKRLLERM  ELIVSQVHPE  TKENEIYPVW
151  SGLPSLQMAD  EESRLSAYYN  LLHCLRRDSH  KIDNYLKLLK  CRIIHNNNC
```

G129R-hPRL (SEQ ID NO: 48)
(Prior Art)

FIG. 9B

SEQUENCE LISTING

<160> NUMBER OF SEQ IDS NOS: 48

<210> SEQ ID NO 1
<211> LENGTH: 21
<212> TYPE: RNA
<213> ORGANISM: Homo sapiens

<400> SEQUENCE: 1
gggcuuucug ccuuacucac u                                              21

<210> SEQ ID NO 2
<211> LENGTH: 21
<212> TYPE: RNA
<213> ORGANISM: Homo sapiens

<400> SEQUENCE: 2
ggacuuccua ccaauuauuc a                                              21

<210> SEQ ID NO 3
<211> LENGTH: 21
<212> TYPE: RNA
<213> ORGANISM: Homo sapiens

<400> SEQUENCE: 3
ggacgugacu uacauaguuc a                                              21

<210> SEQ ID NO 4
<211> LENGTH: 21
<212> TYPE: RNA
<213> ORGANISM: Homo sapiens

<400> SEQUENCE: 4
ggagcuggcu guggaaguaa a                                              21

<210> SEQ ID NO 5
<211> LENGTH: 21
<212> TYPE: RNA
<213> ORGANISM: Homo sapiens

<400> SEQUENCE: 5
gccuacaucc aggacagaaa u                                              21

<210> SEQ ID NO 6
<211> LENGTH: 21
<212> TYPE: RNA
<213> ORGANISM: Homo sapiens

<400> SEQUENCE: 6
guucgcugca aaccagacca u                                              21

<210> SEQ ID NO 7
<211> LENGTH: 21
<212> TYPE: RNA
<213> ORGANISM: Homo sapiens

<400> SEQUENCE: 7
gcaaaccaga ccauggauac u                                              21

<210> SEQ ID NO 8
<211> LENGTH: 21
<212> TYPE: RNA
<213> ORGANISM: Homo sapiens

```
<400> SEQUENCE: 8
guccagcgac cuucauucag a                                              21

<210> SEQ ID NO 9
<211> LENGTH: 21
<212> TYPE: RNA
<213> ORGANISM: Homo sapiens

<400> SEQUENCE: 9
gcgaccuuca uucagauacc u                                              21

<210> SEQ ID NO 10
<211> LENGTH: 21
<212> TYPE: RNA
<213> ORGANISM: Homo sapiens

<400> SEQUENCE: 10
ggcuguccuu ucugcuguca u                                              21

<210> SEQ ID NO 11
<211> LENGTH: 21
<212> TYPE: RNA
<213> ORGANISM: Homo sapiens

<400> SEQUENCE: 11
guccuuucug cugucaucug u                                              21

<210> SEQ ID NO 12
<211> LENGTH: 21
<212> TYPE: RNA
<213> ORGANISM: Homo sapiens

<400> SEQUENCE: 12
guuggagaag ggcaagucug a                                              21

<210> SEQ ID NO 13
<211> LENGTH: 21
<212> TYPE: RNA
<213> ORGANISM: Homo sapiens

<400> SEQUENCE: 13
gaagggcaag ucugaagaac u                                              21

<210> SEQ ID NO 14
<211> LENGTH: 21
<212> TYPE: RNA
<213> ORGANISM: Homo sapiens

<400> SEQUENCE: 14
gggcaagucu gaagaacuac u                                              21

<210> SEQ ID NO 15
<211> LENGTH: 21
<212> TYPE: RNA
<213> ORGANISM: Homo sapiens

<400> SEQUENCE: 15
gcaagucuga agaacuacug a                                              21

<210> SEQ ID NO 16
<211> LENGTH: 21
<212> TYPE: RNA
```

<213> ORGANISM: Homo sapiens

<400> SEQUENCE: 16
gguggaguau uuagaaguag a        21

<210> SEQ ID NO 17
<211> LENGTH: 21
<212> TYPE: RNA
<213> ORGANISM: Homo sapiens

<400> SEQUENCE: 17
guggaguauu uagaaguaga u        21

<210> SEQ ID NO 18
<211> LENGTH: 21
<212> TYPE: RNA
<213> ORGANISM: Homo sapiens

<400> SEQUENCE: 18
ggaguauuua gaaguagaug a        21

<210> SEQ ID NO 19
<211> LENGTH: 21
<212> TYPE: RNA
<213> ORGANISM: Homo sapiens

<400> SEQUENCE: 19
ggaccagcau cuaaugucag u        21

<210> SEQ ID NO 20
<211> LENGTH: 21
<212> TYPE: RNA
<213> ORGANISM: Homo sapiens

<400> SEQUENCE: 20
ggccaauccc uccacauucu a        21

<210> SEQ ID NO 21
<211> LENGTH: 21
<212> TYPE: RNA
<213> ORGANISM: Homo sapiens

<400> SEQUENCE: 21
ggucauugag aagccagaga a        21

<210> SEQ ID NO 22
<211> LENGTH: 21
<212> TYPE: RNA
<213> ORGANISM: Homo sapiens

<400> SEQUENCE: 22
gauccucuua ccacaauauu a        21

<210> SEQ ID NO 23
<211> LENGTH: 21
<212> TYPE: RNA
<213> ORGANISM: Homo sapiens

<400> SEQUENCE: 23
ggagauucac aaggucaaca a        21

<210> SEQ ID NO 24
<211> LENGTH: 21

```
<212> TYPE: RNA
<213> ORGANISM: Homo sapiens

<400> SEQUENCE: 24
ggugcauuau cauugcuacc a                                              21

<210> SEQ ID NO 25
<211> LENGTH: 21
<212> TYPE: RNA
<213> ORGANISM: Homo sapiens

<400> SEQUENCE: 25
gugccagauc cacaugcuaa a                                              21

<210> SEQ ID NO 26
<211> LENGTH: 21
<212> TYPE: RNA
<213> ORGANISM: Homo sapiens

<400> SEQUENCE: 26
gccaacuuca cugcaacauc a                                              21

<210> SEQ ID NO 27
<211> LENGTH: 21
<212> TYPE: RNA
<213> ORGANISM: Homo sapiens

<400> SEQUENCE: 27
guacgugaaa ugcucaagaa u                                              21

<210> SEQ ID NO 28
<211> LENGTH: 21
<212> TYPE: RNA
<213> ORGANISM: Homo sapiens

<400> SEQUENCE: 28
gcagcugauu ccagaacaaa u                                              21

<210> SEQ ID NO 29
<211> LENGTH: 21
<212> TYPE: RNA
<213> ORGANISM: Homo sapiens

<400> SEQUENCE: 29
gagggacaau gccaauaggu a                                              21

<210> SEQ ID NO 30
<211> LENGTH: 21
<212> TYPE: RNA
<213> ORGANISM: Homo sapiens

<400> SEQUENCE: 30
gggacaaugc caauagguau a                                              21

<210> SEQ ID NO 31
<211> LENGTH: 21
<212> TYPE: RNA
<213> ORGANISM: Homo sapiens

<400> SEQUENCE: 31
gggacagacg gaaaugaaau u                                              21

<210> SEQ ID NO 32
```

-continued

<211> LENGTH: 21
<212> TYPE: RNA
<213> ORGANISM: Homo sapiens

<400> SEQUENCE: 32
ggaagaaacu ugauaacuga u                                              21

<210> SEQ ID NO 33
<211> LENGTH: 21
<212> TYPE: RNA
<213> ORGANISM: Homo sapiens

<400> SEQUENCE: 33
gauccuccaa accaaucuag u                                              21

<210> SEQ ID NO 34
<211> LENGTH: 21
<212> TYPE: RNA
<213> ORGANISM: Homo sapiens

<400> SEQUENCE: 34
gccaguaugu cuuccugaau a                                              21

<210> SEQ ID NO 35
<211> LENGTH: 21
<212> TYPE: RNA
<213> ORGANISM: Homo sapiens

<400> SEQUENCE: 35
gccaauaucu gggaaagaga a                                              21

<210> SEQ ID NO 36
<211> LENGTH: 21
<212> TYPE: RNA
<213> ORGANISM: Homo sapiens

<400> SEQUENCE: 36
gucccacuac auccauaacc u                                              21

<210> SEQ ID NO 37
<211> LENGTH: 21
<212> TYPE: RNA
<213> ORGANISM: Homo sapiens

<400> SEQUENCE: 37
gcaagcccaa cagaugaauc a                                              21

<210> SEQ ID NO 38
<211> LENGTH: 21
<212> TYPE: RNA
<213> ORGANISM: Homo sapiens

<400> SEQUENCE: 38
gaagccucuu ccuggaaugg u                                              21

<210> SEQ ID NO 39
<211> LENGTH: 21
<212> TYPE: RNA
<213> ORGANISM: Homo sapiens

<400> SEQUENCE: 39
gcaaaccaaa cggcuucuag a                                              21

<210> SEQ ID NO 40
<211> LENGTH: 21
<212> TYPE: RNA
<213> ORGANISM: Homo sapiens

<400> SEQUENCE: 40
gucucgccuu ucugcuuauu a                                              21

<210> SEQ ID NO 41
<211> LENGTH: 21
<212> TYPE: RNA
<213> ORGANISM: Homo sapiens

<400> SEQUENCE: 41
gcuccugaag ugccgaauca u                                              21

<210> SEQ ID NO 42
<211> LENGTH: 21
<212> TYPE: RNA
<213> ORGANISM: Homo sapiens

<400> SEQUENCE: 42
gugccgaauc auccacaaca a                                              21

<210> SEQ ID NO 43
<211> LENGTH: 21
<212> TYPE: RNA
<213> ORGANISM: Homo sapiens

<400> SEQUENCE: 43
gccgaaucau ccacaacaac a                                              21

<210> SEQ ID NO 44
<211> LENGTH: 21
<212> TYPE: RNA
<213> ORGANISM: Homo sapiens

<400> SEQUENCE: 44
gcuaagccca cauccauuuc a                                              21

<210> SEQ ID NO 45
<211> LENGTH: 21
<212> TYPE: RNA
<213> ORGANISM: Homo sapiens

<400> SEQUENCE: 45
gcccacaucc auuucaucua u                                              21

<210> SEQ ID NO 46
<211> LENGTH: 21
<212> TYPE: RNA
<213> ORGANISM: Homo sapiens

<400> SEQUENCE: 46
gguguaacag gucuccucuu a                                              21

<210> SEQ ID NO 47
<211> LENGTH: 227
<212> TYPE: PRT
<213> ORGANISM: Homo sapiens

<400> SEQUENCE: 47

Met Asn Ile Lys Gly Ser Pro Trp Lys Gly Ser Leu Leu Leu Leu
1               5                   10                  15

Val Ser Asn Leu Leu Leu Cys Gln Ser Val Ala Pro Leu Pro Ile Cys
            20                  25                  30

Pro Gly Gly Ala Ala Arg Cys Gln Val Thr Leu Arg Asp Leu Phe Asp
            35                  40                  45

Arg Ala Val Val Leu Ser His Tyr Ile His Asn Leu Ser Ser Glu Met
            50                  55                  60

Phe Ser Glu Phe Asp Lys Arg Tyr Thr His Gly Arg Gly Phe Ile Thr
65                  70                  75                  80

Lys Ala Ile Asn Ser Cys His Thr Ser Ser Leu Ala Thr Pro Glu Asp
            85                  90                  95

Lys Glu Gln Ala Gln Gln Met Asn Gln Lys Asp Phe Leu Ser Leu Ile
            100                 105                 110

Val Ser Ile Leu Arg Ser Trp Asn Glu Pro Leu Tyr His Leu Val Thr
            115                 120                 125

Glu Val Arg Gly Met Gln Glu Ala Pro Glu Ala Ile Leu Ser Lys Ala
            130                 135                 140

Val Glu Ile Glu Glu Gln Thr Lys Arg Leu Leu Glu Gly Met Glu Leu
145                 150                 155                 160

Ile Val Ser Gln Val His Pro Glu Thr Lys Glu Asn Glu Ile Tyr Pro
            165                 170                 175

Val Trp Ser Gly Leu Pro Ser Leu Gln Met Ala Asp Glu Glu Ser Arg
            180                 185                 190

Leu Ser Ala Tyr Tyr Asn Leu Leu His Cys Leu Arg Arg Asp Ser His
            195                 200                 205

Lys Ile Asp Asn Tyr Leu Lys Leu Leu Lys Cys Arg Ile Ile His Asn
            210                 215                 220

Asn Asn Cys
225

<210> SEQ ID NO 48
<211> LENGTH: 199
<212> TYPE: PRT
<213> ORGANISM: Homo sapiens

<400> SEQUENCE: 48

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
            35                  40                  45

Gly Phe Ile Thr Lys Ala Ile Asn Ser Cys His Thr Ser Ser Leu Ala
            50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
            85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
            115                 120                 125

Arg Met Glu Leu Ile Val Ser Gln Val His Pro Glu Thr Lys Glu Asn
            130                 135                 140

Glu Ile Tyr Pro Val Trp Ser Gly Leu Pro Ser Leu Gln Met Ala Asp

```
                145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
                180                 185                 190

Ile Ile His Asn Asn Asn Cys
            195
```

METHOD FOR TREATING PAIN WITH PROLACTIN ANTAGONISTS

CROSS-REFERENCE TO RELATED APPLICATIONS

The present application claims the right of priority under 35 U.S.C. §119 to U.S. Provisional Application No. 60/696,902 by Diogenes et al. filed Jul. 6, 2005, which is incorporated by reference in its entirety as though fully set forth herein.

REFERENCE TO GOVERNMENT SPONSORED RESEARCH

This invention was at least partially supported through a grant or award from the National Institute of Health. The U.S. Government, therefore, may have certain rights to this invention.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

BACKGROUND OF THE INVENTION

1. Field of the Invention

The present invention generally relates to the field of therapeutics. Specifically, the present invention relates to therapeutic compositions comprising inhibitors of prolactin or prolactin receptor function, said therapeutic compositions being suitable for use in treating pain. The present invention further relates to methods for the manufacture and use of said therapeutic compositions. The present invention relates yet further to methods for assessing the severity of pain and/or diagnosing pain disorders in subjects by determining the amount of prolactin present in a biological sample.

2. Description of the Related Art

Trigeminal pain represents a major category of pain disorders and is reported frequently in pain patients, particularly given its comparatively low representation of the total body surface area. (Martin 1986; Khouzam 2000; Welch 2001). From a public health perspective, diagnosis and treatment of trigeminal pain disorders represent a major clinical challenge. Some disorders are relatively rare but are characterized as extremely intense devastating episodes of pain (e.g., trigeminal neuralgia (TN) (Zakrzewska 1996; Devor, Amir et al. 2002; Zakrzewska 2002; Zakrzewska 2002; Kapur, Kamel et al. 2003), others disorders are more common and can be acute-to-chronic periods of persistent aching pain (e.g., temporomandibular disorders, TMD, (Lipton, Ship et al. 1993; Carlsson and LeResche 1995; LeResche, Saunders et al. 1997), Yet other conditions are relatively common occurrences of moderate-to-severe pain due to orofacial infection and inflammation (e.g., odontogenic pain). Many other pain disorders also occur in other body regions and include pain from fibromyalgia, cancer, arthritis, surgery, and other disorders or conditions.

Numerous studies have demonstrated that women are at increased risk for many pain disorders. Moreover, several of these conditions are exacerbated during the menstrual cycle or during episodes of altered circulating levels of estrogens or other steroids (Somerville, 1975; LeResche, 1997; Isselee et al., 2001; Isselee et al., 2002). Although gender bias is clearly evident for TMD (LeResche, Saunders et al. 1997; Warren and Fried 2001; Huang, LeResche et al. 2002; Johansson, Unell et al. 2003) and trigeminal neuralgia (Katusic, Beard et al. 1990; Kitt, Gruber et al. 2000), other studies have indicated that women are at increased risk for pain after oral surgery, (Gear, Miaskowski et al. 1996; Gordon, Brahim et al. 1999) periodontal treatment (Karadottir, Lenoir et al. 2002), knee surgery (Asano, Muneta et al. 2002), other surgical procedures, (Kalkam, Visser et al. 2003) musculoskeletal pain in the neck (Chiu, Ku et al. 2002), hips (Tuchsen, Hannerz et al. 2003), hands (Gerr, Marcus et al. 2002), and elsewhere (Barsky, Peekna et al. 2001; Kostova and Koleva 2001), and disorders including fibromyalgia (Yunus 2002; Staud, Robinson et al. 2003), post-herpetic neuralgia (Bowsher 1999), migraine (Martin, Wernke et al. 2003), irritable bowel syndrome (Borum 2002),. and cancer pain (Bernabei, Gambassi et al. 1998). Thus, studies from multiple pain disorders indicate that patient gender may, at least in part, be a risk factor for numerous acute and chronic pain conditions. While the mechanisms for these gender differences in pain responsiveness are numerous, complex and are far from being understood, many studies have identified the important role played by sex hormones, and in particular estrogen, on pain responses.

Relationship Between Estrogen and Prolactin

PRL was originally discovered as a protein hormone, derived from pituitary lactotrophs, that acted to regulate lactation. However, considerable research has now identified several post-translationally modified forms of PRL that vary based on size, phosphorylation or glycosylation (Freeman, Kanyicska et al. 2000; Walker 2001). In the rat, ~90-95% of pituitary PRL is either the unmodified or phosphorylated PRL, and the unmodified form constitutes about 60-75% of total PRL (Oetting and Walker 1986; Ho, Kawaminami et al. 1993; Walker 2001). In general, the unmodified PRL acts as an agonist, while the form PRL that is phosphorylated on S179 acts as a partial agonist or full antagonist (Walker 2001; Goffin, Bernichtein et al. 2003; Wu, Coss et al. 2003; Xu, Wu et al. 2003) in many situations, depending on the experimental systems being tested (Bernichtein, Kinet et al. 2001). This difference appears to be due to agonist-directed signaling of the same PRL receptor (Coss, Kuo et al. 1999). Equally important, many non-pituitary cells express PRL including the CNS, immune cells, endothelium, kidney and uterus. In many of these tissues, PRL is thought to play a major autocrine/paracrine function since both PRL and the prolactin receptor (PRL-R) are expressed in the same cell/tissue. Evidence supporting the hypothesis that PRL exerts a local autocrine/paracrine function has been gathered for the mammary gland, endothelium, lymphocytes, knee joints and several types of cancers (Nagafuchi, Suzuki et al. 1999; Nowak, Mora et al. 1999; Bhatavdekar, Patel et al. 2000; Urtishak, McKenna et al. 2001; Ben-Jonathan, Liby et al. 2002; Corbacho, Martinez De La Escalera et al. 2002; Ogueta, Munoz et al. 2002; Goffin, Bernichtein et al. 2003; Naylor, Lockefeer et al. 2003).

Both in vivo and in vitro studies indicate that application of estrogen or cyclic increases in endogenous estradiol leads to a rapid, non-genomic release of PRL via activation of calcium channels (Christian and Morris 2002; Brown, Janik et al. 2004; Szawka and Anselmo-Franci 2004; Bulayeva, Wozniak et al. 2005). Indeed, an estradiol-induced PRL surge accompanies the proestrous LH surge in several species (Skinner and Caraty 2003). The rapid effect of estradiol on PRL release is believed to be mediated by estrogen receptors (ER) located on the plasma membrane since the estradiol effect is blocked by application of an antibody (presumably restricted to the extracellular space) that is directed against a hinge element of the ER (Watson, Norfleet et al. 1999; Norfleet, Clarke et al. 2000).

While acute estradiol exposure rapidly evokes PRL release, a more prolonged exposure increases PRL expression (i.e. transcription). This effect of estradiol on PRL expression has been demonstrated in several cell types (Watters, Chun et al. 2000; Oomizu, Boyadjieva et al. 2003; Fujimoto, Igarashi et al. 2004). In rat pituitary cultures, the estradiol-induced upregulation of PRL mRNA is mediated by the MAP kinase signaling pathway since PRL upregulation is blocked by pretreatment with the MAPK kinase inhibitors PD98059 and UO126 (Watters, Chun et al. 2000).

Prolactin Receptors and Associated Signaling Pathways

The PRL receptor (PRL-R) belongs to the class I cytokine receptor super-family. The PRL-R is transcribed from a single gene of the genome. Alternative splicing of the PRL-R gene generates a long form (L-PRL-R) and at least three short forms (S1-, S2- and S3-PRL-R) (Hovey, Trott et al. 2001). The expression of these forms of the PRL-R is tissue specific (Hovey, Trott et al. 2001; Kinoshita, Yasui et al. 2001; Yamamoto, Wakita et al. 2003) and differential expression is observed in different brain regions (Pi and Grattan 1998; Bakowska and Morrell 2003). The 5'-untranslated region of PRL-R mRNA also contains at least four alternative first exons (1A, B, C; aka E1(1), E1(2), E1(3) and E1(4)) that are expressed in a tissue-specific fashion (Tanaka, Hayashida et al. 2002). In addition, estradiol upregulates PRL-R transcripts (Leondires, Hu et al. 2002) and studies evaluating estradiol upregulation of PRL-R in rat brain report an increase in transcripts containing exons 1A and 1C (Pi, Zhang et al. 2003). Further, the relative expression of the long and short forms of PRL-R is altered over the estrous cycle in sheep ovaries (Picazo, Garcia Ruiz et al. 2004) and female rat brain (Pi and Voogt 2002). One study has reported the expression of PRL-R in fetal trigeminal and dorsal root ganglia (Royster, Driscoll et al. 1995).

PRL receptors regulate a variety of intracellular signaling cascades that differ depending upon the cell type examined. The best-studied signaling systems are mediated through tyrosine kinase pathways. In a prostate carcinoma cell line, application of PRL leads to rapid tyrosine kinase signaling that is blocked by the tyrosine kinase inhibitors genistein, herbimycin A and lavandustine A (Van Coppenolle, Skryma et al. 2004). In the MCF-7 breast tumor cell line, activation of PRL-R leads to signaling primarily via Janus kinase/signal transducer and activator of transcription 5 (JAK/STAT5) and ERK1/2, although signaling via c-Src, phosphatidylinositol 3'-kinase, (phospholipase C-gamma PLCγ), protein kinase C, and other MAPKs were shown to contribute to maximal signaling (Dogusan, Hooghe et al. 2001; Fresno Vara, Caceres et al. 2001; Ahonen, Harkonen et al. 2002; Gutzman, Rugowski et al. 2004). Some studies on cell lines have shown that application of PRL stimulates $Ca^{2+}$ entry and intracellular $Ca^{2+}$ mobilization via a tyrosine kinase-dependent mechanism (Sorin, Vacher et al. 2000; Ducret, Boudina et al. 2002). Studies in other cell lines have confirmed activation of many of these kinases although the relative importance of various signaling pathways activated by PRL-R are dependent upon the cell type examined or the measure employed (Cheng, Zhizhin et al. 2000; Goupille, Barnier et al. 2000; Gubbay, Critchley et al. 2002; Amaral, Ueno et al. 2003; Amaral, Cunha et al. 2004; D'Isanto, Vitiello et al. 2004; Dominguez-Caceres, Garcia-Martinez et al. 2004). Fewer studies have evaluated whether the different forms of PRL-R activate different signaling pathways (Binart, Imbert-Bollore et al. 2003). It was demonstrated that the long form of the PRL-R can signal via all known PRL evoked pathways, whereas the short forms of PRL-R, which have a truncated cytoplasmic domain, have a much more restricted signaling repertoire that includes PKC and PLCγ (Schuler, Lu et al. 2001; Wallaschofski, Kobsar et al. 2003).

Transient Receptor Potential Vanniloid Type-1 (TRPV1) in Pain

The subclass of nociceptors expressing the capsaicin receptor (i.e., TRPV1 aka VR1) plays a key role in the development of pain. Animals with genetic deletion of the VR1 gene display reduced responses to thermal inflammatory hyperalgesia or to certain chemical stimuli (Caterina, Schumacher et al. 1997; Davis, Gray et al. 2000). In addition, capsaicin desensitization procedures significantly reduced behavioral responses to inflammatory injury in rats or neuropathic pain in humans (McCleane 1999; Ikeda, Ueno et al. 2001). Other studies have also lent support to the hypothesis that the TRPV1-positive subclass of nociceptors contributes to the development of inflammatory pain (Carlton and Coggeshall 2001; Chuang, Prescott et al. 2001; Kamei, Zushida et al. 2001). Further, the TRPV1-positive subclass of nociceptors mediates thermal hyperalgesia and dynamic (i.e., stroking with cotton wisp) but not static (i.e., von Frey filaments) mechanical allodynia in neuropathic pain (Ossipov, Bian et al. 1999; Chuang, Prescott et al. 2001). Collectively, these studies indicate that the TRPV1-expressing class of nociceptors is a major sensory system for transduction of noxious peripheral stimuli.

SUMMARY OF THE INVENTION

In a first set of embodiments, methods for inhibiting, reducing and/or treating pain in a subject may include administering to a subject who would benefit from such treatment an effective amount of a pharmaceutically acceptable formulation comprising a composition that at least partially inhibits the biological activity of prolactin (PRL) and/or prolactin receptor (PRL-R). In some embodiments, the formulation may include a full and/or a partial prolactin antagonist. In some embodiments, prolactin antagonists suitable for use in treating pain may include one or more variants and/or isoforms of PRL in which the amino acid sequence of PRL may be altered at one or more positions relative to wild-type PRL. In some embodiments, a formulation suitable for use in treating pain may include may include a polynucleotide molecule that is capable of affecting (i.e., increasing or decreasing) the expression of at least one component of PRL signaling in sensory neurons.

In another set of embodiments, methods for inhibiting, reducing and/or treating pain in a subject may include administering to a who would benefit from such treatment an effective amount of a pharmaceutically acceptable formulation comprising a pharmacologically active composition, wherein the composition at least partially reduces the biological availability of PRL and/or PRL-R in the subject. In an embodiment, such a composition may include a polynucleotide molecule adapted for use in RNA-interference.

In a further set of embodiments, methods of reducing and/or inhibiting the sensitivity of a pain neuron to a stimulus may include contacting the pain neuron with a pharmacologically active composition that is adapted to at least partially inhibit the biological activity of prolactin (PRL) and/or prolactin receptor (PRL-R).

In yet another set of embodiments, methods for diagnosing a pain disorder and/or determining the severity of pain experienced by a subject may include obtaining a biological sample from a subject in need thereof, and obtaining a measurement of the amount of PRL in the sample. The biological sample may include a body fluid or a tissue biopsy. In an embodiment, the biological sample may include one or more of blood, serum, saliva, cerebrospinal fluid, interstitial tissue fluid, tissue biopsy, urine, or lacrimal secretions. In an embodiment, the severity of pain experienced by a subject may be directly related to the amount of PRL present in the sample. In one embodiment, the severity of pain experienced by a subject may be associated with the gender of a subject.

BRIEF DESCRIPTION OF THE DRAWINGS

Other objects and advantages of the invention will become apparent upon reading the following detailed description and upon reference to the accompanying drawings in which:

FIG. 3A depicts the Western blot analysis of protein extracts prepared from TG of OVX rats and subjected to Western blot analysis using an anti-PRL-R antibody that recognizes both the long and the short PRL-R isoforms;

FIG. 3B depicts a histogram of the long PRL-R isofonrn determined at different dosages of estradiol;

FIG. 3C depicts a histogram of the short PRL-R isoforms determined at different dosages of estradiol;

FIG. 6A depicts the activation threshold temperature of cultured TRPV1-desensitized TG neurons derived from naïve female rats pretreated with vehicle or PRL;

FIG. 6B depicts the effect of pretreatment of cultured TRPV1-desensitized TG neurons derived from naïve female rats with PRL on the inward currents evoked at 43° C.;

FIG. 6C depicts the effect of pretreatment of cultured TRPV1-desensitized TG neurons derive from naive female rats with PRE on the inward currents evoked at 48° C.;

FIG. 6D depicts representative traces of $I_{heat}$ recordings from TG neurons pretreated with PRL or vehicle;

FIG. 6E depicts representative traces of $I_{heat}$ recordings from TG neurons pretreated with PRL or vehicle plotted as a function of temperature;

FIG. 7A depicts a representative autoradiograph showing that TRPV1 is hyperphosphorylated in acutely dissociated neurons from proestrous rats and OVX rats after treatment with PRL or vehicle;

FIG. 7B depicts the relative amount of $P^{32}$ incorporation in TRPV1 from acutely cultured TG neurons from OVX and proestrous rats;

FIG. 9A sets forth the amino acid sequence (SEQ ID NO: 47) of human pre-prolactin;

FIG. 9B sets forth the amino acid sequence (SEQ ID NO: 48) of one example of a prolactin antagonist, namely G129R-hPRL;

Figure 1:
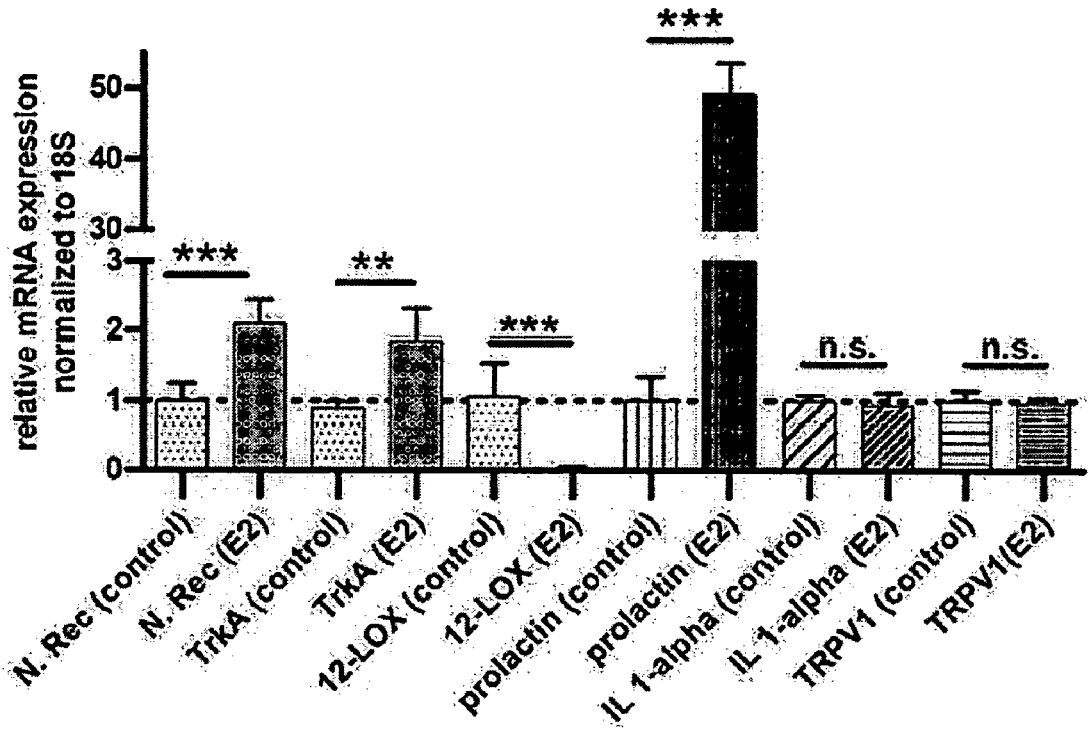
FIG. 1 is a graph depicting the relative estradiol-responsiveness in TG neurons of the genes analyzed by real-time RT-PCR selected from an Affynetrix screen.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Definitions

The terms used throughout this specification generally have their ordinary meanings in the art, within the context of the invention, and in the specific context where each term is used. Certain terms are discussed below, or elsewhere in the specification, to provide additional guidance to the practitioner in describing the various embodiments of the invention and how to make and use them. It will be appreciated that the same concept can be expressed in more than one way. Consequently, alternative language and synonyms may be used for any one or more of the terms discussed herein, nor is any special significance to be placed upon whether or not a term is elaborated or discussed in greater detail herein. Synonyms for certain terms may be provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "prolactin" or "PRL" generally refers to a single chain polypeptide hormone having a molecular weight of about 23,000 daltons, and whose amino acid sequence is substantially similar to that set forth in FIG. 9A (SEQ ID NO:47). The term is meant to encompass a variety of mutants, variants, and isoforms of PRL, including those molecules that have been post-translationally modified. The term is further meant to encompass human and non-human forms of PRL.

As used herein, the term "prolactin receptor" or "PRL-R" generally refers to a group of transmembrane proteins that belong to the class I cytokine receptor superfamily and that bind to one or more forms of PRL. Binding of PRL with a PRL-R may activate at least one of a variety of intracellular signaling pathways. Activation of said intracellular pathways upon engagement of the PRL-R by PRL may be referred to as "PRL signaling." While a variety of naturally occurring PRL-R isoforms (e.g., at least one long form and at least three short forms) resulting from alternative splicing of the PRL-R gene transcript are known in the art. Nevertheless, the term is not meant to be restricted solely to naturally occurring PRL-R isoforms, but rather encompasses any polypeptide molecule having the general properties described above, including but not limited to various mutant or variants of naturally occurring PRL-R.

As used herein, the term "PRL signaling" generally refers to one or more biological events (e.g., activation of certain intracellular signaling pathways) initiated when PRL binds to PRL-R. While it will be apparent to an ordinary practitioner of the art that at least a portion of biological events initiated by PRL signaling may be dependent on the cellular (e.g., tissue type) and/or biochemical (e.g., presence or absence of certain PRL or PRL-R modifications) context in which such binding occurs, a canonical PRL/PRL-R signaling pathway has been elucidated wherein binding of PRL to PRL-R induces dimerization of two PRL-R chains thereby triggering one or more intracellular signal transduction cascades. Signal transduction by the PRL-R involves various intracellular signaling cascades such as, for example, c-Src, JAK/STAT5, PI3-kinase, PKC and other MAPKs.

As used herein, the term "gene"; generally refers to a functional unit of a polynucleotide molecule, typically a DNA molecule, which controls or influences one or more discreet, heritable and/or transferable phenotypes. Usually, though not exclusively, a gene corresponds to a single polypeptide or RNA, or isoforms thereof. A gene may designate an entire functional unit such as is found in the genome, including but not limited to coding regions (e.g. open reading frames), non-coding regulatory regions (e.g. promoters, enhancers, termination and polyadenylation signals, and the like) and introns. Alternatively, a gene may designate only portions or fragments thereof, such as, for example, a cDNA. A gene may be either chromosomal or extra-chromosomal. Furthermore, a gene, or portions thereof, may also be inserted into a heterologous polynucleotide molecule known in the art as a "vector" (discussed below) using recombinant DNA technology.

As used herein, the term "vector" generally refers to nucleic acid molecules that transfer nucleic acid segment(s) into cells or between cells. A vector may be a component of a gene delivery system. Typically, the nucleic acid segment(s) that are to be introduced into host cells are inserted into the vector using recombinant DNA techniques. The DNA segments may be isolated from their source, may be synthesized chemically, or may be amplified using techniques such as PCR. Numerous types of vectors are known and available to ordinary practitioners of the art, and may include, but are not limited to, expression vectors, cloning vectors, shuttle vectors, viral vectors, or bacteriophage vectors. Expression vectors are typically used to deliver and to express a coding region to a eukaryotic or prokaryotic cell. Cloning vectors are typically used to isolate, propagate and manipulate isolated polynucleotide sequences during recombinant DNA procedures. Cloning vectors, which are also known in the art as "plasmids" are usually circular DNA molecules and are often, though not always, maintained in a cell in an unintegrated (i.e., extra-chromosomal) state. Shuttle vectors are typically used to transfer isolated polynucleotides between cells of the same or different species. Viral vectors are typically packaged in viral coat proteins and are used for high efficiency transfection and/or expression of isolated polynucleotides in cells. In some cases, viral vectors will integrate into a host cell genome and become a transgene. Bacteriophage vectors are often used during gene cloning procedures (e.g., isolation and enrichment of polynucleotides). An ordinary practitioner of the art would readily appreciate however, that the aforementioned vector classifications are not mutually exclusive and that the placement of a vector in one of the aforementioned classifications does not preclude its placement in additional classifications. Rather, many vectors may be placed in a plurality of the aforementioned vector classifications. For example, subsets of expression vectors are also viral vectors, and subsets of expression vectors are also shuttle vectors. Additionally, many bacteriophage vectors are also cloning, shuttle and expression vectors. An "expression vector" is a nucleic acid construct, typically generated using recombinant DNA techniques, which contains a series of specified nucleic acid elements that permit transcription of a particular nucleic acid in a host cell. An expression vector may also optionally be adapted to allow for its integration and/or replication in a host cell. An expression vector may be part of a plasmid, a virus, or a nucleic acid fragment, of viral or non-viral origin. Typically, the expression vector includes an "expression cassette," into which may be inserted, using recombinant DNA techniques, an isolated polynucleotide that is to be expressed in a host cell. The isolated polynucleotide is operably-linked to one or more appropriate nucleic acid sequences that are necessary for or that augment the expression of the isolated polynucleotide in a particular host cell or organism. Nucleic acid sequences necessary for expression in prokaryotes usually include a promoter, an optional operator, and a ribosome binding site, often along with other sequences. Nucleic acid sequences necessary for the expression of a protein from an expression vector in eukaryotic cells include at least one promoter, termination and polyadenylation signals, and one or more optional enhancers.

As used herein, the term "amino acid" generally refers to naturally occurring or synthetic amino acids, as well as amino acid analogs and amino acid mimetics that function in a manner similar to naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

When used herein in the context of polypeptides/polynucleotides, the term "variants," generally refers to two or more structurally similar polypeptides/polynucleotides that are characterized by differences in amino acid/nucleotide sequence (e.g., having at least 10%, at least 20%, at least 30%, at least 50%, at least 75%, at least 85%, or at least 95% sequence identity) and/or in biochemical modifications (e.g., post-translational modification and the like). While a subset of the general activities of certain variants may be similar, structural differences occurring between the variants may result in at least a portion of their activities being non-overlapping. A "variant" may refer to a polynucleotide or a polypeptide molecule is altered at one or more regions, including alterations in the nucleotide or amino acid sequence, as well as covalent modifications of the molecule, relative to the polynucleotide or a polypeptide molecule as it is found in nature. Thus, in some instances, the terms "variant" and "isoform" may be used interchangeably. Illustrative examples of such variants would include, by way of example only, polypeptides in which replacement of a hydrogen group by an alkyl, acyl, thiol, amide or other such functional group has occurred at one or more amino acid residues. A variant may have "conservative" changes, wherein a substituted amino acid may have similar structural and/or chemical properties (e.g., replacement of a non-polar amino acid residue with a different non-polar amino acid residue). A variant may also have "nonconservative" changes (e.g., replacement of a polar amino acid residue with a non-polar or a charged amino acid residue). Variants may also include similar minor variations in amino acid sequence including, but not limited to, deletions, truncation, insertions, or combinations thereof. Guidance in determining which amino acid residues may be substituted, inserted, or deleted without abolishing or otherwise substantially affecting biological activity is widely available in the art. Further guidance may be found using computer programs well known in the art, for example, DNASTAR software. In general, a PRL variant will retain at least a subset of the biological functions typically associated with native PRL, such as, for example, the ability to bind to a PRL-R.

As used herein, the term "polypeptide" generally refers to a naturally occurring, recombinant or synthetic polymer of amino acids, regardless of length or post-translational modification (e.g., cleavage, phosphorylation, glycosylation, acetylation, methylation, isomerization, reduction, famesylation, etc . . . ), that are covalently coupled to each other by sequential peptide bonds. Although a "large" polypeptide is typically referred to in the art as a "protein" the terms "polypeptide" and "protein" are often used interchangeably. In general, the first amino acid residue or group of amino acid residues in a polypeptide are said to be at the "amino-terminal" or "N-terminal" of the polypeptide. Similarly, the last amino acid residue, or group of amino acid residues in a polypeptide are said to be at the "carboxy-terminal" or "C-terminal".

As used herein, the term "polynucleotide" generally refers to a naturally occurring, recombinant or synthetic polymer of nucleotides (which contain sugar groups, and either purine or pyrimidine bases) that are covalently linked by sequential phosphodiester bonds. There are generally two types of polynucleotide: ribonucleic acid (RNA) and deoxyribonucleic acid (DNA). The bases involved are adenine, guanine, cytosine, and thymine (in the case of DNA) or uracil (in the case of RNA). Some nucleic acids may be informational biomolecules (e.g., DNA), or act as agent (e.g., RNA) in causing that information to be expressed (e.g., as a protein, or by its involvement in RNA-interference).

As used herein, the terms "isolated polynucleotide" or "isolated nucleic acid" generally refer to a polynucleotide, or a fragment thereof, that is free of the genes which, in the naturally occurring genome of the organism from which the nucleic acid is derived, flank the polynucleotide. The term therefore encompasses, for example, a DNA fragment that is incorporated, using recombinant DNA methodologies, into a vector; into an autonomously replicating plasmid or virus; or into the genome of a prokaryote or eukaryote; or that exists as a separate molecule (e.g., an oligonucleotide, siRNA duplexes, a cDNA or a genomic or cDNA fragment produced by PCR or restriction endonuclease digestion) independent of other sequences. It also includes recombinant DNA that is part of a hybrid gene encoding additional polypeptide sequence(s) (e.g. a fusion protein).

The term "treating" as used herein refers to administering a pharmacologically active composition prior to, during, or after the onset of clinical symptoms. The terms "in need of treatment," "in need thereof" or "who would benefit from such treatment" as used herein refers to a judgment made by a caregiver that an individual or animal requires or will benefit from treatment. This judgment is made based on a variety of factors that are in the realm of a caregiver's expertise, but includes the knowledge that the individual or animal is ill, or will be ill, as the result of a condition that is treatable by the methods embodied herein.

As used herein, the terms "pain disorder" "pain condition" or the like, generally refer to a clinical disorder of organic etiology and accompanied by nociception that causes a subject to experience a certain amount of physical pain at one or more anatomical sites, including but not limited acute pain, chronic pain, cutaneous pain, orofacial pain, somatic pain, visceral pain, cancer pain, myofascial pain and neuropathic pain. Non-limiting examples of pain disorders -familiar to those skilled in the art trigeminal pain disorders including temporo-mandibular disorders, pain associated with cancer, trigeminal neuralgia, and migraine. Certain pain disorders may be associated with sensitization of TRPV1-positive nociceptors. The terms pain disorder" or "pain condition" in the context of the presently disclosed embodiments are not meant to be confused with "psychogenic pain disorder," a somatoform disorder in which pain in one or more anatomic sites is exclusively or predominantly caused by psychologic factors.

As used herein, the terms "pain neuron," "pain receptor," or "nociceptor", generally refer to sensory neurons from structures such as the trigeminal ganglia or the dorsal root ganglia, that are activated by stimuli that produce pain. Nociceptors sense pain capable of causing injury to body tissues. The injury may be from physical stimuli such as mechanical, thermal, or electrical stimuli, or from chemical stimuli such as the presence of a toxin or an excess of a nontoxic substance.

The term "trigeminal ganglion," or "TG", generally refers to a tissue mass that contains the dendrites and somas of trigeminal nerve neurons. The trigeminal nerve is the fifth (V) cranial nerve, and carries sensory information from most of the face, as well as motor supply -to the muscles of mastication (the muscles enabling chewing), tensor tympani (in the ear) and other muscles in the floor of the mouth. The trigeminal nerve splits into three nerves—the ophthalmic nerve ($V_1$), the maxillary nerve ($V_2$) and the mandibular nerve ($V_3$).

As used herein, the term "agonist", when used in reference to a pharmacologically active compound, generally refers to a naturally occurring or synthetic ion, polypeptide, molecule, or molecular group that is capable of binding to a polypeptide receptor or group of receptors and eliciting the same or substantially similar biological responses or activities typically produced by the binding of the receptor to its natural ligand. An agonist may be either a full or a partial agonist.

As used herein, the term "antagonist", when used in reference to a pharmacologically active compound, generally refers to a naturally occurring or synthetic ion, polypeptide, molecule, or molecular group that is capable of binding to a polypeptide receptor or group of receptors and substantially inhibiting or reducing biological responses or activities typically produced by the binding of the receptor to its ligand or to an agonist. An antagonist may be either a full or a partial antagonist.

As used herein, the term "pharmacophore" generally refers to the three-dimensional arrangement of atoms—or groups of atoms—responsible for the biological activity of a drug molecule, or a group of similar drug molecules. Pharmacophore models are constructed based on compounds of known biological activity and are refined as more data are acquired in an iterative process. The models can be used for optimizing a series of known ligands or, alternatively, they can be used to search molecular databases in order to find new structural classes—a process known as virtual screening.

The term "mimetic," as used herein, generally refers to a molecule, or portions thereof, the structure of which is developed from knowledge of the structure of a reference molecule, and as such is able to effect some or all of the actions of the reference molecule. In an embodiment, a mimetic may refer to a PRL-R antagonist.

As used herein, the term "RNA-interference" or "RNAi" generally refers to the process of sequence-specific post-transcriptional gene silencing. RNAi is a process by which specific mRNAs are degraded into short RNAs. To mediate RNAi, a double-stranded RNA (dsRNA) with substantial sequence identity to the target mRNA is introduced into a cell. The target mRNA is then degraded in the cell, resulting in decreased levels of that mRNA and the protein it encodes.

As used herein, the term "RNAi construct" generally refers to small interfering RNAs (siRNAs), hairpin RNAs, and other RNA species that can be cleaved in vivo to form siRNAs. The term also encompasses expression vectors capable of giving rise to transcripts that form dsRNAs or hairpin RNAs in cells, and/or transcripts that can produce siRNAs in vivo. The term "RNAi expression vector" refers to replicable nucleic acid constructs used to express (transcribe) RNA that produces siRNA duplexes in a host cell in which the construct is expressed.

As used herein, the term "short-interfering RNA" or "siRNA" generally refers to a short (approximately 19 to about 25 nucleotides in length), double stranded RNA molecule of defined nucleotide sequence that is capable of mediating RNAi.

As used herein, the term "fusion protein" generally refers to a protein that is generated, using recombinant DNA techniques, by joining two or more defined polypeptides together to form a single protein.

As used herein, the term "stimulus", when used in reference to a neuron, generally refers to an event that causes the neuron to depolarize.

As used herein, the term "substantially identical", when used in reference to a polynucleotide, generally refers to a polynucleotide, or a portion or fragment thereof, whose nucleotide sequence is at least 95%, 90%, 85% 80%, 70%, 60% or 50% identical to the nucleotide sequence of a reference polynucleotide. When used in reference to a polypeptide, the term generally refers to a polypeptide, or a fragment thereof, whose amino acid sequence is at least 95%, 90%, 85% 80%, 70%, 60% or 50% to the amino acid sequence of a reference polypeptide. For polypeptides, the length of comparison sequences will generally at least about 5 amino acids, and may include the complete polypeptide sequence. For nucleic acids, the length of comparison sequences will generally be at least about 15 nucleotides, and may include the complete reference nucleic acid sequence. Sequence identity between two or more polypeptide or nucleic acid sequences is typically determined using sequence analysis software (e.g., Sequence Analysis Software Package of the Genetics Computer Group, University of Wisconsin Biotechnology Center) designed for this purpose. Such software matches similar sequences by assigning degrees of homology to various substitutions, deletions, substitutions, and other modifications. Conservative substitutions typically include substitutions within the following groups: Gly; Ala; Val, Ile, Leu; Asp, Glu, Asn, Gln; Ser, Thr; Lys, Arg; and Phe, Tyr.

As used herein, the term "polymerase chain reaction" (commonly referred to in the art as "PCR") generally refers to a method, or a modification thereof, for increasing the concentration of a segment of a target DNA sequence in a mixture of DNA containing the target sequence. Examples of PCR methods are shown in U.S. Pat. Nos. 4,683,195 4,683,202, and 4,965,188, which are incorporated herein by reference. The term "reverse transcriptase PCR" or, "RT-PCR", generally refers to a modified PCR procedure, in which high concentrations of DNA fragments containing a specific target DNA sequence are produced from a mixture of RNA containing the target sequence. A typical RT-PCR procedure would begin by synthesizing complementary DNA, or cDNA, from an RNA template by mixing the RNA with an oligonucleotide primer and a variant of the retroviral reverse transcriptase (RT) enzyme. The cDNA synthesized during this step may then be used in a standard PCR procedure to amplify a specified target sequence. Since RT-PCR detects RNA, the procedure is commonly used as a method to ascertain gene expression in a biological sample. The term "real-time PCR," "quantitative PCR" or "qPCR" generally refers to modified PCR procedure in which the starting amount of target DNA, cDNA or RNA relative to other molecules in a mixture can be determined. QPCR uses fluorescent signals that are generated during the PCR procedure to calculate the amount of initial template present in a biological sample. QPCR is commonly used in the art to determine the relative expression levels of one or more genes of interest.

As used herein, the term "mutant" generally refers to a polypeptide or polynucleotide whose polypeptide or polynucleotide sequence is altered at one or more positions and is different from what normally appears, occurs, or functions in nature. In the context of at least some of the present embodiments, the term generally refers to a polypeptide or polynucleotide that differs in sequence from the wild-type polypeptide or polynucleotide at one or more positions. Mutations may include deletions, truncations, insertions, substitutions, or combinations thereof, of one or more amino acids or nucleotides in a polypeptide or polynucleotide, respectively.

A "deletion", as used herein, generally refers to a change in either amino acid or nucleotide sequence in which one or more amino acid or nucleotide residues are absent. A deletion may occur at any position along a polypeptide or polynucleotide molecule.

An "insertion" or "addition," as used herein, generally refers to a change in an amino acid or nucleotide sequence resulting in the addition of one or more amino acid or nucleotide residues, respectively, as compared to the naturally occurring molecule. An insertion may occur at any position along a polypeptide or polynucleotide molecule A "substitution," as used herein, refers to the replacement of one or more amino acids or nucleotides by different amino acids or nucleotides, respectively.

A "truncation", as used herein, refers to the removal (i.e. deletion) of one or more amino acids or nucleotides from amino- or carboxy-terminal, or from the 5'- or 3'-end, of a polypeptide or polynucleotide, respectively.

As used herein, the term "recombinant," when used in reference to a polynucleotide or a polypeptide, generally refers to a polynucleotide or a polypeptide molecule that is produced using genetic engineering techniques and that it is distinct from a naturally occurring nucleic acid or polypeptide molecule.

The term "portion", as used herein, in the context of a molecule, such as a polypeptide or of a polynucleotide (as in "a portion of a given polypeptide/polynucleotide") generally refers to fragments of that molecule. The fragments may range in size from three amino acid or nucleotide residues to the entire molecule minus one amino acid or nucleotide. Thus, for example, a polypeptide "comprising at least a portion of the polypeptide sequence" encompasses the polypeptide defined by the sequence, and fragments thereof, including but not limited to the entire polypeptide minus one amino acid.

The term "wild-type" is used herein to indicate a polypeptide or a polynucleotide that contains only those amino acid or nucleotide sequences found in the protein or nucleic acid molecule as it typically occurs in nature. In other words, a wild-type molecule is a molecule that is substantially free of natural, spontaneous or experimentally induced mutations. A wild-type polypeptide or polynucleotide may be produced by recombinant means or may be isolated from a naturally occurring source.

As used herein, the term "endogenous," generally refers to a factor, such as a gene or a polypeptide, that originates from a naturally occurring source within a cell or organism. An "endogenous gene" generally refers to a gene that is a part of the original genetic repertoire of a cell or an organism. An endogenous gene may be chromosomal or extra-chromosomal (e.g. mitochondrial genes). An endogenous gene may be wild type or mutant. An "endogenous protein" generally refers to a protein that is produced from an endogenous gene.

As used herein, the term "exogenous" generally refers to a factor that originates from a source that is outside of a cell or an organism. An "exogenous gene" generally refers to a gene that is not a part of the original genetic repertoire of a cell or an organism. An exogenous gene may be delivered to a cell or a group of cells using one or more gene delivery or transfection systems. An exogenous gene may be recombinant (e.g., a gene that has been inserted into a vector), or may be naturally occurring (e.g., a gene that is part of the naturally occurring genome of a virus). An exogenous gene may be chromosomal (e.g., as a stably integrated "transgene") or extra-chromosomal (e.g., as an unintegrated vector).

As used herein, "conserved region" generally refers to any stretch of six or more contiguous amino acids in a polypeptide that exhibit at least 30%, or between 50% to 70% amino acid, or between 60% to 95% sequence identity to the corresponding region of one or more reference polypeptides.

As used herein, the term "pharmaceutical composition" or "pharmaceutical preparation" generally refers to a formulation that has been adapted to deliver a prescribed dosage of one or more therapeutically useful agents to a cell, a group of cells, an organ or tissue, an animal or a human. A pharmaceutical preparation may be prepared as a solid, semi-solid, gel, hydrogel, liquid, solution, suspension, emulsion, aerosol, powder, or combinations thereof. Included in a pharmaceutical preparation may be one or more carriers, preservatives, flavorings, excipients, coatings, stabilizers, binders, solvents and/or auxiliaries.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein, terms such as "biological availability," "bioavailablity," or the like generally refer to the relative amount of a biologically active factor or substance that is available to carry out a biological function.

It is an objective of the present application to provide methods and compositions for the treatment of pain disorders, in particular female-biased pain disorders (i.e., pain disorders that occur with greater frequency and severity in women). The female sex hormone 17-β-estradiol (also known as "estrogen", "estradiol", or "E2") has been implicated as one of the factors that may account for the observed gender bias in certain pain disorders.

In accordance therwith, the effect that the female sex steroid estradiol has on gene expression in peripheral nociceptors was assessed, with particular emphasis on the role of estradiol in modulating changes in gene expression in trigeminal neurons.

Identification of Estradiol-Responsive Genes in Trigeminal Nociceptors.

To identify estradiol-responsive genes involved in nociception, an Affymetrix microarray screen was performed using cDNA prepared from trigeminal ganglia (TG) from OVX rats that had been pre-treated with 80 µg/kg/day for 10 days either estradiol or vehicle. Results obtained from this screening strategy are summarized in Table 1. The S.A.M. and GeneSpring 5.1 analyses identified 18 genes whose expression increased and 3 genes whose expression decreased. Genes were selected for further analysis based upon their known involvement in nociception (e.g., interleukin-1 alpha, 12-lipoxygenase, TRPV1 and trkA), or based upon their maximal responsiveness to estradiol (e.g., PRL). The expression profile of genes selected using the microarray screen was confirmed by real-time RT-PCR. Validated primers were used for each gene and expression was normalized to the housekeeping gene 18S. Data are presented as mean±SEM (n=5/group, =p<0.01 and *=p<0.001 versus respective vehicle control; two-tailed unpaired T test). The results depicted in FIG. 1 show that expression of the selected genes was in accordance with the microarray data with the exception of interleukin-1 alpha, which appears to be a false positive (Table 1 vs. FIG. 1). Unexpectedly, PRL mRNA exhibited a 48-fold increase (p<0.001) in expression in response to estradiol (see FIG. 1). For this reason, PRL was selected for further study as a candidate therapeutic target for female-biased pain disorders.

tion. The PRL protein level was significantly increased in the TG of proestrous rats compared to the OVX vehicle control rats (FIGS. 2B and 2C). The specificity of anti-PRL antibodies was evaluated by a use of the blocking peptide corresponding to the epitope of PRL. Pre-absorption of anti-PRL antibodies with the blocking peptide nearly eliminated the PRL-specific band (FIGS. 2B, 2C).

TABLE 1

Effect of estradiol administration (80 µg/kg/10 days) versus vehicle on gene expression in trigeminal ganglia of ovariectomized rats as assessed by Affymetrix microarray

| Probe Set ID No. | NCBI Accession No. | Gene Name | SAM[1] | GS[1] |
| --- | --- | --- | --- | --- |
| | | Concordant increasers | | |
| E03166cds_s_at | NM_012629 | Prolactin | 6.9 | ≧1.5 |
| V01244_at | NM_012629 | Prolactin | 12.8 | ≧1.5 |
| V01250cds_s_at | NM_012629 | Prolactin | 3 | ≧1.5 |
| AA958274_at | AA958274 | Trk A 3' mRNA sequence | 1.5 | ≧1.5 |
| AB002393_at | NM_017159 | Histidine ammonia lyase | 1.5 | ≧1.5 |
| AF050662UTR#1_at | NM_031593 | Ania-10 early gene mRNA, 3' UTR | 1.6 | ≧1.5 |
| AF050664UTR#1_at | XM_220080 | Ania-12 early gene mRNA, 3' UTR | 1.5 | ≧1.5 |
| AF087674_at | XM_573948 | Insulin receptor substrate 2 (IRS-2) mRNA | 1.4 | ≧1.5 |
| D00403_g_at | NM_012537 | Interleukin 1 alpha | 1.3 | ≧1.5 |
| D14097cds_s_at | NM_017019 | Aldosterone synthase, exon 9 | 1.5 | ≧1.5 |
| D38381_s_at | NM_145782 | Cytochrome P450, 3a18 | 1.3 | ≧1.5 |
| D49494cds_s_at | NM_024375 | Prepro bone inducing protein | 1.3 | ≧1.5 |
| M25801_g_at | NM_145776 | Nuclear receptor subfamily 1, Group D, member 1 | 1.5 | ≧1.5 |
| M26127_s_at | NM_012541 | Cytochrome P450, 1a2 | 1.3 | ≧1.5 |
| X54419cds_at | NM_021834 | Interleukin 5 (colony-stimulating factor, eosinophil) | 1.3 | ≧1.5 |
| X60328_at | NM_022936 | Cytosolic epoxide hydrolase | 1.7 | ≧1.5 |
| rc_AA859966_i_at | AA859966 | Similar to *M. musculus* pre 45S pre rRNA gene | 4.1 | ≧1.5 |
| rc_AA945571_sat | NM_001013904 | Cytochrome P450, subfamily IIC6 | 1.7 | ≧1.5 |
| | | Concordant decreasers | | |
| S69383_at | NM_031010 | Arachidonate 12-lipoxygenase | 0.5 | ≦1.5 |
| M31809_at | NM_017042 | Protein phosphatase 3, catalytic subunit, beta isoform | 0.6 | ≦1.5 |
| Rc_AA894174_at | N_M_001009668 | Electron transf. flavoprotein (Etfa), mRNA | 0.7 | ≦1.5 |

[1] Affymetrix microarray experiment was performed with TG RNA isolated from vehicle-treated or E2 (80 µg/kg/10 days) (n = 5 per group). Results were individually analyzed using two independent methods: Statistical Analysis of Microarrays (SAM) and GeneSpring 5.1 (GS). There were 18 genes found to be upregulated (identified as concordant increasers) and 3 genes were found to be downregulated (identified as concordant decreasers) using bothmethods. Data are presented as Mean with False Discovery Rate (FDR) of 10% for SAM and change cut-off for GS.

PRL Expression in Trigeminal Sensory Neurons is Regulated by Estradiol.

Figure 2:
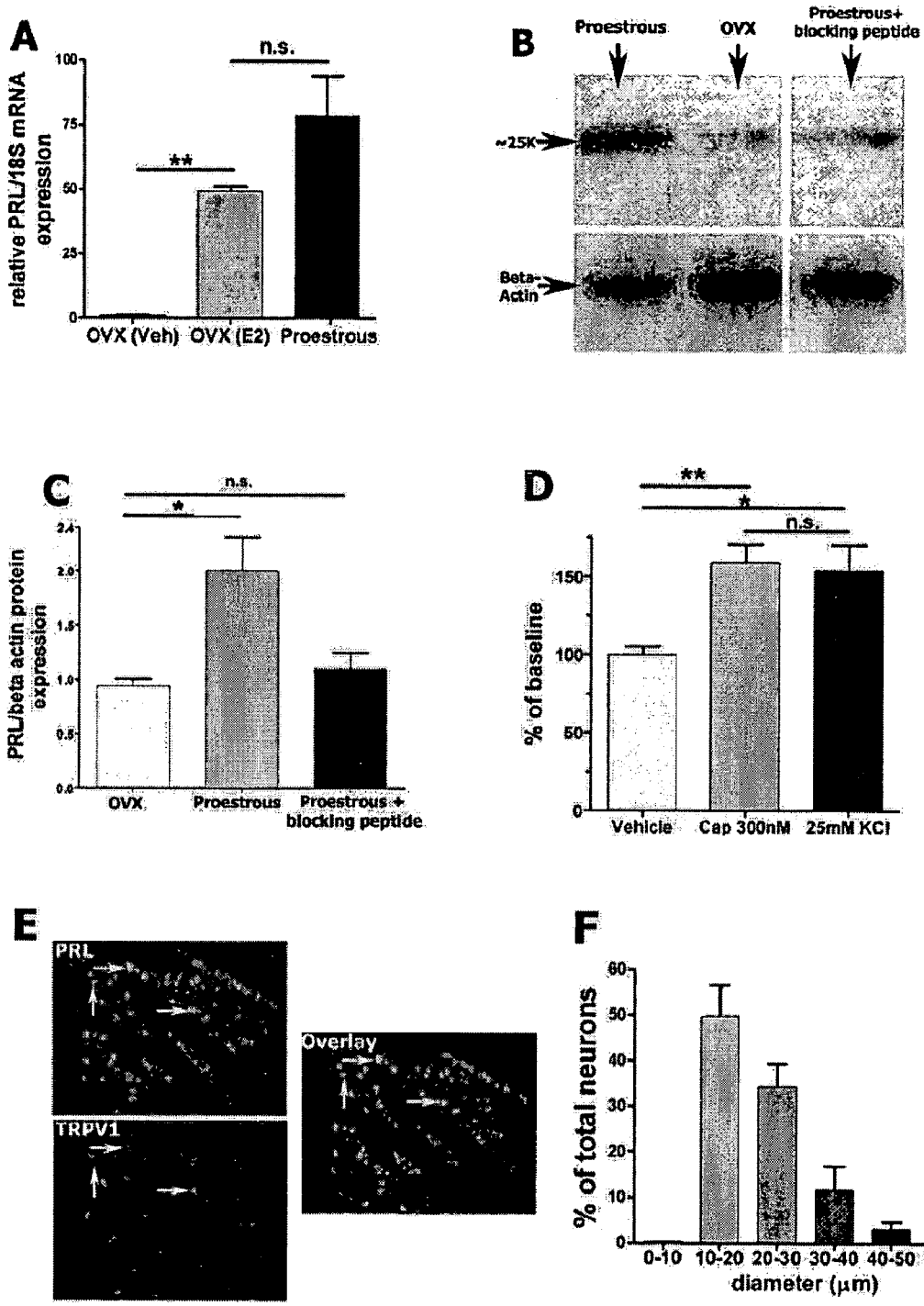
FIG. 2A depicts a histogram of the relative PRL/18S mRNA expression in proestrous female rats or OVX female rats pretreated with either vehicle or estradiol.
FIG. 2B depicts Western blot analysis of TG samples collected from proestrous female rats, OVX female rats, and proestrous female rats treated with blocking protein.
FIG. 2C depicts a histogram quantifying the results of the Western blot analysis of FIG. 2B.
FIG. 2D depicts a histogram of the relative amount of PRL released from TG neurons from proestrous rats.
FIG. 2E depicts photographs of an immunohistochemical analysis of PRL and TRPV1 performed on proestrous rat TG tissue.
FIG. 2F depicts the cell size distribution of the PRL-containing neurons.

A set of experiments designed to characterize the regulation of PRL mRNA and protein expression by either exogenous or endogenous estradiol was performed. Turning to FIG. 2, Real-time RT-PCR experiments were performed using TG RNA prepared either from proestrous female rats or OVX female rats pretreated with either vehicle or estradiol (80 µg/kg/day×10 days). Reactions were performed using primers specific for PRL gene and the internal control (18S). Data were normalized to the relative amount of OVX (vehicle) PRL mRNA/18S. Data are presented as mean±SEM (n=5/group, =p<0.01 and *=p<0.001 vs. PRL mRNA of the OVX/Vehicle group; one-way ANOVA with Bonferroni's post hoc test). FIG. 2A shows that PRL mRNA expression in TG collected from OVX rats treated with estradiol replacement is increased approximately 50-fold (p<0.01) compared to PRL mRNA from the TG of OVX control rats. Moreover, the relative PRL mRNA expression in the TG of intact female rats during proestrous was 78-fold greater (p<0.001). The TG samples collected from these groups were also subjected to Western blot analysis to determine the relative expression of PRL protein. FIG. 2B shows that PRL from TG migrates as a single band at approximately 25 KDa, corresponding to full length PRL protein. The results obtained from these experiments were quantified as described in the METHODS section.

PRL is known to be released from cells of the anterior pituitary (Zacur et al. 1976) and from extrapituitary sites (Ben-Jonathan et al., 2002; Zinger et al., 2003; Torner et al., 2004). To determine whether PRL protein is present in a releasable pool in TG sensory neurons, cultured TG neurons derived either from proestrous rats (cultured in the presence of 50 nM E2) or from OVX rats (cultured without E2) were exposed to 300 nM capsaicin or 25 mM KCl buffer. The results obtained from these experiments are depicted in FIG. 2D, which indicate that a substantial amount of PRL is released from TG neurons of proestrous rats cultured in the presence of E2 upon stimulation with either capsaicin (158±12% of vehicle) or KCL (154±16% of vehicle). In contrast, no detectable release of immunoreactive PRL was observed in neurons from OVX rats cultured in the absence of E2 (data not shown). Data are presented as mean % of basal release±SEM (n=6/group, *=p<0.05 and **=p<0.01; one-way ANOVA with Bonferroni's post hoc test).

Prolactin is Expressed by TRPV1-containing Trigeminal Neurons.

Based on the finding that capsaicin evokes release of PRL from TG cultures, PRL expression in the TRPV1-positive subset of nociceptors was characterized. Immunohistochemical analysis of PRL (stained green) and TRPV1 (stained red) was performed on proestrous rat TG tissue. Neurons co-expressing PRL and TRPV1 appear yellow when these two images are merged. FIG. 2E shows representative results obtained with this experiment. Examples of neurons co-expressing PRL and TRPV1 (yellow) are indicated by horizontal arrows, whereas a vertical arrow shows a PRL+ neuron that is not positive for TRPV1. Results depicted in FIG. 2E demonstrate that PRL protein is only expressed by neurons in the TG, and not by other cell types found in the ganglia. Immunoreactive PRL was present in 35.1±1.5% (907/2591 neurons) of all proestrous rat TG neurons, while anti-TRPV1 labeled approximately 31.6±1.4% (830/2591 neurons) of TG neurons. Furthermore, 90.3±2.0% (819/907 neurons) of the PRL containing neurons were also positive for TRPV1 (FIG. 2E). FIG. 2F shows the cell size distribution of the PRL-containing neurons. Approximately 50% of PRL-positive cells were of small diameter (0-20 μm), 46.12% were of medium diameter (20-40 μm) and 3.7% were of large diameter (40-60 μm). The mean cell size was of 21.4 μm (n=1160). PRL immunoreactivity was detected primarily in small-sized (0-20 μm; 50%) and medium-sized (20-40 μm; 46.12%) sensory neurons with a mean value of 21.4 μm (FIG. 2F).

Estradiol Increases Expression of the Long Form of the PRL-R.

There are two isoforms of the rat PRL receptor (PRL-R) that differ in the length of their cytoplasmic tail and are therefore termed the long and short isoforms. Most biological functions of the PRL-R are attributed to the long form (Jabbour and Kelly, 1997) and the relative expression ratio of the long and short forms has been shown to be important in determining the responsiveness of cells to PRL (Perrot-Applanat et al., 1997; Hu et al., 2001; Meng et al., 2004). Moreover, the differential expression of these receptors is regulated by estrogen in certain tissues (Sakaguchi et al., 1994; Pi et al., 2003). To determine whether estrogen regulates the expression of the PRL-R in the female TG, protein extracts prepared from TG of OVX rats and subjected to Western blot analysis using an anti-PRL-R antibody that recognizes both the long and the short PRL-R isoforms. FIG. 3A depicts a representative immunoblot of this experiment. The antibody recognized two bands migrating at approximately 100 KDa and 40 KDa corresponding to the long and short PRL-R isoforms respectively. Blots were stripped and probed with an antibody against beta-actin to normalize for loading differences. Immunoblots were quantified and the results are depicted in FIGS. 3B and 3C, which demonstrate that estrogen increases expression of the long form of PRL-R in the TG of OVX rats in a dose-dependent manner (FIG. 3B), but does not appear to significantly affect expression of the short form of the PRL-R (FIG. 3C). The data are presented as mean±SEM (n=4/group, *=p<0.05 and **=p<0.01; one-way ANOVA with Bonferroni's post hoc test).

The results presented thus far demonstrate that the female sex steroid estradiol influences expression of a variety of genes in sensory ganglia. Furthermore, these results have led to the novel and unexpected findings that PRL mRNA appears to be a highly estradiol-responsive transcripts in TG; that PRL is present in sensory neurons in a releasable pool; and that the expression of PRL as well as long form of PRL-R are increased by estradiol. Without being bound by any particular theory or mechanism of action, it appears that in the presence of estradiol, at least the minimal components required for PRL-signaling to occur are present in sensory neurons. The following studies were performed to ascertain whether PRL-signaling can occur in estradiol-sensitized sensory neurons.

Prolactin Increases Capsaicin-Evoked Accumulation in Intracellular Calcium of TG Neurons from Intact Female, but not OVX Rats.

Figure 4:
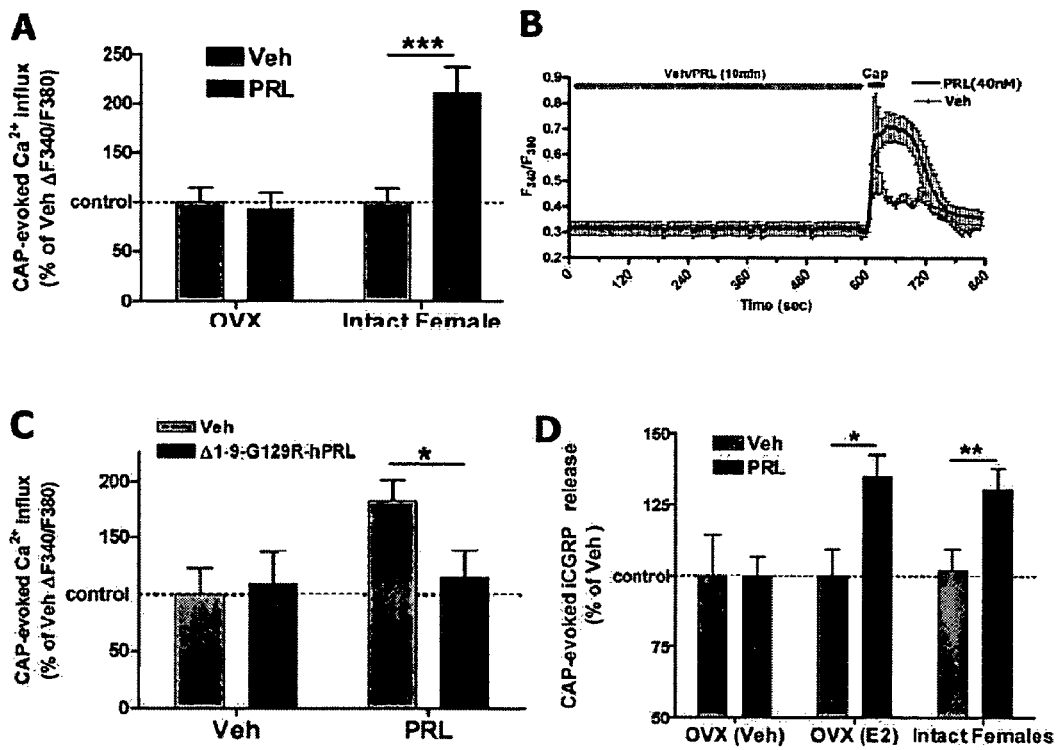
FIG. 4A depicts the results of $Ca^{2+}$ imaging experiments performed in acutely dissociated TG neurons.
FIG. 4B depicts representative traces of $Ca^{2+}$ imaging experiments performed in neurons from proestrous rats.
FIG. 4C depicts the effect on $Ca^{2+}$ influx when cultured neurons were treated with the PRL-R antagonist 1-9-Δ-G129R-hPRL (800 nM)
FIG. 4D depicts the effect on $Ca^{2+}$ influx when cultured neurons were treated with the PRL-R.

The binding of PRL to the PRL-R activates a variety of intracellular signaling pathways in non-neuronal cells (Bole-Feysot et al. 1998), some of which are known to be involved in the sensitization of TRPV1 in nociceptors (Cesare and McNaughton, 1996). To evaluate whether PRL sensitizes capsaicin activation of TRPV1, changes in calcium ($Ca^{2+}$) influx were quantified in acutely dissociated TG neurons. FIG. 4A depicts the results of $Ca^{2+}$ imaging experiments performed in acutely dissociated TG neurons. Data are presented as mean % of vehicle±SEM (n=30/group, ***=p<0.001; two-way ANOVA). FIG. 4B depicts representative traces of $Ca^{2+}$ imaging experiments performed in neurons from proestrous rats. Neurons were treated with 40 nM PRL or vehicle for 10 min followed by a 40 sec capsaicin (30 nM) application. PRL did not evoke $Ca^{2+}$ influx on its own, but potentiated capsaicin-evoked $Ca^{2+}$ influx. Data are presented as mean $F_{340/F380}$±SEM (n=8/group; error bars are SEM). These result demonstrate that application of PRL (40 nM) for 10 min significantly (p<0.001) increases capsaicin-evoked accumulation of intracellular $Ca^{2+}$ ($[Ca^{2+}]_i$) in neurons isolated from intact female rats. PRL appears to increase the magnitude of capsaicin-evoked $Ca^{2+}$ influx in TG neurons by about 71% compared to that observed in TG neurons not exposed to PRL, whereas PRL had no effect on capsaicin-evoked calcium influx in neurons from OVX control rats (FIG. 4A).

To determine whether PRL augmentation of capsaicin responses occurs through the PRL-R (i.e., whether PRL-signaling could account for the observed effects of PRL on nociceptors sensitization), $Ca^{2+}$ imaging experiments were performed on neurons in the presence of a molar excess of a full PRL-R antagonist (Δ 1-9-G129R-hPRL) (Bernichtein et al., 2003; Goffin et al., 2005). Cultured neurons were treated as described in the previous experiment. In addition, neurons were co-treated with PRL and the PRL-R antagonist 1-9-Δ-G 129R-hPRL (800 nM). As depicted in FIG. 4C, the presence of a PRL-R antagonist significantly blocked PRL potentiation of capsaicin-evoked $Ca^{2+}$ influx, whereas it had no effect on its own. Data are presented as mean % of vehicle±SEM (n=19-40, *=p<0.05; two-way ANOVA).

Since estradiol increases the expression of the long isoform of the PRL-R in TG from OVX rats, it was reasoned that the loss of PRL modulatory effects observed in TG neurons cultured from OVX rats could be reversed by the addition of exogenous estradiol to those cultures. To this end, iCGRP release experiments were performed using TG neurons from intact female or OVX rats that were cultured for 5 days in presence of 50 nM estradiol (E2) or vehicle. Release of iCGRP from cultured neurons was measured by radioimmunoassay. Data are presented as mean % of vehicle±SEM (n=4/group, *=P<0.05 and **=P<0.01 vs. iCGRP levels of each control group; two-tailed unpaired T test). Turning to FIG. 4D, it can be seen that PRL sensitization of capsaicin-evoked iCGRP release from cultured TG neurons derived from OVX rats is significantly restored when cultured for 5 days in the presence of exogenous estradiol (50 nM), whereas no effect was observed on OVX TG neurons cultured in the absence of E2. Thus, it appears that in the presence of estradiol, the components required for PRL-signaling to occur are present in TG nociceptors, and that the components indeed appear to constitute a bona fide PRL-signaling axis that sensitizes nociceptors to activating stimuli.

Prolactin Sensitizes Capsaicin-Induced Currents in Intact Female, but not OVX Rat TG Neurons.

Figure 5:
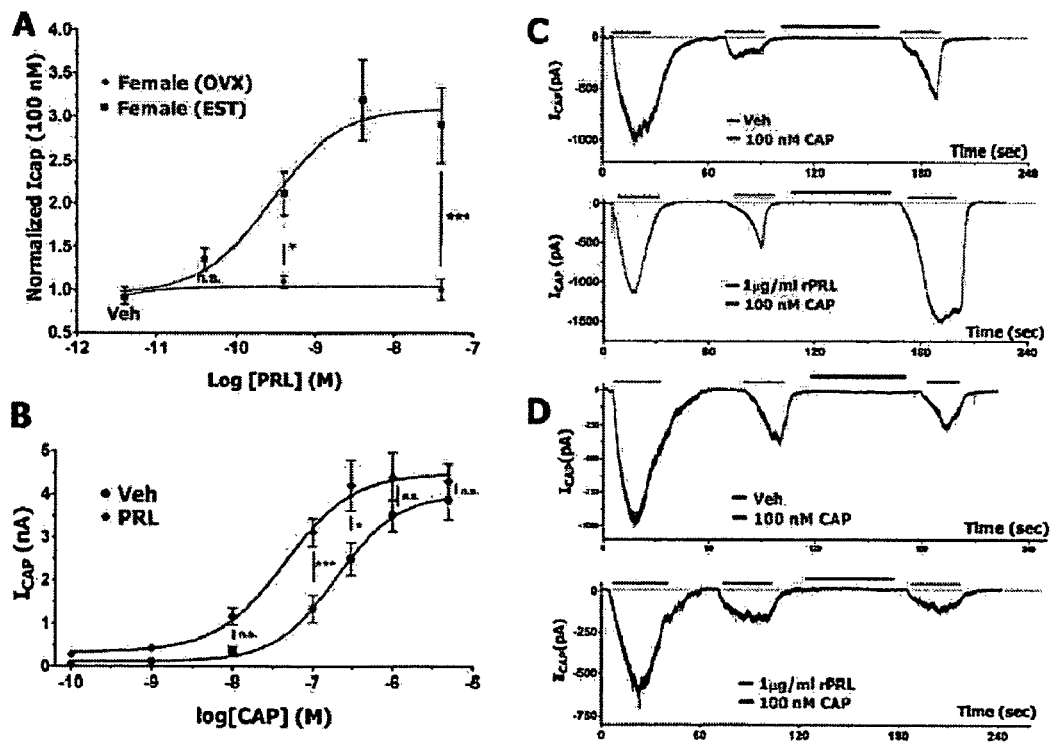
FIG. 5A depicts a graph of normalized Icap vs. the dosage of PRL given to cultured TRPV1-desensitized TG neurons derived from naïve female rats.
FIG. 5B depicts a depicts a graph of Icap vs. dosage of capsaicin given to cultured TRPV1-desensitized TG neurons derived from naïve female rats pretreated with vehicle or PRL.
FIG. 5C depicts traces of $I_{cap}$ recordings from intact female rat TG neurons.
FIG. 5D traces of $I_{cap}$ recordings from OVX female rat TG neurons

Since application of PRL rapidly increases capsaicin-induced calcium accumulation and neuropeptide release, the role of PRL in modulating capsaicin-induced currents ($I_{cap}$) was examined. TRPV1 desensitization of cultured TG neurons was induced through the repeated application of 100 nM capsaicin to the cultures (Vellani et al., 2001; Bonnington and McNaughton, 2003). The sub-maximal concentration of capsaicin used was effective in inducing desensitization and permitted the investigation PRL-evoked re-sensitization or further sensitization of TRPV1. The results depicted in FIG. 5A show that pretreatment of cultured TRPV1-desensitized TG neurons derived from naive female rats with PRL sensitized $I_{cap}$ in a dose-dependent manner, with maximal potentiation observed at 40 nM (i.e. 1 µg/ml) and with $EC_{50}$ of 0.27 nM. Data are presented as mean±SEM of PRL-treated $\Delta I_{cap}$ ($3^{rd} I_{cap} - 2^{nd} I_{cap}$) normalized to vehicle treated $\Delta I_{cap}$, ($n=8-12$/group, *=p<0.05 and **=p<0.01; two-way ANOVA). The data shown in FIG. 5B demonstrate that pretreatment of acutely dissociated TG neurons with PRL results in increased capsaicin potency. Acutely dissociated TG neurons from female rats were locally pretreated with vehicle or PRL (40 nM) for 60 sec, washed for 60 sec and subjected to a single capsaicin pulse (40 sec, 0.1 nM-5 µM). Data are shown as mean±SEM (n=12-20/group, *=p<0.05 and ***=p<0.001 vehicle vs. PRL; two-way ANOVA). FIGS. 5C and 5D depict representative traces of $I_{cap}$ recordings from intact (FIG. 5C) and OVX (FIG. 5D) female rat TG neurons. Concentration of applied CAP and PRL are indicated. The duration CAP and PRL treatment was 30 sec and 60 sec, respectively. The magnitude of the second capsaicin-evoked inward currents ($I_{cap}$) peak was subtracted from the third Icap peak to calculate the difference ($\Delta I_{cap}$). Data were normalized to the vehicle treated $\Delta I_{cap}$. Further, in agreement with $Ca^{2+}$ imaging and iCGRP release data discussed above, PRL had no observed effect on $I_{cap}$ recorded from rat OVX TG neurons (FIGS. 5A and 5D).

Prolactin Sensitizes Heat-Evoked Currents in Female Rat TG Neurons.

TRPV1 is known to be activated by noxious heat (>42° C.). Furthermore, this effect is itself sensitized by hyperalgesic agents such as bradykinin (Cesare et al., 1999) and NGF (Chuang et al., 2001; Zhu et al., 2004). To determine whether PRL sensitizes heat-evoked currents ($I_{heat}$), the effect that pre-treatment of intact female rat TG neurons with PRL has on $I_{heat}$ was examined. The data presented in FIG. 6A demonstrates that pretreatment with PRL (40 nM for 5 min) significantly decreased the threshold temperature for $I_{heat}$ activation (41.9±0.67° C., n=16 vs. 36.8±0.58° C., n=16; t-test, p<0.0001; FIGS. 6A and 6D) in cultured trigeminal neurons from intact female rats. Data are presented as mean±SEM (n=8-12/group, *=p<0.001 versus vehicle control; two-tailed unpaired T test). FIGS. 6B and 6C demonstrate that pretreatment with PRL of cultured trigeminal neurons from intact female rats significantly increased inward currents evoked by 43° C. (FIG. 6B) and 48° C. (FIG. 6C). Data are presented as mean±SEM (n=8-12/group, *=p<0.001 versus vehicle control; two-tailed unpaired T test). FIG. 6D and FIG. 6E are representative traces of $I_{heat}$ recordings from TG neurons pretreated with PRL or vehicle (6D); and plotting $I_{heat}$ as a function of temperature (FIG. 6E). PRL lowered the activation temperature threshold and increased the magnitude of $I_{heat}$. In addition, the magnitude of the $I_{heat}$ evoked at 43° C. ($I_{43}$) and 48° C. ($I_{48}$) points in neurons pretreated with prolactin or vehicle was measured. Pretreatment with PRL dramatically increased both $I_{43}$ (FIGS. 6B and 6E) and $I_{48}$ (FIGS. 6C and 6E).

Phosphorylation of TRPV1 Occurs in the Presence of PRL-Signaling.

The activity of TRPV1 is dependent upon its phosphorylation status. Hyperphosphorylation of TRPV1 is associated with increased responsiveness to capsaicin (Bhave et al., 2003; Mohapatra and Nau, 2005; Zhang et al., 2005; Mandadi et al., 2006). Since PRL-signaling through PRL-R is known to activate various intracellular kinases pathways, the effect of PRL on TRPV1 phosphorylation status in cultured TG neurons was assessed. Cultured TG neurons were incubated with PRL (40 nM) or vehicle for 10 min in the presence of radioactive phosphate ($P^{32}$-orthophosphate). Extracts of the radiolabelled TG cultures were prepared and subjected to immunoprecipated using an antibody that specifically recognizes TRPV1, and the resulting immune complexes were resolved by SDS-PAGE and prepared for immunoblot analysis. The blots were subjected to autoradiography to visualize radiolabelled $P^{32}$-TRPV1 and to determine its relative abundance in the presence of PRL. The resolved protein was then immunoblotted using an antibody raised against TRPV1 to ensure that the observed differences in radiolabelled TRPV1 abundance are not due to technical errors (e.g., unequal gel loading).

Turning to FIG. 7, it can be seen that PRL-signaling increases the phosphorylation state of TRPV1 (150±13%) in the neurons from intact female rats, but appears to have no observable effect on TRPV1 phosphorylation status in TG neurons from OVX rats. FIG. 7A is a representative autoradiograph showing that TRPV1 is hyperphosphorylated in acutely dissociated neurons from proestrous rats OVX and after treatment with PRL or vehicle. FIG. 7B shows the relative amount of $p^{32}$ incorporation in TRPV1 from acutely cultured TG neurons from OVX and proestrous rats. Autoradiograph U.OD. was normalized by the TRPV1 U.OD. of each treatment group. PRL significantly induced TRPV1 phosphorylation in neurons from proestrous but, as observed in previous experiments, had no effect in neurons from OVX rats. Data are presented as mean±SEM (n=3/group, *=p<0.05; two-tailed unpaired T test).

Prolactin Sensitizes Female Rats to Capsaicin-Evoked Nocifensive Behavior by an Estrogen-Dependent Mechanism.

Figure 8:
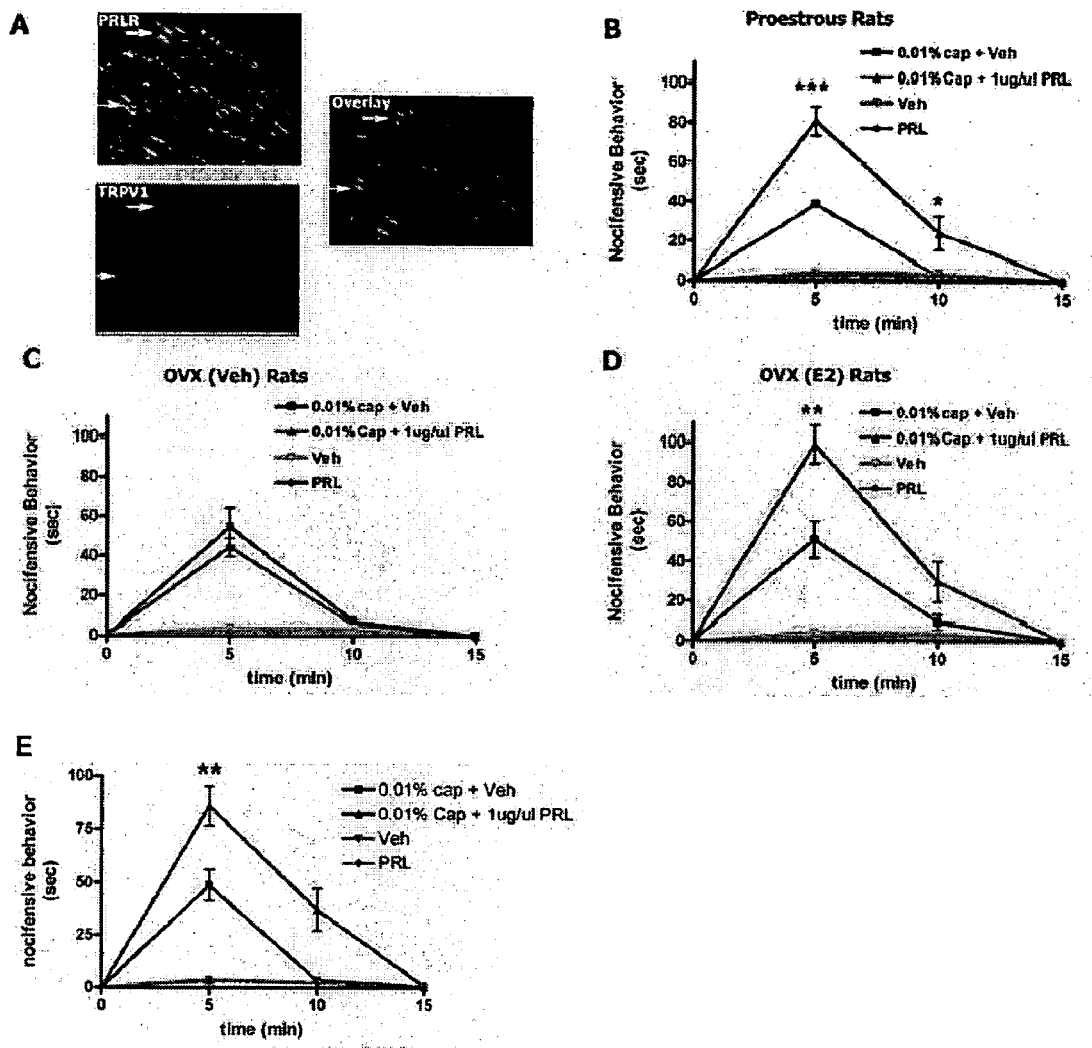
FIG. 8A depicts the results of immunohistochemical analysis of corneal cryosections from proestrous females.
FIG. 8B depicts the effect of pretreatment of proestrous rats with PRL on capsaicin-mediated nocifensive behavior.
FIG. 8C depicts the effect of pretreatment of OVX rats with PRL on capsaicin-mediated nocifensive behavior.
FIG. 8D depicts the effect of pretreatment of estradiol treated OVX rats with PRL on capsaicin-mediated nocifensive behavior.
FIG. 8E depicts the effect of pretreatment of male rats with PRL on capsaicin-mediated nocifensive behavior.

As has been described above, PRL modulation of TRPV1 activity in cultured TG neurons is, at least in part, under the control of estradiol. To whether this effect has relevance to capsaicin-induced nociception in the whole animal, corneal wipe tests were performed. In this test, corneal application of capsaicin induces a brief nocifensive behavior in the trigeminal region of awake animals (Price et al., 2004; Neubert et al., 2005; Tender et al., 2005). The cornea is a specialized tissue innervated by trigeminal sensory neurons including TRPV1 positive C-fibers (Guo et al., 1999). Turning to FIG. 8A, the results of immunohistochemical analysis of corneal cryosections from proestrous females reveal the presence of fibers that stain positive for both PRL-R (green) and TRPV1 (red) (FIG. 8A). Overlaying these two images demonstrates that a significant number of TRPV1-positive fibers innervating the cornea co-express PRL-R (yellow) which are indicated by arrows.

Data shown in FIG. 8B demonstrates that pretreatment of proestrous rats with PRL significantly increases capsaicin-mediated nocifensive behavior. In this test, the effect of PRL pretreatment on capsaicin-induced eye wiping in proestrous rats was examined. PRL (1 µg/ul in saline) or vehicle (40 µl) was applied in the cornea immediately followed by application of 0.01% capsaicin or vehicle (40 μl) and the total time spent grooming the injected eye per 5 min bins was measured by observers blinded to treatment allocation. Data are shown as mean±SEM (n=6/group *=p<0.05 and *=p<0.001; two-way ANOVA). However, as shown in FIG. 8C no change in capsaicin-responsiveness was observed in OVX female rats upon PRL or vehicle pretreatment. Data are shown as mean±SEM (n=6/group; two-way ANOVA). In agreement with results obtained from in vitro studies, results shown in FIG. 8D demonstrate that treatment of OVX female rats with estradiol restores PRL sensitization of capsaicin nocifensive behavior. Data are shown as mean±SEM (n=6/group, =p<0.01; two-way ANOVA). The effect of PRL on capsaicin-mediated nocifensive response was assessed next in male rats, in order to determine whether the influence of PRL-signaling on nociception is conserved between gender. Corneal wipe tests were performed on age-matched male rats essentially as described above. Data in FIG. 8E are shown as mean±SEM (n=6/group, **=p<0.01; two-way ANOVA). Unexpectedly, the capsaicin-mediated nocifensive response profile of male rats is strikingly similar to that of proestrus rats (compare FIG. 8E with FIG. 8B) and estradiol-treated OVX rats (compare FIG. 8E with FIG. 8D), and divergent from that found in control OVX rats treated with vehicle. Thus, it appears that PRL-signaling influences nociceptor sensitization in male rats as well as female rats, although it is of course possible that the influence of PRL on nociception is males is not as tightly associated with estradiol as in females.

SUMMARY

Numerous studies have established estrogen as a modulator of pain sensitivity, possibly acting at both peripheral nociceptors and central processing pathways (Akitoshi et al., 2000; Fillingim and Ness, 2000). Nevertheless, molecular mechanisms underlying the link between the female sex steroid estrogen and peripheral nociception have remained unclear.

In the present disclosure, it has been demonstrated that estradiol modulates the expression of several genes in trigeminal sensory neurons in female rats. It has further been demonstrated that PRL mRNA is a highly estradiol-responsive transcript in TG neurons of OVX rats undergoing estradiol replacement (>40 fold). It has been demonstrated further still that: PRL is present in sensory neurons in a releasable pool; that in addition to PRL, sensory neurons express PRL-R, and its expression is also estrogen-responsive; that in the presence of PRL, sensory neurons are sensitized at least to capsaicin- and heat-evoked responses in vitro and in vivo and that this effect is influenced by estradiol; and that a biologically functional PRL-signaling pathway exists in sensory neurons, the activation of which sensitizes neurons to activating stimuli. Importantly, it has been determined that PRL-induced sensitization of sensory neurons can be blocked by inhibiting PRL-signaling.

Thus, the novel and unexpected findings that signaling of PRL though PRL-R in nociceptors causes an increase their sensitivity to noxious stimuli indicates that the PRL-signaling axis is a valid therapeutic target for the treatment of certain pain disorders. Moreover, it has been shown that the ability of PRL to sensitize nociceptors to painful stimuli can be blocked by providing agents or compositions that disrupt PRL-signaling. Thus present findings allow for the development of compositions that disrupt PRL-signaling suitable for use as a novel class of medicaments to treat pain disorder, including those pain disorders that show a gender bias toward females. Importantly however, the showing that nocifensive responses in males are also influenced by PRL indicates the such medicaments may find use in equally in therapeutic applications provides to both females and males.

In accordance with an objective, methods for treating pain disorders are provided for, said methods including at least partially disrupting PRL signaling in sensory neurons. The embodiments described herein may be applied to inhibit, reduce and/or treat pain in a subject. By at least partially disrupting PRL-signaling in nociceptors, the increased sensitivity thereof to activating stimuli may be reduced or inhibited.

In a first set of non-limiting embodiments, PRL signaling in pain neurons may be at least partially disrupted by contacting pain neurons with a composition that includes one or more PRL-R antagonists (PRLR-A). Suitable PRL-R antagonists for use with the present embodiments may include any naturally occurring or synthetic ion, polypeptide, molecule, or molecular group that is capable of binding to PRL-R and at least partially inhibiting or reducing biological responses or activities typically produced when PRL signaling is initiated. PRL-R antagonists that are suitable for use herein include full or partial PRL-R antagonists.

In some embodiments, a PRL-R antagonist suitable for use in the embodiments described herein may be a polypeptide molecule. In some embodiments, the polypeptide molecule may be a variant of naturally occurring PRL. The term "PRL variant" generally refers to a form of PRL that has been altered relative to wild-type PRL, including where the amino acid sequence of wild-type PRL has been altered by the insertion, deletion, and/or substitution of one or more amino acids. Numerous PRL variants that act as either full and/or partial PRL-R antagonists in various tissues are known in the art. For example U.S. patent application Ser. No. 20050118586 by Bejanin et al. entitled "Human cDNAs and proteins and uses thereof" teaches CS-5b polypeptide fragments that are prolactin antagonists. U.S. Patent Application Ser. No. 20040136952 by Bhaskaran et al. entitled "Polymer conjugates of cytokines, chemokines, growth factors, polypeptide hormones and antagonists thereof with preserved receptor-binding activity" teaches the production of prolactin antagonists by conjugating certain water-soluble polymers thereto. U.S. patent application Ser. No. 20040127407 by Chen entitled "Human prolactin antagonist-angiogensis inhibitor fusion proteins" teaches certain human prolactin antagonist-endostatin fusion proteins that inhibit angiogenesis to combat cancer. U.S. patent application Ser. No. 20010033948 by Chen entitled "Multimeric ligands with enhanced stability" teaches producing certain multimeric growth hormone and prolactin receptor agonist proteins of enhanced stability. U.S. patent application Ser. No. 20030022833 by Chen et al. entitled "Use of anti-prolactin agents to treat proliferative conditions" teaches variant forms of human prolactin which act as antagonists of the prolactin receptor, and to the use thereof to treat proliferative disorders. U.S. patent application Ser. No. 20020068043 by Chen et al. entitled "Bi-functional cancer treatment agents" teaches a human prolactin antagonist-interleukin 2 (hPRLA-IL-2) fusion protein to treat breast or prostate cancer. U.S. patent application Ser. No. 20010036662 by Walker et al. entitled "Prolactin antagonists an uses thereof" teaches recombinant PRL phosphomimetic and polynucleotides encoding same for certain therapeutic applications. The journal publication by Goffin et al, entitled "Development and potential clinical uses of human prolactin receptor antagonists" in *Endocrine Reviews*, published Apr. 6, 2005 teaches the use of various recombinant PRL-R antagonists, such as S179D-PRL, G129R-PRL, Δ1-9-G129R-PRL, G120K-GH, and G120R-

PL for certain clinical applications. The aforementioned prior art references are incorporated by reference as though fully set forth herein.

By way of example only, and without intending to limit the scope of PRL-R antagonists that may be used in the present embodiments to those set forth herein, the PRL variants S179D-PRL, G129R-PRL, Δ1-9-G129R-PRL may be suited for use in certain embodiments. Additionally, variants of other polypeptides, such as, for example, G120K-GH, G120R-PL, have been shown to function as either full or partial PRL-R antagonists (Goffin et al., 2005). In some embodiments, PRL variants that have been chemically modified such that the variants retain their ability to bind PRL-R but whose receptor binding fails to initiate signaling though the receptor may be suitable for use in the embodiments described herein. U.S. patent application Ser. No. 2004/0136952 entitled "Polymer conjugates of cytokines, chemokines, growth factors, polypeptide hormones and antagonists thereof with preserved receptor-binding activity" by Bhaskaran et al., which is incorporated by reference as though fully set forth herein, describes methods of generating PRL-R antagonists by conjugating certain water-soluble polymers thereto.

While the aforementioned PRL-R antagonists are suitable for use in the embodiments presented herein, it will of course be understood by an ordinary practitioner of the art that any compound or composition that interferes with PRL signaling in sensory neurons may be used during practice of the presently disclosed embodiments without departing from the spirit and scope thereof. Determining the effect that particular compound or composition has on PRL signaling, and determining whether the compound behaves as a full or a partial antagonist, is within the skill level of an ordinary practitioner of the art.

A PRL variant may be prepared using any suitable art-recognized technique to generate mutant polypeptides and/or polynucleotides. The design and production of variant polynucleotides and/or polypeptides is a well developed art and is well within the skill level of the ordinary practitioner. For illustrative purposes only, some non-limiting examples of techniques that may be used to generate mutant nucleic acids and/or proteins may include random mutagenesis techniques such as chemical mutagenesis, error-prone polymerase chain reaction, random deletion or random insertion techniques. Techniques for generating mutations in polypeptides or polynucleotides may also include site-directed mutagenesis techniques. Site-directed mutagenesis is a well-developed art. Site-directed mutagenesis may include the use of experimental techniques such as polymerase chain reaction. Site-directed mutagenesis may also be performed using one of several commercially available kits designed for this purpose. Non-limiting examples of commercially available kits that may be used to perform site-directed mutagenesis include the Sculptor IVM Mutagenesis Kit (from Amersham), Muta-Gene In Vitro Mutagenesis Kits (from Bio-Rad), TRANS-FORMER™ Site-Directed Mutagenesis Kit (from CLON-TECH), Morph Site-Directed Mutagenesis Kit (from 5 Prime→3 Prime), Mutan-Super Express-Km Kit (from Pan Vera), Unique Site Elimination (USE) Mutagenesis Kit (from Pharmacia Biotech), Altered Sites II In Vitro Mutagenesis Systems or Altered Sites II Mammalian In Vitro Mutagenesis Systems, Interchange In Vivo Amber suppression Mutagenesis System (from Promega), In Vitro Site-Directed Mutagenesis System (from GeneEditor), Quant-Essential Site Directed Mutagenesis Kits (from Quantum Biotechnologies), QUIKCHANGE® Site-Directed Mutagenesis Kit (from Stratagene), ExSite PCR-Based Site Directed Mutagenesis Kit (from Excite), Chameleon Double-Stranded Site-Directed Mutagenesis Kit (from Chameleon), CODE 20™ Kit (from New England BioLabs).

In another non-limiting embodiment, a PRL-R antagonist may be linked to another protein as part of a fusion protein. Linking the PRL variant to a fusion protein may facilitate production and purification of the fusion protein. Some exemplary, though non-limiting, fusion proteins that may be suitable for use herein include GST, MBP, lacZ, GAL4, any of several fluorescent fusion proteins, including GFP, YFP, CFP or RFP, epitope tags, or variants or portions thereof. Alternatively, the protein to which the PRL variant is fused may be chosen such that the PRL variant is preferentially targeted to particular tissue or cell in the body. By way of non-limiting example, it is known in the art that the RET receptor tyrosine kinase co-receptor, GFRα3, is preferentially expressed on VR1-expressing sensory neurons of the dorsal root ganglion. In one embodiment, a fusion protein may be made between arteminiinn, a natural ligand for GFRα3, and a prolactin antagonist. Administering to a subject an artemin-PRL-A fusion protein may result in a substantial portion of the PRL-R antagonist being targeted to pain neurons. Such embodiments may be advantageous in situations where it is undesirable to administer to a subject a compound that may disrupt PRL signaling systemically. Techniques for creating fusion proteins are widely known by ordinary practitioners of the art.

In an embodiment, a PRL-R antagonist may be targeted to nociceptors by coupling the PRL-R antagonist to a factor that is itself targeted to sensory neurons. For example, a PRL-R antagonist may be coupled to a molecule that is a ligand for a receptor expressed on sensory neurons, such as nerve growth factor (NGF). By way of another non-limiting example, a PRL-R antagonist may be coupled to capsaicin, a ligand for TRPV1, to create a bifunctional compound that has the ability to antagonize PRL signaling and bind preferentially to TRPV1-expressing sensory neurons. In one embodiment, a PRL-R antagonist may be targeted to sensory neurons by coupling the PRL-R antagonist to an antibody that binds specifically to a protein that is expressed on the surface of sensory neurons, such as, for example, TRPV1, peripherin, RET, or trkA. Methods for coupling molecules to polypeptides are widely known in the art and are within the skill level of ordinary practitioners of the art.

The present embodiments provide for methods whereby a PRL variant (which acts as a PRL-R antagonist) may be used to inhibit the effects of PRL, and in particular, may be used to inhibit PRL signaling in pain neurons. The methods contemplated herein include the administration of a prolactin antagonist, as part of a pharmaceutically acceptable formulation, to a subject having a pain disorder. By administering said PRL-R antagonists to the subject, signaling by at least a portion of PRL-R that are expressed on the surface of sensory neurons may be disrupted.

While the present embodiments are not limited to any particular methods of producing PRL-R antagonists for use herein, PRL-R antagonists will be typically be produced using recombinant protein production techniques. Recombinant protein production is well known in the art and is outlined briefly below.

Bacterial Expression

Useful expression vectors for use in bacteria are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may, also be employed as a matter of choice.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., USA), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia).

These "backbone" sections are combined with an appropriate promoter and the structural sequence to be expressed. Bacterial promoters include lac, T3, T7, lambda PR or PL, trp, and ara. T7 is the preferred bacterial promoter Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Eukaryotic Expression

Various mammalian cell culture systems may also be employed to express recombinant protein. Examples of mammalian expression systems include selected mouse L cells, such as thymidine kinase-negative (TK) and adenine phosphoribosul transferase-negative (APRT) cells. Other examples include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-1. Exemplary mammalian vectors include pWLneo, pSV2cat, pOG44, pXT1, pSG (Stratagene) pSVK3, pBPV, pMSG, and pSVL (Pharmacia). In a preferred embodiment, the mammalian expression vector is pUCIG-MET. Selectable markers include CAT (chloramphenicol transferase).

In mammalian host cells, a number of viral-based expression systems may be utilized. In cases where an adenovirus is used as an expression vector, the coding sequence of interest may be ligated to an adenovirus transcription/translation control complex, e.g., the-late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (E.g., See Logan et al., 1984, Proc. Natl. Acad. Sci. USA 81:3655-3659).

Gene Therapy Applications

The present embodiments also provide for compositions that allow for the local production of a PRL-R antagonist in a tissue of interest. In one embodiment, a cDNA that encodes a PRL-R antagonist may be inserted into an appropriate expression vector system. The expression vector may then be provided to a host cell. Expression of the PRL-R antagonist by the host cell may provide a long-term source of PRL-R antagonist that acts in an autocrine or paracrine manner to locally disrupt PRL signaling in pain neurons. Transfer of expression vectors to targeted cell populations may be performed using methods such as those employed in gene therapy protocols. Conventional viral and non-viral based vector and delivery systems may be used to deliver nucleic acids encoding PRL-R antagonists into cells or target tissues. In some embodiments, nucleic acids encoding PRL-R antagonists may be delivered for in vivo (e.g., to target tissues) or ex vivo (e.g., to cultured cells) gene therapy applications. Non-viral vector delivery systems include DNA plasmids, naked nucleic acid, and nucleic acid and in combination with a means of delivering the vector to a host cell.

Viral vector delivery systems include DNA and RNA viruses, which have either episomal or integrated genomes after delivery to the cell. The use of RNA or DNA viral based systems for the delivery of nucleic acids encoding PRL-R antagonists may take advantage of highly evolved processes for targeting a virus to specific populations of cells or tissues in the body and trafficking the viral payload to the nucleus. Viral vectors may be administered directly to patients (in vivo) or they may be used to treat cells in vitro and the modified cells are administered to patients (ex vivo). Conventional viral based systems for the delivery of PRL-R antagonists may include retroviral, lentivirus, adenoviral, adeno-associated and herpes simplex virus vectors. Viral vectors are currently the most efficient and versatile method of gene transfer in target cells and tissues. Integration in the host cell genome is possible with the retrovirus, lentivirus, and adeno-associated virus (AAV) gene transfer methods, often resulting in long term expression of the inserted transgene. Additionally, high transduction efficiencies have been observed in many different cell types and target tissues.

The tropism of a retrovirus may be altered by incorporating foreign envelope proteins and expanding the potential target population of target cells. Lentiviral vectors are retroviral vector that are able to transfect or infect quiescent (e.g., non-proliferating) cells. Lentiviral vectors typically result in high viral titers. Selection of a retroviral gene transfer system therefore depends on the properties of the target tissue and host cell. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those viral vectors that are derived from murine leukemia virus (MuLV), gibbon ape leukemia virus (GaLV), Simian Immuno deficiency virus (SIV), human immuno deficiency virus (HIV), and/or combinations thereof (see, e.g., Buchscher et al., 1992; Johann et al., 1992; Sommerfelt et al., 1990; Wilson et al., 1989; Miller et al., 1991; PCT/US94/05700).

In those embodiments where transient expression of PRL-R antagonists is desirable, adenoviral-based vector systems may typically be used. Adenoviral-based vectors are capable of high transduction efficiency in a wide variety of both proliferating and quiescent cell types and tissues, and also typically produce recombinant virus with high titers. Adenoviral vectors may be generated in large quantities using methods that are widely known in the art.

AAV vectors may also be used to transfect cells with polynucleotides encoding PRL-R antagonists. Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:20372-2081 (1984); Hermonat & Muzyczka, PNAS 81:6466-6470 (1984); and Samulski et al., J. Virol. 63:03822-3828 (1989), which are incorporated herein by reference.

Recombinant adeno-associated virus vectors (rAAV) are promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transfected cell are key features for this vector system. (Wagner et al., Lancet 351:9117 1702-3 (1998), Kears et al., Gene Ther. 9:748-55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transfect multiple types of tissues in vivo, including quiescent, differentiated cells such as those found in the liver, kidney and muscle system tissues. Conventional Ad vectors are typically able to accommodate large nucleic acid fragments. An example of the use of an Ad vector in a clinical trial involved polynucleotide therapy for antitumor immunization with intramuscular injection (Sterman et al., Hum. Gene Ther. 7:1083-9 (1998)).

Packaging cell lines are used to produce viral particles that are capable of transfecting a host cell. Exemplary packaging cell lines include, but are not limited to, 293 cells, which package adenovirus, and Ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it may be desirable to design a vector that may be delivered with a high degree of specificity to a particular cell or tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus may be modified to express human heregulin fused to gp70, and the recombinant virus is substantially targeted to only those human breast cancer cells that express human epidermal growth factor receptor. This principle may be extended to other viruses expressing a ligand fusion protein and target cell expressing a receptor. For example, filamentous phage may be engineered to express antibody fragments (e.g., FAB or Fv) having specific binding affinity for virtually any chosen cellular receptor. Although the above description applies primarily to viral vectors, the same principles may also be applied to non-viral vectors. Such vectors may be engineered to include specific uptake or targeting sequences that favor uptake by or delivery to specific target cells or tissues.

Some vectors may be delivered in vivo by administration to an individual patient, typically by systemic administration (e.g., intravenous, intraperitoneal, intramuscular, subdermal, or intracranial infusion) or topical application, as described below. Alternatively, vectors may be delivered to cells ex vivo, such as cells explanted from an individual patient (e.g., lymphocytes, bone marrow aspirates, some stem cells, tissue biopsy) or universal donor hematopoietic stem cells. Transfected cells may then be reimplantated into a patient. Populations of transfected cells may undergo one or more rounds of selection, to ensure that the cells that have incorporated the vector are enriched. Those cells that have been transfected with viral or non-viral vectors may be cryogenically preserved to use at a later date. Methods of cryogenic preservations are widely known to practitioners of the art.

Ex vivo cell transfection for diagnostics, research, or for gene therapy (e.g., via re-infusion of the transfected cells into the host organism) is well known to those of skill in the art. In an embodiment, cells are isolated from the subject organism, transfected with a polynucleotide containing coding regions for at least a portion of a PRL-R antagonist, and re-introduced back into the subject organism (e.g., patient). Various cell types suitable for ex vivo transfection are known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, adult or embryonic stem cells may be used in ex vivo procedures for cell transfection and gene therapy. The advantage to using stem cells is that they may be differentiated or induced to differentiate, into other cell types in vitro, or may be introduced into the subject (such as the donor of the cells) where they may engraft in tissues such as the bone marrow.

Stem cells may be isolated for transduction and differentiation using known methods. For example, stem cells may be isolated from bone marrow cells by selectively removing unwanted cells in the bone marrow using immunological methods such as "panning". Panning bone marrow cell suspensions with, for example, antibodies specific for cell surface receptors such as CD4+, CD8+, CD45+(panB cells), GR-1 (granulocytes), and Iad (differentiated antigen presenting cells) (see Inaba et al., J. Exp. Med. 176:1693-1702 (1992)), may selectively remove those cells that express CD4, CD8, CD45, GR-1 and Iad from the bone marrow suspensions and enrich the suspensions for adult bone marrow stem cells.

102111 Vectors (e.g., retroviruses, adenoviruses, liposomes, etc.) containing PRL-R antagonist coding regions may be also administered directly to the organism to transfect cells in vivo. Alternatively, naked DNA may also be administered. Administration is by any of the routes normally used for introducing a molecule into ultimate contact with blood or tissue cells. Suitable methods of administering such nucleic acids are available and well known to those of skill in the art and are discussed above. Additionally, it would be readily recognized by an ordinary practitioner of the art that more than one route can be used to administer a particular vector, and that some routes may provide a more immediate and more effective delivery than other routes.

Additional PRL-R Antagonists

While disclosure of the aforementioned PRL-R antagonists, the structures of which are related to but distinct from that of a naturally occurring PRL-R ligand, serve only as illustrative examples by which a practitioner may disrupt PRL signaling in pain neurons, it will readily be understood by an ordinary practitioner of the art that the embodiments described above are not restricted to the use of such antagonists. On the contrary, any molecules exhibiting PRL-R antagonist activity, the structures of which may be unrelated to that of PRL, GH or PL, may equally be applied to the embodiments described herein. The determination of whether a particular chemical compound behaves as a selective, broad or partial antagonists, and whether it is selective for particular subsets of PRL-R in cells or tissues is within the skill level of an ordinary practitioner of the art. Additionally, the determination of the effective dose of an antagonist that must be provided to the receptor in order to at least partially inhibit signaling from the receptor is within the skill level of an ordinary practitioner of the art. Examples of such methods are disclosed in U.S. Pat. No. 5,759,785 to Tsai et al. entitled "Method of identifying hormone antagonists and agonists". Furthermore, high throughput screening (HTS) technologies may be employed to identify novel small molecule or peptide compounds that act to disrupt PRL signaling in pain neurons. Illustrative, though non-limiting, examples of HTS technologies that may be used for such purposes are described in U.S. Pat. No. 6,387,879 to Blume et al. entitled "Compounds that bind growth to hormone receptor," which discloses methods for using peptides that bind to the active site of the growth hormone receptor to identify novel small molecule agonists/antagonists of the growth hormone receptor. The aforementioned references are fully incorporated herein by reference.

Additionally, it will be readily appreciated by a practitioner of ordinary skill in the art that additional selective PRL antgonists pharmacophores may be developed using, for example, rational design methodologies, such as is described, for example, in U.S. patent application Ser. No. 2004/0110154 entitled "Method for creating specific, high affinity nuclear receptor pharmaceuticals." U.S. Patent Application No. 2005/0004766 by Rarmnarayan et al, entitled "Use of computationally derived protein structures of genetic polymorphisms in pharmacogenomics for drug design and clinical applications" discloses computer-based methods for generating and using three-dimensional (3-D) structural models of target biomolecules for use in structure-based drug design methods to identify drugs that bind to particular structural variants, for designing allele-specific drugs, population-specific drugs and for predicting clinical responses in patients. The aforementioned references are also fully incorporated herein by reference.

Treatment Methods:

The embodiments described herein accordingly provide for compositions comprising a PRL-R antagonist in a suitable pharmaceutical carrier for use in the presently described methods. Such compositions may be administered by any suitable technique known to ordinary practitioners of the art, including but not limited to local application, intravenous, intraarterial, intrathecal, intraperitoneal, oral, etc.

Pharmaceutical compositions suitable for use in the present embodiments include compositions containing a PRL-R antagonist in an effective amount to achieve its intended purpose. More specifically, an effective dose refers to that amount of PRL-R antagonist required to substantially inhibit PRL signaling in sensory neurons. In some embodiments, an effective dose generally refers to the dosage of PRL-R antagonist that substantially inhibits or reverses the increased sensitivity to activating stimuli of sensory neurons exposed to estradiol and/or PRL. Determination of amounts or PRL-R antagonist required to achieve this effect is well within the capability of those skilled in the art. General guidance in determining effective dose ranges for pharmacologically active compounds may be found, for example, in the publications of the International Conference on Harmonisation and in REMINGTON'S PHARMACEUTICAL SCIENCES, chapters 27 and 28, pp. 484-528 (Mack Publishing Company 1990).

Effective concentrations of the compounds for use in presently described embodiments may be established experimentally in cell culture systems. The effective dose may be determined using a variety of different assays. For example, in vitro assays may be performed to determine the concentration of a PRL-R antagonist that is required to effectively compete the activity of a known amount of wild-type PRL.

The amount of the composition will, of course, also be dependent on the subject being treated, the pain disorder being treated, the severity of the pain disorder and the judgment of the prescribing physician. In some instances it may be necessary to adjust the treatment to a lower dose due to undesirable side effects as well as adjusting the treatment to higher levels if the clinical response is not adequate.

During the course of treatment of a pain disorder, the PRL-R antagonist may be administered either in isolation or as part of a sequential or combined treatment regimen. By way of nonlimiting example, where the pain disorder to be treated is trigeminal neuralgia, additional analgesic agents used to treat the disorder in a combined regimen may include carbamazepine (Tegretol), phenytoin (Dilantin), baclofen, gabapentin (Neurontin), Trileptol and Klonazepin.

Therapeutic Compositions:

The PRL-R antagonists of the presently disclosed embodiments may be formulated using art-recognized methods, or modifications thereof, to prepare pharmaceutically useful compositions, whereby the therapeutically active compounds or compositions are combined in admixture with a pharmaceutically acceptable carrier vehicle. Suitable vehicles and their formulation, inclusive of other human proteins, e.g., human serum albumin, are described, for example, in Remington's Pharmaceutical Sciences (16.sup.th ed., Osol, A., Ed., Mack, Easton Pa. (1980)). In order to form a pharmaceutically acceptable composition suitable for effective administration, such compositions will contain an effective amount of one or more of the proteins of the presently disclosed embodiments, together with a suitable amount of carrier vehicle.

Pharmaceutical compositions for use in accordance with the present embodiments may be formulated in conventional manner using one or more physiologically acceptable carriers or excipients. Thus, the PRL-R antagonists, or variants thereof, and their physiologically acceptable salts and solvate may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate Preparations for oral administration may be suitably formulated to give controlled release of the active compound. For buccal administration the composition may take the form of tablets or lozenges formulated in conventional manner.

The PRL-R antagonists may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, PRL-R antagonist molecules may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Therapy to Reduce PRL or PRL-R Gene Expression

In an alternate set of embodiments, compositions suitable for use in the practice of the embodiments described herein may include compositions that are capable of inhibiting or decreasing the biological availability (e.g., expression) of PRL and/or PRL-R in pain neurons. By inhibiting or decreasing the biological availability of PRL and/or PRL-R according to these embodiments, disruption of PRL signaling in pain neurons may be realized. In certain embodiments, inhibiting or decreasing the biological availability of PRL and/or PRL-R may include reducing the expression of PRL and/or PRL-R in pain neurons. Methods for reducing the expression of proteins are widely known in the art and include techniques such as antisense, ribozyme and RNAi technologies. In some embodiments, suitable compositions capable of inhibiting or decreasing the biological availability of PRL and/or PRL-R in pain neurons may include compositions for use in RNA interference (RNAi).

RNA interference (RNAi) is an art-recognized term used in reference to the biological phenomenon of double-stranded RNA-dependent sequence specific posttranscriptional gene silencing. Initial attempts to harness this phenomenon to manipulate gene expression in mammalian cells were foiled by a robust and nonspecific antiviral defense mechanism activated in response to long dsRNA molecules. The field was significantly advanced upon the demonstration that synthetic duplexes of 21 nucleotide RNAs could mediate gene specific RNAi in mammalian cells, without invoking generic antiviral defense mechanisms (Elbashir et al. Nature 2001, 411:494-498; Caplen et al. Proc Natl Acad Sci 2001, 98:9742-9747). As a result, small-interfering RNAs (siRNAs) have become powerful tools to dissect gene function. The chemical synthesis of small RNAs is one avenue that has produced promising results. DNA-based vectors capable of generating such siRNA within cells have also been developed. Several groups have recently attained this goal and published similar strategies that, in general, involve transcription of short hairpin (sh)RNAs that are efficiently processed to form siRNAs within cells (Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553). These reports describe methods to generate siRNAs capable of specifically targeting numerous endogenously and exogenously expressed genes.

The double-stranded duplex structure of siRNAs may be formed by a single self-complementary nucleic acid strand or two complementary nucleic acid strands. Duplex formation may be initiated either inside or outside the cell. The RNAi construct may be introduced in an amount that allows delivery of at least one copy per cell. Higher doses (e.g., at least 5, 10, 100, 500 or 1000 copies per cell) of double-stranded material may yield more effective inhibition, while lower doses may also be useful for specific applications. Inhibition of gene expression by RNAi is sequence-specific in that nucleotide sequences corresponding to the duplex region of the RNAi construct determine which gene whose expression will be silenced.

In certain embodiments, subject RNAi constructs are siRNA duplexes. These nucleic acids include an antisense RNA strand that is around 19-30 nucleotides in length, and typically 21-23 nucleotides in length, e.g., corresponding in length to the fragments generated by nuclease "dicing" of long double-stranded RNAs. siRNAs may include a sense strand that is RNA or DNA. The siRNAs are understood to recruit nuclease complexes and guide the complexes to the target mRNA by pairing to the specific sequences. As a result, the target mRNA is degraded by the nucleases in the protein complex.

The RNAi constructs embodied herein may be obtained using a number of techniques known to those of skill in the art. For example, the siRNA may be chemically synthesized or produced using recombinant techniques known in the art. In one embodiemnt, short sense and antisense RNA or DNA oligomers may be synthesized and annealed to form double-stranded structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures may then be introduced into cells, either by passive uptake or a delivery system of choice.

In certain embodiments, an RNAi construct may take the form of a hairpin structure. The hairpin may be synthesized exogenously or may be formed in vivo using a vector containing a targeting sequence flanked by RNA polymerase III promoters. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52. In some embodiments, such hairpin RNAs may be engineered in cells or in an animal to ensure continuous and stable suppression of a desired gene. It is known in the art that siRNAs can be produced by processing a hairpin RNA in the cell. A hairpin may be chemically synthesized such that a sense strand comprises RNA or DNA, while the antisense strand comprises RNA. In such an embodiment, the single strand portion connecting the sense and antisense portions should be adapted so as to be cleavable by nucleases in vivo, and any duplex portion should be susceptible to processing by nucleases such as Dicer.

RNAi constructs embodied herein may be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, or affinity purification may be used.

In certain embodiments, at least one strand of the double stranded siRNA molecules has a 3' overhang from about 1 to about 6 nucleotides in length, or from 2 to 4 nucleotides in length. In certain embodiments, the 3' overhangs are 1-3 nucleotides in length. In other embodiments, one strand has a 3' overhang and the other strand is blunt-ended or also has an overhang. The length of the overhangs may be the same or different for each strand. In order to further enhance the stability of the siRNA duplex, the 3' overhangs may be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In some embodiments, the one or more nucleotides of the RNAi construct may be chemically-modified. Examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various RNAi constructs, are shown to preserve RNAi activity in cells while advantageously increasing the stability of these compounds in the serum.

In one embodiment, the incorporation of modified nucleotides in RNAi constructs may improve in vitro or in vivo characteristics of the construct such as stability, activity, and/or bioavailability. An RNAi construct may include modified nucleotides as a percentage of the total number of nucleotides present in the construct. In some embodiments, an RNAi construct may include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given RNAi construct may depend on the total number of nucleotides present in the RNAi construct The specific sequence utilized in the design of the RNAi construct may be any contiguous sequence of nucleotides contained within the expressed gene message of the target (e.g., of PRL or PRL-R). Programs and algorithms, known in the art, may be employed to help in the selection of appropriate target sequences. In addition, optimal sequences may be selected utilizing programs designed to predict the secondary structure of a specified single stranded nucleic acid sequence and allow selection of those sequences likely to occur in exposed single stranded regions of a folded mRNA. Guidance in designing appropriate oligonucleotides for use in RNAi applications may be found in, for example, U.S. Pat. No. 6,251,588, the contents of which are incorporated herein by reference. mRNA is generally thought of as a linear molecule that contains the information for directing protein synthesis within the sequence of ribonucleotides. However, studies have revealed a number of secondary and tertiary structures exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three-dimensional structure. A number of researchers have measured the binding energies of a large number of RNA duplex structures and have derived a set of rules which can be used to predict the secondary structure of RNA (see e.g., Jaeger et al., (1989) Proc. Natl. Acad. Sci. (USA) 86:7706 (1989); and Turner et al., (1988) Ann. Rev. Biophys. Biophys. Chem. 17:167). The rules are useful in identification of RNA structural elements and, in particular, for identifying single stranded RNA regions, which may represent preferred segments of the mRNA to target for silencing by RNAi, ribozyme or antisense technologies. Accordingly, particular segments of the mRNA target may be identified for design of the RNAi constructs.

By way of non-limiting example, the nucleotide sequence of the sense strand of certain siRNA duplexes that may be used according to some embodiments is set forth in Tables I and II (SEQ ID NOS: 1-48). It will be readily appreciated by an ordinary practitioner of the art however, that these sequences disclosed therein are not exhaustive and merely represent a portion of nucleotide sequences that may be used in the design of RNAi constructs for use in the present embodiments.

Delivery of RNAi Constructs to a Cell

RNAi constructs may be introduced into the cell in a number of different ways. For example, in one embodiment, the RNAi construct may be delivered to a cell by microinjection. Alternate methods of introducing nucleic acids into a cell include bombardment by particles coated with the RNAi construct, soaking the cell or tissue in a solution containing the RNAi construct, electroporation of cell membranes in the presence of the RNAi construct, liposome-mediated delivery of RNAi construct and transfection of the RNAi construct mediated by chemicals such as calcium phosphate, viral infection, transformation, and the like. The RNAi construct may be applied to the cell in combination with components that enhance RNA uptake by the cell, stabilize the annealed strands, or otherwise increase inhibition of the target gene. In the case of a cell culture or tissue explant, the cells may be incubated in a solution containing the RNAi construct in combination with a lipid-mediated transfection reagent; in the case of a whole animal or plant, the dsRNA is conveniently introduced by injection or perfusion into a cavity or interstitial space of an organism, or systemically via oral, topical, parenteral (including subcutaneous, intramuscular and intravenous administration), vaginal, rectal, intranasal, ophthalmic, or intraperitoneal administration. In some embodiments, the RNAi construct may be administered via an implantable extended release device.

In one embodiment, RNAi constructs may be administered to the central nervous system (CNS) or peripheral nervous system (PNS). Experiments have demonstrated the efficient in vivo uptake of nucleic acids by neurons. As an example of local administration of nucleic acids to nerve cells, Sommer et al., 1998, Antisense Nuc. Acid Drug Dev., 8, 75, describe a study in which a 15 mer phosphorothioate antisense nucleic acid molecule to c-fos is administered to rats via microinjection into the brain. Antisense molecules labeled with tetramethylrhodamine-isothiocyanate (TRITC) or fluorescein isothiocyanate (FITC) were taken up by exclusively by neurons thirty minutes post-injection. A diffuse cytoplasmic staining and nuclear staining was observed in these cells. As a non-limiting example of systemic administration of nucleic acid to neurons, Epa et al., 2000, Antisense Nuc. Acid Drug Dev., 10, 469, describe an in vivo mouse study in which beta-cyclodextrin-adamantane-oligonucleotide conjugates were used to target the p75 neurotrophin receptor in neuronally differentiated PC12 cells. Following a two week course of IP administration, pronounced uptake of p75 neurotrophin receptor antisense was observed in dorsal root ganglion (DRG) cells. In addition, a marked and consistent down-regulation of p75 was observed in DRG neurons. Additional approaches to the targeting of nucleic acid to neurons are described in Broaddus et al., 1998, J. Neurosurg., 88(4), 734; Karle et al., 1997, Eur. J. Pharmacol., 340(2/3), 153; Bannai et al., 1998, Brain Research, 784(1,2), 304; Rajakumar et al., 1997, Synapse, 26(3), 199; Wu-pong et al., 1999, BioPharm, 12(1), 32; Bannai et al., 1998, Brain Res. Protoc., 3(1), 83; Simantov et al., 1996, Neuroscience, 74(1), 39. RNAi constructs of the presently described embodiments are therefore amenable to delivery to and uptake by cells in the CNS and/or PNS.

The delivery of RNAi constructs embodied herein to cells of the nervous system may be provided by a variety of different strategies. Traditional approaches to deliver nucleic acids to the CNS include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Alternative approaches may include the use of various transport and carrier systems, for example through the use of conjugates and biodegradable polymers. Furthermore, gene therapy approaches, for example as described in Kaplitt et al., U.S. Pat. No. 6,180,613 and Davidson, WO 04/013280, may be used to express nucleic acid molecules in the CNS.

Alternatively, RNAi constructs may be supplied to a cell indirectly by introducing one or more vectors that encode both single strands of the RNAi construct (or, in the case of a self-complementary RNA, the single self-complementary strand) into the cell. Vectors used for this purpose typically contain 5' and 3' regulatory elements that facilitate transcription of the coding sequence. Single stranded RNA is transcribed inside the cell, and the double stranded RNA forms and attenuates expression of the target gene. Methods for supplying a cell with an RNAi construct by introducing a vector from which it can be transcribed are set forth in WO 99/32619 (Fire et al., published 1 Jul. 1999). A viral construct packaged into a viral particle would accomplish both efficient introduction of an expression construct into the cell and transcription of RNA encoded by the expression construct. Typical vectors and gene delivery systems that that may be used to deliver RNAi constructs to cells have been discussed extensively above.

TABLE 2

Nucleotide sequences of siRNA oligos directed against the Human PRL Receptor product (NCBI Accession No. NM00949)

| siRNA sequence | Sequence identifier |
| --- | --- |
| GGGCUUUCUGCCUUACUCACU | SEQ ID NO:1 |
| GGACUUCCUACCAAUUAUUCA | SEQ ID NO:2 |
| GGACGUGACUUACAUAGUUCA | SEQ ID NO:3 |
| GGAGCUGGCUGUGGAAGUAAA | SEQ ID NO:4 |
| GCCUACAUCCAGGACAGAAAU | SEQ ID NO:5 |
| GUUCGCUGCAAACCAGACCAU | SEQ ID NO:6 |
| GCAAACCAGACCAUGGAUACU | SEQ ID NO:7 |
| GUCCAGCGACCUUCAUUCAGA | SEQ ID NO:8 |
| GCGACCUUCAUUCAGAUACCU | SEQ ID NO:9 |
| GGCUGUCCUUUCUGCUGUCAU | SEQ ID NO:10 |
| GUCCUUUCUGCUGUCAUCUGU | SEQ ID NO:11 |
| GUUGGAGAAGGGCAAGUCUGA | SEQ ID NO:12 |
| GAAGGGCAAGUCUGAAGAACU | SEQ ID NO:13 |
| GGGCAAGUCUGAAGAACUACU | SEQ ID NO:14 |
| GCAAGVCUGAAGAACUACUGA | SEQ ID NO:15 |
| GGUGGAGUAUUUAGAAGUAGA | SEQ ID NO:16 |
| GUGGAGUAUUUAGAAGUAGAU | SEQ ID NO:17 |
| GGAGUAUUUAGAAGUAGAUGA | SEQ ID NO:18 |
| GGACCAGCAUCUAAUGUGAGU | SEQ ID NO:19 |
| GGCCAAUCCCUCCACAUUCUA | SEQ ID NO:20 |
| GGUCAUUGAGAAGCCAGAGAA | SEQ ID NO:21 |
| GAUCCUCUUACCACAAUAUUA | SEQ ID NO:22 |
| GGAGAUUCACAAGGUCAACAA | SEQ ID NO:23 |
| GGUGCAUUAUCAUUGCUACCA | SEQ ID NO:24 |
| GUGCCAGAUCCACAUGCUAAA | SEQ ID NO:25 |
| CCCAACUUCACUGCAACAUCA | SEQ ID NO:26 |

TABLE 2-continued

Nucleotide sequences of siRNA oligos directed against the Human PRL Receptor product (NCBI Accession No. NM00949)

| siRNA sequence | Sequence identifier |
| --- | --- |
| GUACGUGAAAUGCUCAAGAAU | SEQ ID NO:27 |
| GCAGCUGAUUCCAGAACAAAU | SEQ ID NO:28 |
| GAGGGACAAUGCCAAUAGGUA | SEQ ID NO:28 |
| GGGACAAUGCCAAUAGGUAUA | SEQ ID NO:30 |
| GGGACAGACGGAAAUGAAAUU | SEQ ID NO:31 |

TABLE 3

Nucleotide sequences of siRNA oligos directed against the Human PRL gene product (NCBI Accession No. NM000948).

| siRNA sequence | Sequence identifier |
| --- | --- |
| GGAAGAAACUUGAUAACUGAU | SEQ ID NO:34 |
| GAUCCUCCAAACCAAUCUAGU | SEQ ID NO:35 |
| GCCAGUAUGUCUUCCUGAAUA | SEQ ID NO:36 |
| GCCAAUAUCUGGGAAAGAGAA | SEQ ID NO:37 |
| GUCCCACUACAUCCAUAACCU | SEQ ID NO:38 |
| GCAAGCCCAACAGAUGAAUCA | SEQ ID NO:39 |
| GAAGCCUCUUCCUGGAAUGGU | SEQ ID NO:40 |
| GCAAACCAAACGGCUUCUAGA | SEQ ID NO:41 |
| GUCUCGCCUUUCUGCUUAUUA | SEQ ID NO:42 |
| GCUCCUGAAGUGCCGAAUCAU | SEQ ID NO:43 |
| GUGCCGAAUCAUCCACAACAA | SEQ ID NO:44 |
| GCCGAAUCAUCCACAACAACA | SEQ ID NO:45 |
| GCUAAGCCCACAUCCAUUUCA | SEQ ID NO:46 |
| GCCCACAUCCAUUUCAUCUAU | SEQ ID NO:47 |
| GGUGUAACAGGUCUCCUCUUA | SEQ ID NO:48 |

An RNAi construct may be administered in an amount that allows delivery of at least one copy per cell. The amount of RNAi construct administered to a cell, tissue, or subject depends on the nature of the cell, tissue, or subject, the nature of the target gene (in this case, PRL and/or PRL-R), and the nature of the RNAi construct, and may readily be optimized to obtain the desired level of gene inhibition. To attenuate gene expression in a single cell embryo, for example, at least about $0.8 \times 10^6$ molecules of RNAi construct are injected; more preferably, at least about $20 \times 10^6$ molecules of RNAi construct are injected; most preferably, at least about $50 \times 10^6$ molecules of RNAi construct are injected. The amount of RNAi construct injected into a single cell embryo is, however, preferably at most about $1000 \times 10^6$ molecules; more preferably, it is at most about $500 \times 10^6$ molecules, most preferably, at most about $100 \times 10^6$ molecules. In the case of administration of RNAi construct to a cell in culture or to cells in a tissue, by methods other than injection, for example by soaking, electroporation, or lipid-mediated transfection, the cells are preferably exposed to similar levels of RNAi construct in the medium. For example, 8-10 µL of cell culture or tissue may be contacted with about $20 \times 10^6$ to about $200 \times 10^6$ molecules of RNAi construct, or from about $100 \times 10^6$ to about $500 \times 10^6$ molecules of RNAi construct, for effective attenuation of gene expression.

The RNAi constructs of the present embodiments may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject RNAi constructs may also be provided in formulations that include including penetration enhancers, carrier compounds and/or transfection agents Representative United States patents that teach the preparation of such uptake, distribution and/or absorption assisting formulations which can be adapted for delivery of RNAi constructs, particularly siRNA molecules, include, but are not limited to, U.S. Pat. Nos. 5,108,921; 5,354,844; 5,416,016; 5,459,127; 5,521,291; 51543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, all of which are incorporated herein by reference.

The RNAi constructs of the present embodiments also encompass any pharmaceutically acceptable salts, esters or salts of such esters, or any other compound which, upon administration to an animal including a human, is capable of providing (directly or indirectly) the biologically active form of the RNAi construct.

Methods to Diagnose Pain Disorders

The embodiments described herein also allow for the diagnosis of pain disorders by a physician or other practitioners of the art. The finding that PRL exerts a dominant effect on sensitization of pain neurons further provides for the development and implementation of a rapid diagnostic test for pain disorders, whereby the levels of PRL and/or PRL mRNA in a biological sample may be determined and correlated with a disease state.

In one embodiment, elevated levels of PRL may be associated with the presence and/or severity of a pain disorder in a subject. Elevated levels of circulating PRL are observed clinically in subjects with certain disorders such as, for example, in patients with pituitary disease, pituitary tumors (e.g., prolactinomas), hypothalamic disease, hypothyroidism, kidney disease, cancer, and irritation or trauma of the chest wall. Elevated levels of circulating PRL may also be observed in subjects secondary to effects of certain medications such as, for example, estradiol supplementation, tricyclic antidepressants, metoclopramide, phenothiazines, butyrophenones, reserpine, methyldopa or $H_2$-blockers. In one embodiment, a physician may obtain a measure of the amount of PRL in a biological sample to determine whether a subject is suffering from a pain disorder. In some embodiments, measurements of PRL in biological samples may be used to assess the severity of pain being experienced by a subject or to monitor the effectiveness of a treatment being administered to a patient for a pain disorders. Non-limiting examples of pain disorders that may be diagnosed according to the embodiments described herein include trigeminal neuralgia, temporomandibular disorders, fibromyalgia, post-herpetic neuralgia, migraine, irritable bowel syndrome, and cancer pain.

PRL measurements may also be used to diagnose or assess pain secondary to infection and inflammation (e.g., odontogenic pain), musculoskeletal pain in the neck, hands, and hips, pain secondary to certain medical procedures such as oral surgery, periodontal treatment, or other acute and chronic pain conditions.

In one embodiment, diagnosing a pain disorder may begin by obtaining a biological sample from a subject suffering from such a disorder. Biological samples suitable for obtaining PRL measurements according to the embodiments described herein may include body fluids or tissue biopsies.

A variety of protocols for measuring PRL, including ELISA, RIA, and FACS, are known in the art and provide a basis for diagnosing altered or abnormal levels of PRL expression in a subject. Normal or standard values for PRL expression are established by combining body fluids or cell extracts taken from normal mammalian subjects, for example, human subjects, with antibodies to PRL under conditions suitable for complex formation. The amount of standard complex formation may be quantitated by various methods, such as photometric means. Quantities of PRL present in a biological sample collected from a test subject, or from control individuals, may be compared with the standard values. Deviation between standard and subject values establishes the parameters for diagnosing disease. Typically, for example, the amount of PRL present in the serum of adult males, or adult non-pregnant females is in the range of about 0 to about 20 ng/ml. In pregnant females, serum PRL concentrations in the range of about 10 to about 300 ng/ml are typically seen.

In an alternate embodiment, a physician may wish to diagnose a pain disorder in an individual by obtaining a measurement of the local amount of PRL mRNA present in a tissue biopsy. In one embodiment, a biopsy of a sensory ganglion may be collected, and the amount of PRL mRNA present in the biopsy may be determined. The determination of the amount of a specific mRNA specified in a tissue sample is within the skill level of an ordinary practitioner of the art, and may include the use of techniques such as quantitative RT-PCR or nucleic acid hybridization techniques. The diagnostic tests described herein may be used to determine absence, presence, and excess expression of PRL, and to monitor regulation of PRL levels during therapeutic intervention.

In order to provide a basis for the diagnosis of a disorder associated with expression of PRL mRNA, a normal or standard profile for the expression is established. This may be accomplished by combining body fluids or cell extracts taken from normal subjects, either animal or human, with a sequence, or a fragment thereof, encoding PRL, under conditions suitable for hybridization or amplification using quantitative RT-PCR techniques. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, the diagnostic methods described herein may be repeated on a regular basis to determine if the level of PRL protein or PRL mRNA in subject-derived biological samples begins to approximate that which is observed in the normal subject. The results obtained from successive assays may be used to show the efficacy of treatment over a period ranging from several days to months.

EXAMPLES

The following will serve to illustrate, by way of one or more examples, systems and methods for inhibiting, reducing or otherwise disrupting prolactin signaling in pain neurons according to some embodiments. The examples below are non-limiting and are intended to be merely representative of various aspects and features of certain embodiments. Although methods and materials similar or equivalent to those described herein may be used in the application or testing of the present embodiments, suitable methods and materials are described below.

Materials and Methods

Animals: Adult ovariectomized (OVX) female Sprague-Dawley rats and intact females (200-250 g, Charles River, Wilmington, Mass., USA) were used in this study. All animal study protocols were approved by the Institutional Animal Care and Use Committee of the University of Texas Health Science Center at San Antonio and conformed to the International Association for the Study of Pain (IASP) and federal guidelines. Animals were housed for one week prior to the experiments with food and water available ad lib and the OVX rats were used 2-3 weeks after their surgery.

Determination of Reproductive Cycle: The reproductive stage of cycling females was determined by vaginal lavage using sterile isotonic saline at the same time each day for at least 3 consecutive cycles (approximately 12 days) using methods previously described (Marcondes et al., 2002). Animals that were at the proestrous reproductive cycle stage were immediately decapitated and TG were harvested and used for subsequent studies.

Materials: For in vivo studies, 17β-estradiol-3-benzoate (E2) (Sigma, St. Louis, Mo.) was dissolved in peanut oil (Sigma) at final concentrations to give systemic doses of 2, 20 or 80 μg/kg in a 200 μl injection volume. For in vitro studies, water soluble β-estradiol (E2) (Sigma) was dissolved in water and diluted in culture media (final concentration of 50 nM). Capsaicin (CAP) (Sigma) was dissolved in ethanol and diluted in saline for the behavioral studies, and diluted in buffer (Hanks or Standard External Solution-SES) for the in vitro studies. Ovine PRL [oPRL-21, BIO], kindly provided by Dr. A. F. Parlow (NHPP, Harbor-UCLA), was dissolved in 5 μM sodium bicarbonate solution and diluted into buffer (Hanks or SES) for the in vitro studies or diluted in saline for the behavioral experiments. The PRL receptor antagonist 1-9-ΔG129R-hPRL, was synthesized as described (Bernichtein et al., 2003; Goffin et al., 2005) and purified by HPLC; it was dissolved in 5 μM sodium bicarbonate solution and diluted in SES buffer.

Estradiol administration: Ovariectomized rats received a daily subcutaneous (s.c.) injection of 2, 20 or 80 μg/kg of 17-beta-estradiol 3-benzoate in peanut oil (200 μl), or vehicle, for 10 days. The 2, 20 or 80 μg/kg dose paradigms, generated plasma estradiol levels of 1.89±0.36, 59±17.1, and 110±36.6 pg/ml (mean±SEM, n=4/group) respectively (A. Diogenes and J. C. Fehrenbacher, unpublished observations). At the end of the $10^{th}$ day, animals were used for behavioral experiments or sacrificed by decapitation and the TG of each individual animal were harvested. Harvested tissue was used for RNA isolation, total protein isolation, or for preparing primary cultures of TG neurons.

RNA isolation: Harvested TG tissue from OVX (treated with vehicle or estradiol) or intact proestrous female rats were immediately frozen in liquid nitrogen and ground in a pre-chilled mortar. The ground tissue was used to isolate total RNA by the guanidinium thiocyanate method as described previously (Chomczynski and Sacchi, 1987). The isolated RNA was then treated with a DNA-free reagent (DNAse I; Ambion, Austin, Tex.) and submitted to the Microarray Core Facility at the University of Texas Health Science Center at San Antonio. Additional RNA sample aliquots were used as template for the quantitative real time RT-PCR experiments.

Microarray analysis: Target preparation, hybridization, staining, scanning and analysis of image: RNA samples derived from TG of OVX rats treated with a single dose (80 µg/kg per day) of E2 or vehicle (n=5 for each group) were prepared for hybridization to Affymetrix (Santa Clara, Calif.) RG-U34A arrays according to the manufacturer's instructions. Total RNA was used as a template for double-stranded cDNA synthesis (Superscript Double-Stranded cDNA Synthesis kit, Invitrogen, Carlsbad, Calif.), which was used as a template for biotin-labeled cRNA synthesis (Enzo BioArray High Yield RNA Transcription Labeling Kit, Affymetrix). Purified (RNeasy kit, Qiagen, Valencia, Calif.) labeled-cRNA was hybridized to the rat genomic RG-U34A GeneChips for 16 h at 45° C. Following hybridization, the probe arrays were washed and stained using the GeneChip Fluidics station protocol EukGE-ES2. The intensity of bound dye was measured with an argon laser confocal scanner (GeneArray Scanner, Agilent, Palo Alto, Calif.). The probe arrays were scanned twice and the stored images were aligned and analyzed using the GeneClip software Micro array Analysis Suite (MAS) 5.0 (Affymetrix, Santa Clara, Calif.). Data were imported into the GeneSpring 5.1 software (Silicon Genetics, Redwood City, Calif.) and a list of genes of relative expression of $\geq 1.5$ and $\geq 0.5$ fold was obtained. The data were imported into the R software package and the probe level data were converted to expression measures using the Affy package (Bolstad et al., 2003) from Bioconductor. Expression values for each mRNA were obtained by the Robust Multi-array Analysis (RMA) method as described elsewhere (Boistad et al., 2003). CEL files were normalized together and the expression values obtained were further analyzed with the Statistical Analysis of Microarrays (SAM) software (Tusher et al., 2001) to identify those genes that were significantly increased or decreased. Only those genes that were found to be changed in both the GeneSpring and SAM analyses (i.e., concordant increasers or decreasers) were considered for further analysis.

Quantitative Real Time RT-PCR (qRT-PCR): Total RNA (100 ng) was used as template in a one-step RT-PCR protocol. Amplification of target sequences was detected by a sequence detector ABI 7700 (Applied Biosystems, Foster City, Calif.) utilizing TaqMan Gene Expression Assays on Demand (Applied Biosystems, Foster City, Calif.) using specific primers and probes for the selected genes (PRL: assay #Rn00561791_m1; 12-Lipoxygenase: assay # Rn00578743_m1; TrkA: assay # Rn00572130_m1; Interleukin-1 alpha: assay # Rn00566700_m1; Nuclear receptor subfamily 1 group D member 1: assay # Rn00595671_m1; Eukaryotic 18S rRNA endogenous reference: assay # Hs99999901_s1).

The reactions were run in triplicates of 25 µl, containing the respective TaqMan Gene Expression Assay on Demand and TaqMan Universal PCR Master Mix (Applied Biosystems, Foster City, Calif.). For each individual gene expression assay, the endogenous control, 18S ribosomal subunit, gene expression assay was also run in triplicate. The comparative delta-delta Ct (ddCt) was utilized to normalize the data based on the endogenous reference, and to express it as the relative fold change after the exclusion criteria were verified by comparing primer efficiencies (Livak and Schmittgen 2001).

Rat trigeminal ganglia (TG) primary cultures: The TG from ovariectomized or intact female rats were quickly removed after decapitation and neuronal cultures were prepared as previously described (Fehrenbacher et al., 2005; Patwardhan et al., 2005). The trypsin treatment was omitted in TG cultures prepared for electrophysiological recording and $Ca^{2+}$ imaging. Cells were plated on 24 well Poly-D-Lysine coated plates (for iCGRP experiments), 6 well Poly-D-Lysine plates (for PRL release experiments), Poly-D-Lysine/laminin-coated coverslips (for single cell studies) or 10 cm plates (for phosphorylation experiments), respectively. The TG cultures were maintained at 37° C. and 5% $CO_2$. For the calcium imaging and electrophysiology experiments, cells were plated as 2 ganglia per plate and maintained for 2-8 h in culture media without NGF in the presence of either 50 nM water soluble estradiol or vehicle. For the CGRP and PRL release experiments, cells were plated at 6 ganglia per plate and grown for 5 days in culture in the presence of 100 ng/ml NGF (Harlan, Indianapolis, Ind.) and either 50 nM water soluble estradiol (Sigma, St. Louis, Mo.) or vehicle. The media were replaced at the end of 24 h and then 48 h later.

Immunohistochemistry: Rat tissue cryosections or cultured TG cells were fixed with 4% formaldehyde, permeabilized with 0.5% Triton X-100, and then blocked with 10% normal goat serum (30 min each step). Cells or tissue slides were then incubated overnight at 4° C. with a rabbit polyclonal antibody directed against PRL (1:5000), kindly provided by Dr. A. F. Parlow (NHPP, Harbor-UCLA) or mouse monoclonal anti-PRL-R antisera (1:500) (Clone U5, Affinity Bioreagents, Golden, Colo.) (De Petrocellis et al., 1998; Shingo et al., 2003) and a guinea pig anti-TRPV1 antisera (1:3000) (Neuromics, Bloomington, Minn.). Immunoreactivity was detected using an appropriate secondary antibody conjugated to Alexa-488 or Alexa-594 conjugated (1:500, Molecular Probes, Eugene, Oreg., USA). Images were acquired using a Nikon E600 microscope (Melville, N.Y., USA). Images were analyzed using Metamoph software (Version 4.5 r6, Universal Imaging Inc.) and the percentages of PRL and PRL-R co-localization with TRPV1 for each condition were determined by manual counting the number of cells with double labeling in a 20× magnification view field.

PRL Release Experiments: These experiments were performed at day 5 with TG cultures from OVX or intact female rats using Krebs buffer (NaCl 135 mM, KCl 3.5 mM, MgCl2 1 mM, NaH2PO4 1 mM, CaCl2 2.5 mM, BSA 0.1%, dextrose 3.3 mM, ascorbic acid 0.1 mM, HEPES 10 mM, thiorphan 16 µM; pH 7.4). After two initial washes, a 15 min baseline sample was collected. Cells were then exposed to 300 nM capsaicin (Sigma) or 25 mM KCl and incubated at 37° C. for an additional 15 min followed by collection of the samples. The 1 ml collected samples were lyophilized and resuspended in 250 ul of water and immediately frozen in −80° C. Frozen samples were sent to Dr. A. F. Parlow (NHPP, Harbor-UCLA) to have levels of PRL determined by a well-validated radio-immunoassay (RIA) with sensitivity range from 1-100 ng/ml. Results are representative of 6 independent experiments.

Calcium Imaging: TG cells cultured on coverslips were loaded with the cell-permeable calcium sensitive dye FURA 2-AM (1 ug/ml) (Molecular Probes, Eugene, Oreg.) for 30 min at 37° C. in Standard External Solution (SES) of the following composition in mM: 140 NaCl, 5 KCl, 2 $CaCl_2$, 1 $MgCl_2$, 10 glucose and 10 HEPES, pH 7.4. Coverslips containing cells were placed in a chamber with constant infusion of SES. Images were captured by a Nikon Eclipse TE-2000 microscope fitted with a 20×/NA 0.75 Fluor objective. Fluorescence images were collected in 5 sec intervals throughout the experiment, analyzed, and the $F_{340}/F_{380}$ ratio calculated by the Methafluor Software (MethaMorph, Web Universal Imaging Corporation, Downingtown, Pa.). Capsaicin was delivered locally to the cells, whereas PRL was delivered into the bath solution. The magnitude of calcium influx was determined by subtracting the averaged baseline 30 sec prior to the capsaicin stimulus from the peak achieved by the capsaicin stimulation for each cell (ratiometric method, $\Delta F_{340}/F_{380}$).

Patch Clamp Electrophysiology: All recordings were performed in whole-cell voltage-clamp ($V_h$=−60 mV) configuration. Recordings were acquired at 22-24° C. from the somata of neurons (15-45 pF) using an Axopatch200B amplifier and pCLAMP9.0 software (Axon Instruments, Union City, Calif.). Data were filtered at 0.5 kHz and sampled at 2 kHz. Borosilicate pipettes (Sutter, Novato, Calif.) were polished to resistances of 3-5 MΩ in pipette solution. Access resistance was compensated (40-80%) to 7-10 MΩ values when appropriate. Cell diameters were calculated using $d=\sqrt{[100*C_m/\pi]}$, where d (μm) is cell diameter and $C_m$ (pF) is membrane capacitance. Concentration-response curves were fitted to the Hill equation $I/I_{max}=1/[1+(EC_{50}/C)^h]$, where $EC_{50}$ is the half maximal effective concentration, C is the drug concentration, h is the Hill coefficient and $I_{max}$ is the maximum current.

Standard external solution (SES) had the composition as described above. The pipette solution had an estimated free $Ca^{2+}$ concentration of approximately 100 nM and consisted of (in mM): 140 KCl, 1 $MgCl_2$, 1 $CaCl_2$, 10 EGTA, 10 D-glucose, 10 HEPES, 0.2 Na-GTP and 2.5 Mg-ATP, pH 7.3. Drugs were applied using a fast, computer controlled pressure-driven 8-channel system (ValveLink8; AutoMate Scientific, San Francisco, Calif.).

For the recording of heat-activated currents ($I_{heat}$), SES was heated on-line by a Peltier device (Warner Instruments, Hamden, Conn.) and locally delivered via a glass tube positioned in close proximity to the neuron. Temperature values were acquired with a thermister probe (0.5-1.5 mm size; Harvard Apparatus, Holliston, Mass.) situated at the orifice of the glass tube for local delivery of heated SES. The thermister probe coupled to an Axopatch200B amplifier and pCLAMP9.0 was employed to register the temperature values simultaneously with heat-activated currents. $I_{heat}$ was generated from neurons treated with either PRL or vehicle delivered in the bath solution.

CGRP release assay: All culture experiments were performed on day 5 at 37° C. using modified Hanks (Gibco) buffer (10.9 mM HEPES, 4.2 mM sodium bicarbonate, 10 mM dextrose and 0.1% bovine serum albumin were added to 1× Hanks). After two initial washes, a 15 min baseline sample was collected. The cells then were exposed to either vehicle or PRL (NHPP, Harbor-UCLA) (40 nM) for 15 min and then stimulated with capsaicin (50 nM) for 15 min. All the treatments were collected for analysis of iCGRP content by radioimmunoassay (RIA).

iCGRP RIA: A previously used (Garry et al. 1994) primary antibody against CGRP (final dilution 1:1,000,000, kindly donated by Dr. Iadarola, NIH) was added in the tubes containing media from cultured rat TGs and incubated at 4° C. for 24 h. Then 100 μl of $[I^{-125}]$-$Tyr^0$-$CGRP_{28-37}$ (~20,000 CPM) and 50 μl of goat anti-rabbit antisera coupled to ferric beads (PerSeptive Diagnostics, Cambridge, Mass., USA) were added to these tubes. The tubes were incubated for another 24 h at 4° C. The assay was stopped using immunomagnetic separation of bound from free tracer. All compounds used in experiments were tested for interference with the RIA. The minimum detectable levels for CGRP for this assay are approximately 3 fmol and the 50% displacement at 28 fmol.

Immunoprecipitation and Western Blot Analysis: Total protein was isolated from harvested TG by tissue disruption in homogenization buffer consisting of 25 mM HEPES, 25 mM sucrose, 1.5 mM MgCl2, 50 mM NaCl, leupeptin (1 ug/ml), pepstatin (1 ug/ml), aprotinin (2 ug/ml), and PMSF (100 nm) (pH 7.2) using a pre-chilled mortar and pestle. Protein samples were resolved on 12.5% SDS-PAGE, transferred to PVDF (Millipore, Billerica, Mass.) and the Western blots were blocked in 5% BSA in TBS-Tw and visualized using antibodies to PRL (1:2500) (C-17, Santa Cruz Biotechonology, Inc.) or PRL receptor (PRL-R) (1:500) (Clone U5, Affinity Bioreagents)(De Petrocellis et al., 1998; Shingo et al., 2003) followed by appropriate secondary antisera linked to HRP and enhanced chemiluminescence (GE Healthcare, Piscataway, N.J.) following manufacturer's instructions.

For protein phosphorylation experiments, 10 cm plates of TG, grown for 4-8 h, were incubated with 1 mCi of $^{32}P$ orthophosphate (Perkin Elmer, Wellesley, Mass.) per plate for 4 h at 37° C. in phosphate-free DMEM. Plates were treated with 40 nM PRL or vehicle ($H_2O$) for 10 min, and prepared for harvesting. Following rigorous rinsing with 1×PBS and lysis in General Lysis buffer (1 mM sodium pyrophosphate, 50 mM HEPE (pH 7.5), 1% Triton X-100, 50 mM NaCl, 50 mM NaF, 5 mM EDTA (pH 8.0), 1 mM sodium orthovanadate, 1 μg/ml pepstatin, 1 μg/ml leupeptin, 100 nm PMSF), cleared lysates were immunoprecipitated with 1 μg of anti-TRPV1 (Calbiochem, San Diego, Calif.), and resolved on 15% SDS-PAGE, and transferred to PVDF (Millipore). Western blots were either exposed to film at −80° C. overnight for autoradiography, or visualized as described above using anti-TRPV1 antisera (Calbiochem, San Diego, Calif.).

Autoradiography and Western blot results were scanned and quantified using NIH Image 1.62. All autoradiographic bands were normalized to values obtained from total immunoprecipitated TRPV1. Results are representative of 3-4 independent experiments.

Eye-Wipe Test OVX female rats, treated with either vehicle or E2 (5μg/day/10 days), or intact female rats in the proestrous reproductive stage were brought to a quiet, temperature controlled (22-25° C.) behavioral laboratory in individual cages where they were allowed to acclimate for at least 2 h. PRL (1 μg/μl) or vehicle was placed directly onto the right eye in a volume of 40 ul followed by application of 0.01% (40 μl) capsaicin solution as described previously (Price et al. 2004). The resulting behavioral response was measured as time spent grooming or wiping the test eye. The observers were blinded to the treatments and the data were collected in 3 bins of 5 min.

Data analysis: All experiments were conducted with n=8 wells/group for culture experiments (CGRP, PRL release) and n=3-6 tissue samples/group for qRT-PCR and immunoblotting experiments to determine the experimental observation and then repeated at least 3 times to conduct the statistical analysis. Behavioral studies were conducted with n=6-8 rats/group. The iCGRP, PRL release and calcium influx data are presented as percent of basal levels (mean±SEM). Data were analyzed using GraphPad Prism software version 4 (GraphPad software Inc., San Diego, Calif., U.S.A.). The results were analyzed using one-way-ANOVA and individual groups were compared using a Bonferroni post-hoc test. Two factor multiple treatment data were analyzed by 2-way-ANOVA, whereas data comparing only two groups were analyzed using 2-tailed t test. The statistical significance was tested at p<0.05.

Example 1

Figure 10:
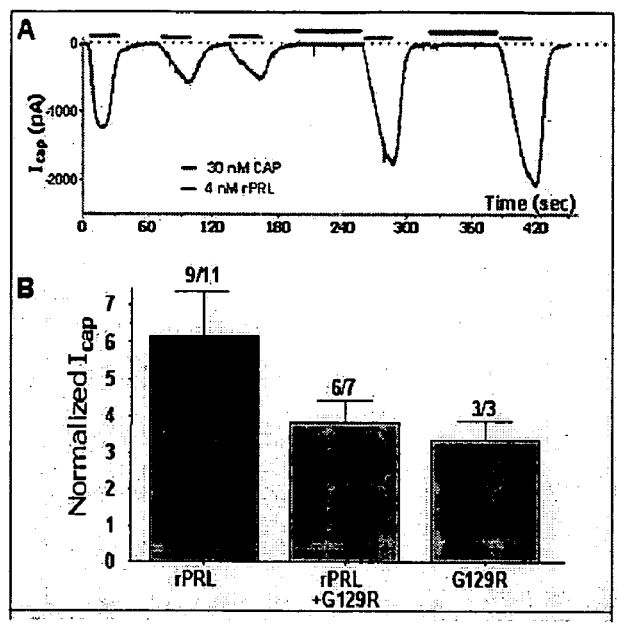
FIG 10A depicts a representative plot showing the effect of administering PRL, human G129R-PRL, or their combination, on Icap.
FIG. 10B depicts a histogram summarizing the effect of administering PRL, human G129R-PRL, or their combination, on Icap.

As was discussed above and depicted in FIG. 4C, application of the full PRL-R antagonist 1-9-Δ-G129R-hPRL significantly blocked the ability of PRL to sennsitize capsaicin-evoked $Ca^{2+}$ influx. Since it is possible that this effect is observed only in full PRL-R antagonists, it is of interest to determine the effectiveness of partial PRL-R antagonists in blocking PRL-mediated nociceptor sensitization. To this end, the ability of the partial PRL agonist (G129R-PRL) to inhibit PRL-induced increase in sensitivity to capsaicin was assessed. FIG. 10 summarizes the effect of administering PRL, human G129R-PRL, or their combination, on Icap. G129R-PRL acts as either a partial or full antagonist, depending on the cellular context of the experimental system (Goffin, Bernichtein et al. 2003). Co-application of G129R-PRL 16 nM with rPRL 4 nM reduced the PRL effect by about 40% and this effect was observed in 6 of 7 examined neurons. Moreover, application of G129R PRL in the absence of rPRL displayed partial agonist effects in this assay in 3 of 3 examined neurons. Furthermore, the data demonstrate that the PRL effect is mediated through the PRL-R, since co-application of a partial agonist (G129R-PRL) reduces the PRL effect to the level observed with the partial agonist alone; this is a classic pharmacological interaction observed with agonist and partial agonist interactions on receptors.

These results further support the role of PRL-signaling in nociceptor sensitization, and demonstrate that therapeutic applications that involve blocking or reducing PRL-R mediated signaling for the treatment of pain disorders is not restricted to full PRL-R antagonists.

Example 2

Figure 11:
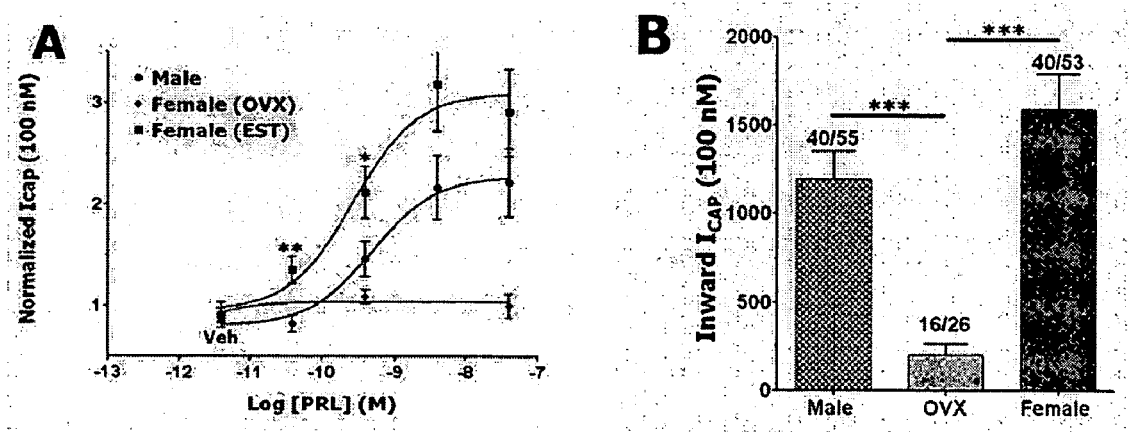
FIG. 11A depicts the effect on normalized Icap evoked by 100 nM capsaicin of exposing cultured TG neurons from OYX female, normal female and male rats to varying concentrations of recombinant human PRL (rhPRL)
FIG. 11B depicts a summary of the effect of adding rhPRL on Icap of cultured TG neurons from male, female and OVX female rats.

Turing now to FIG. 11, it can be seen that recombinant human PRL (rhPRL) is able to sensitize cultured neurons isolated from male and female TG neurons, and the magnitude of the response evoked by stimulating the neurons with 100 mM capsaicin is proportional to the concentration of rhPRL applied to the neurons. FIG. 11 A shows the effect on normalized Icap evoked by 100 nM capsaicin of exposing cultured TG neurons from OVX female (diamonds), normal female (square) and male (circle) rats to varying concentrations of recombinant human PRL (rhPRL). FIG. 11B summarizes the effect of adding rhPRL on Icap of cultured TG neurons from male, female and OVX female rats. Number of recorded neurons and neurons in which effects were observed are indicated above the bars. The recordings were performed in whole-cell voltage clamp c(Vh=−60 mV) configuration. Solutions are SES and SIS. It should be noted however, that while both male and female neurons exhibit dose-dependent increases in Icap in the presence of PRL, neurons derived from females (and thus exposed to higher levels of female sex steroids) show greater magnitude of response. These data yet further support the use inhibitor of PRL-signaling in the treatment of pain disorders in both genders.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

REFERENCES

The following references are incorporated herein by reference.

Abe, T., K. Matsumoto, et al. (1998). "Headache associated with pituitary adenomas." *Headache* 38: 782-6.

Ahonen, T. J., P. L. Harkonen, et al. (2002). "PRL signal transduction in the epithelial compartment of rat prostate maintained as long-term organ cultures in vitro." *Endocrinology* 143(1): 228-38.

Amadesi, S., J. Nie, et al. (2004). "Protease-activated receptor 2 sensitizes the capsaicin receptor transient receptor potential vanilloid receptor 1 to induce hyperalgesia." *J Neurosci* 24: 4300-12.

Amaral, M. E., D. A. Cunha, et al. (2004). "Participation of prolactin receptors and-phosphatidylinositol 3-kinase and MAP kinase pathways in the increase in pancreatic islet mass and sensitivity to glucose during pregnancy." *J Endocrinol* 183(3): 469-76.

Amaral, M. E., M. Ueno, et al. (2003). "Prolactin-signal transduction in neonatal rat pancreatic islets and interaction with the insulin-signaling pathway." *Horm Metab Res* 35(5): 282-9.

Asano, H., T. Muneta, et al. (2002). "Evaluation of clinical factors affecting knee pain after anterior cruciate ligament reconstruction." *The Journal of Knee Surgery* 15(1): 23-8.

Bakowska, J. C. and J. I. Morrell (2003). "The distribution of mRNA for the short form of the prolactin receptor in the forebrain of the female rat." *Brain Res Mol Brain Res* 116(1-2): 50-8.

Barsky, A. J., H. M. Peekna, et al. (2001). "Somatic symptom reporting in women and men." *Journal of General Internal Medicine* 16(4): 266-75.

Ben-Jonathan, N., K. Liby, et al. (2002). "Prolactin as an autocrine/paracrine growth factor in human cancer." *Trends Endocrinol Metab* 13(6): 245-50.

Bernabei, R., G. Gambassi, et al. (1998). "Management of pain in elderly patients with cancer. SAGE Study Group. Systematic Assessment of Geriatric Drug Use via Epidemiology." *Jama* 279(23): 1877-82.

Bernichtein, S., S. Kinet, et al. (2001). "S179D-human PRL, a pseudophosphorylated human PRL analog, is an agonist and not an antagonist." *Endocrinology* 142(9): 3950-63.

Bhatavdekar, J. M., D. D. Patel, et al. (2000). "Prolactin as a local growth promoter in patients with locally advanced tongue cancer: GCRI experience." *Head Neck* 22(3): 257-64.

Binart, N., P. Imbert-Bollore, et al. (2003). "A short form of the prolactin (PRL) receptor is able to rescue mammopoiesis in heterozygous PRL receptor mice." *Mol Endocrinol* 17(6): 1066-74.

Bole-Feysot, C., V. Goffin, et al. (1998). "Prolactin (PRL) and its receptor: actions, signal transduction pathways and phenotypes observed in PRL receptor knockout mice." *Endocr Rev* 19(3): 225-68.

Bonifacino, J. (1998). "Metabolic labeling with amino acids." *Curr. Protocols Mol. Biol Unit* 10: 18:10.18.11-10.18.10.

Bonnington, J. and P. McNaughton (2003). "Signalling pathways involved in the sensitisation of mouse nociceptive neurones by nerve growth factor." *J Physiol* 551: 433-46.

Borum, M. L. (2002). "Physician perception of IBS management in women and men." *Digestive Diseases & Sciences* 47(1): 236-7.

Bowsher, D. (1999). "The lifetime occurrence of Herpes zoster and prevalence of post-herpetic neuralgia: A retrospective survey in an elderly population." *European Journal of Pain: Ejp* 3(4): 335-342.

Brain, S., H. Cambridge, et al. (1991). "Evidence that calcitonin gene-related peptide contributes to inflammation in the skin and joint," *Ann. NY Acad. Sci* 112: 412-9.

Brain, S., H. Morris, et al. (1985). "Calcitonin gene-related peptide is a potent vasodilator." *Nature* 313: 54-56.

Brown, A. M., J. M. Janik, et al. (2004). "Effects of cyclic steroid hormone replacement on prolactin and luteinizing hormone surges in female rats." *Reproduction* 128(3): 373-8.

Bulayeva, N. N., A. L. Wozniak, et al. (2005). "Mechanisms of membrane estrogen receptor-{alpha}-mediated rapid stimulation of Ca2+ levels and prolactin release in a pituitary cell line." *Am J Physiol Endocrinol Metab* 288(2): E388-97.

Byers, M. and P. Taylor (1993). "Effect of sensory denervation on the response of rat molar pulp to exposure injury." *J Dent Res* 72: 613-8.

Carlsson, G. and L. LeResche (1995). *Epidemiology of temporomandibular disorders*. Seattle, IASP Press.

Carlton, S. and R. Coggeshall (2001). "Peripheral capsaicin receptors increase in the inflamed rat hindpaw: a possible mechanism for peripheral sensitization." *Neuroscience* 310: 53-6.

Caterina, M., M. Schumacher, et al. (1997). "The capsaicin receptor: a heat activated ion channel in the pain pathway." *Nature* 389: 816-24.

Chakravarti, P., M. K. Henry, et al. (2005). "Prolactin and heregulin override DNA damage-induced growth arrest and promote phosphatidylinositol-3 kinase-dependent proliferation in breast cancer cells." *Int J Oncol* 26(2): 509-14.

Cheng, Y., I. Zhizhin, et al. (2000). "Prolactin-induced cell proliferation in PC12 cells depends on JNK but not ERK activation." *J Biol Chem* 275(30): 23326-32.

Chiu, T. T., W. Y. Ku, et al. (2002). "A study on the prevalence of and risk factors for neck pain among university academic staff in Hong Kong." *Journal of Occupational Rehabilitation* 12(2): 77-91.

Christian, H. C. and J. F. Morris (2002). "Rapid actions of 17beta-oestradiol on a subset of lactotrophs in the rat pituitary." *J Physiol* 539(Pt 2): 557-66.

Chuang, H., E. Prescott, et al. (2001). "Bradykinin and nerve growth factor release the capsaicin receptor from PtdIns(4,5)P2-mediated inibition." *Nature* 411: 957-62.

Ciereszko, R., M. Opalka, et al. (2003). "Prolactin signalling in porcine theca cells: the involvement of protein kinases and phosphatases." *Reprod Fertil Dev* 15(1-2): 27-35.

Ciereszko, R., M. Opalka, et al. (2001). "Luteotrophic action of prolactin during the early luteal phase in pigs: the involvement of protein kinases and phosphatases." *Reprod Biol* 1(2): 62-83.

Corbacho, A. M., G. Martinez De La Escalera, et al. (2002). "Roles of prolactin and related members of the prolactin/growth hormone/placental lactogen family in angiogenesis." *J Endocrinol* 173(2): 219-38.

Coss, D., C. B. Kuo, et al. (1999). "Dissociation of Janus kinase 2 and signal transducer and activator of transcription 5 activation after treatment of Nb2 cells with a molecular mimic of phosphorylated prolactin." *Endocrinology* 140(11): 5087-94.

Davis, J., J. Gray, et al. (2000). "Vanilloid receptor 1 is essential for inflammatory thermal hyperalgesia." *Nature* 405: 183-7.

Devor, M., R. Amir, et al. (2002). "Pathophysiology of trigeminal neuralgia: the ignition hypothesis." *Clin J Pain* 18: 4-13.

D'Isanto, M., M. Vitiello, et al. (2004). "Prolactin modulates IL-8 production induced by porins or LPS through different signaling mechanisms." *Immunobiology* 209(7): 523-33.

Dogusan, Z., R. Hooghe, et al. (2001). "Cytokine-like effects of prolactin in human mononuclear and polymorphonuclear leukocytes." *J Neuroimmunol* 120(1-2): 58-66.

Dominguez-Caceres, M. A., J. M. Garcia-Martinez, et al. (2004). "Prolactin induces c-Myc expression and cell survival through activation of Src/Akt pathway in lymphoid cells." *Oncogene* 23(44): 7378-90.

Dorn, G., S. Patel, et al. (2004). "siRNA relieves chronic neuropathic pain." *Nucleic Acids Res* 32: e49.

Ducret, T., S. Boudina, et al. (2002). "Effects of prolactin on intracellular calcium concentration and cell proliferation in human glioma cells." *Glia* 38(3): 200-14.

Ducret, T., A. M. Vacher, et al. (2004). "Effects of prolactin on ionic membrane conductances in the human malignant astrocytoma cell line U87-MG." *J Neurophysiol* 91(3): 1203-16.

Dussor, G. O., G. Helesic, et al. (2004). "Cholinergic modulation of nociceptive responses in vivo and neuropeptide release in vitro at the level of the primary sensory neuron." *Pain* 107(1-2): 22-32.

Feig, S. and P. Lipton (1993). "Pairing the cholinergic agonist carbachol with patterned Schaffer collateral stimulation initiates protein synthesis in hippocampal CA1 pyramidal cell dendrites via a muscarinic, NMDA-dependent mechanism." *J Neurosci* 13(1010-21).

Flores, C. M., R. M. DeCamp, et al. (1996). "Neuronal nicotinic receptor expression in sensory neurons of the rat trigeminal ganglion: demonstration of alpha3beta4, a novel subtype in the mammalian nervous system." *J Neurosci* 16(24): 7892-901.

Flores, C. M., A. S. Leong, et al. (2001). "Capsaicin-evoked CGRP release from rat buccal mucosa: development of a model system for studying trigeminal mechanisms of neurogenic inflammation." *Eur J Neurosci* 14(7): 1113-20.

Franklin, R. B., J. Zou, et al. (2000). "Protein kinase C alpha, epsilon and AP-1 mediate prolactin regulation of mitochondrial aspartate aminotransferase expression in the rat lateral prostate." *Mol Cell Endocrinol* 170(1-2): 153-61.

Frasor, J., U. Barkai, et al. (2001). "PRL-induced ERalpha gene expression is mediated by Janus kinase 2 (Jak2) while signal transducer and activator of transcription 5b (Stat5b) phosphorylation involves Jak2 and a second tyrosine kinase." *Mol Endocrinol* 15(11): 1941-52.

Freeman, M. E., B. Kanyicska, et al. (2000). "Prolactin: structure, function, and regulation of secretion." *Physiol Rev* 80(4): 1523-631.

Fresno Vara, J. A., M. A. Caceres, et al. (2001). "Src family kinases are required for prolactin induction of cell proliferation." *Mol Biol Cell* 12(7): 2171-83.

Fristad, I. (1997). "Dental innervation: functions and plasticity after peripheral injury." *Acta Odonto Scand* 55: 236-54.

Fujimoto, N., K. Igarashi, et al. (2004). "Identification of estrogen-responsive genes in the GH3 cell line by cDNA microarray analysis." *J Steroid Biochem Mol Biol* 91(3): 121-9.

Gamse, R. and A. Saria (1985). "Potentiation of tachykinin-induced plasma protein extravasation by CGRP." *Eur J Pharmacol* 114: 61-66.

Garry, M., J. Durnett Richardson, et al. (1994). "Sodium Nitroprusside Evokes the Release of Immunoreactive Calcitonin Gene-Related Peptide and Substance P from Dorsal Horn Slices via Nitric Oxide-Dependent and Nitric Oxide-Independent Mechanisms." *J. Neuroscience* 14: 4329-4337.

Gazelius, B., B. Edwall, et al. (1987). "Vasodilatory effects and coexistence of CGRP and substance P in sensory nerves of cat dental pulp." *Acta Physiol Scand* 130: 33-40.

Gear, R., C. Miaskowski, et al. (1996). "Kappa-opioids produce significantly greater analgesia in women than in men." *Nature Med* 2(11): 1248-50.

Gerr, F., M. Marcus, et al. (2002). "A prospective study of computer users: I. Study design and incidence of musculoskeletal symptoms and disorders." *American Journal of Industrial Medicine* 41(4): 221-35.

Gibbs, J., C. M. Flores, et al. (2004). "Neuropeptide Y inhibits capsaicin-sensitive nociceptors via a Y1-receptor-mediated mechanism." *Neuroscience* 125(3): 703-9.

Goffin, V., S. Bernichtein, et al. (2003). "Development of new prolactin analogs acting as pure prolactin receptor antagonists." *Pituitary* 6(2): 89-95.

Goodis, H. E., W. R. Bowles, et al. (2000). "Prostaglandin E2 enhances bradykinin-evoked iCGRP release in bovine dental pulp." *J Dent Res* 79(8): 1604-7.

Gordon, S., J. Brahim, et al. (1999). "Quantifying analgesic onset in the oral surgery model." *Clin Pharm Therap* 29: 100.

Goupille, O., J. V. Barnier, et al. (2000). "Effect of PRL on MAPK activation: negative regulatory role of the C-terminal part of the PRL receptor." *Mol Cell Endocrinol* 159(1-2): 133-46.

Gubbay, O., H. O. Critchley, et al. (2002). "Prolactin induces ERK phosphorylation in epithelial and CD56(+) natural killer cells of the human endometrium." *J Clin Endocrinol Metab* 87(5): 2329-35.

Gutzman, J. H., D. E. Rugowski, et al. (2004). "Multiple kinase cascades mediate prolactin signals to activating protein-1 in breast cancer cells." *Mol Endocrinol* 18(12): 3064-75.

Hargreaves, K., W. Bowles, et al. (1992). "An In vitro Method to Evaluate Regulation of Neuropeptide Release." *J. Endo* 18: 597-600.

Heden, P., J. Jernbeck, et al. (1989). "Increased skin flap survival and arterial dilation by calcitonin gene-related peptide." *Scand J Plast Reconstr Surg* 23: 11-16.

Ho, T. W., M. Kawaminami, et al. (1993). "Secretion of phosphorylated and non-phosphorylated rat prolactin isoforms at different stages of the estrous cycle during rat pregnancy and pseudo-pregnancy." *Endocrine J* 1: 435-9.

Hovey, R. C., J. F. Trott, et al. (2001). "Transcriptional and spatiotemporal regulation of prolactin receptor mRNA and cooperativity with progesterone receptor function during ductal branch growth in the mammary gland." *Dev Dyn* 222(2): 192-205.

Huang, G. J., L. LeResche, et al. (2002). "Risk factors for diagnostic subgroups of painful temporomandibular disorders (TMD)." *Journal of Dental Research* 81(4): 284-8.

Igwe, O. (2003). "c-Src kinase activation regulates preprotachykinin gene expression and substance P secretion in rat sensory ganglia." *Eur J Neurosci* 18: 1719-30.

Ikeda, Y., A. Ueno, et al. (2001). "Invovlement of vanilloid receptor type I and prostanoids in the acid-induced writhing repsones of mice." *Life Sci* 69: 2911-9.

Jackson, D. L. and K. M. Hargreaves (1999). "Activation of excitatory amino acid receptors in bovine dental pulp evokes the release of iCGRP." *J Dent Res* 78(1): 54-60.

Ji, J., M. Wernli, et al. (2003). "Enhanced gene silencing by the application of multiple specific small interfering RNAs." *FEBS Letters* 552: 247-52.

Jin, X., N. Morsy, et al. (2004). "Modulation of TRPV1 by nonreceptor tyrosine kinase, c-Src kinase." *Am J Physiol—Cell Physiol* 287: C558-63.

Johansson, A., L. Unell, et al. (2003). "Gender difference in symptoms related to temporomandibular disorders in a population of 50-year-old subjects." *Journal of Orofacial Pain* 17(1): 29-35.

Kalkam, C., K. Visser, et al. (2003). "Preoperative prediction of severe postoperative pain." *Pain* 105: 415-423.

Kamei, J., K. Zushida, et al. (2001). "Role of vanilloid receptor type I in thermal allodynia and hyperalgesia in diabetic mice." *Eur J Pharmacol* 422: 83-6.

Kapur, N., I. Kamel, et al. (2003). "ral and craniofacial pain: diagnosis, pathophysiology, and treatment." *Int Anesth Clin* 41: 115-150.

Karadottir, H., L. Lenoir, et al. (2002). "Pain experienced by patients during periodontal maintenance treatment." *Journal of Periodontology* 73(5): 536-42.

Katusic, S., C. M. Beard, et al. (1990). "Incidence and clinical features of trigeminal neuralgia, Rochester, Minn., 1945-1984. " *Annals of Neurology* 27(1): 89-95.

Kelly, M., A. Lagrange, et al. (1999). "Rapid effects of estrogen to modulate G protein-coupled receptors via activation of protein kinase A and protein kinase C pathways." *Steroids* 64: 64-75.

Kerezoudis, N., L. Olgart, et al. (1994). "Involvement of substance P but not nitric oxide or calcitonin gene-related peptide in neurogenic plasma extravasation in rat incisor pulp and lip." *Arch Oral Biol* 39: 769-74.

Khouzam, H. (2000). "Chronic pain and its management in primary care." *South Med J* 93: 946-951.

Kilo, S., C. Harding-Rose, et al. (1997). "Peripheral CGRP release as a marker for neurogenic inflammation: a model system for the study of neuropeptide secretion in rat paw skin." *Pain* 73(2): 201-7.

Kinoshita, H., T. Yasui, et al. (2001). "Expression of ovarian prolactin receptor in relation to hormonal changes during induction of ovulation in the rat." *Gynecol Obstet Invest* 52(2): 132-8.

Kitt, C. A., K. Gruber, et al. (2000). "Trigeminal neuralgia: opportunities for research and treatment." *Pain* 85(1-2): 3-7.

Kjartansson, J. and C. Dalsgaard (1987). "Calcitonin gene-related peptide increases survival of a musculocutaneous critical flap in the rat." *Eur J Pharmacol* 142: 355-8.

Kostova, V. and M. Koleva (2001). "Back disorders (low back pain, cervicobrachial and lumbosacral radicular syndromes) and some related risk factors." *Journal of the Neurological Sciences* 192(1-2): 17-25.

Leondires, M. P., Z. Z. Hu, et al. (2002). "Estradiol stimulates expression of two human prolactin receptor isoforms with alternative exons-1 in T47D breast cancer cells." *J Steroid Biochem Mol Biol* 82(2-3): 263-8.

LeResche, L., K. Saunders, et al. (1997). "Use of exogenous hormones and risk of temporomandibular disorder pain." *Pain* 69(1-2): 153-60.

Lipton, J., J. Ship, et al. (1993). "Estimated prevalence and distribution of reported orofacial pain in the United States." *J Am Dent Assoc* 124: 115-121.

Livak, K. and T. Schmittgen (2001). "Analysis of relative gene expression data using real-time quantitative PCR and the 2(-Delta Delta C(T)) Method." *Methods* 25: 402-8.

Ma, F. Y., D. R. Grattan, et al. (2005). "Prolactin-regulated tyrosine hydroxylase activity and messenger ribonucleic acid expression in mediobasal hypothalamic cultures: the differential role of specific protein kinases." *Endocrinology* 146(1): 93-102.

Marfurt, C., L. Ellis, et al. (1993). "Sensory and sympathetic nerve sprouting in rat cornea following neonatal administration of capsaicin." *Somatosens Mot Res* 10: 377-98.

Martin, P. (1986). *Headaches*. Sydney Australia.

Martin, V., S. Wernke, et al. (2003): "Medical oophorectomy with and without estrogen add-back therapy in the prevention of migraine headache." *Headache* 43(4): 309-21.

McCleane, G. (1999). "Topical application of doxepin hydrochloride, capsaicin and a combination of both produces analgesia in chronic human neuropathic pain: a randomized double-blind placebo-controlled study." *Br J Clin Pharmacol* 49: 574-9.

Morenilla-Palao, C., R. Planells-Cases, et al. (2004). "Regulated exocytosis contributes to protein kinase C potentiation of vanilloid receptor activity." *J Biol Chem* 279: 25665-72.

Motta, M., P. Accornero, et al. (2004). "Leptin and prolactin modulate the expression of SOCS-1 in association with interleukin-6 and tumor necrosis factor-alpha in mammary cells: a role in differentiated secretory epithelium." *Regul Pept* 121(1-3): 163-70.

Nagafuchi, H., N. Suzuki, et al. (1999). "Prolactin locally produced by synovium infiltrating T lymphocytes induces excessive synovial cell functions in patients with rheumatoid arthritis." *J Rheumatol* 26(9): 1890-900.

Naylor, M. J., J. A. Lockefeer, et al. (2003). "Prolactin regulates mammary epithelial cell proliferation via autocrine/paracrine mechanism." *Endocrine* 20(1-2): 111-4.

Neubert, J., Y. Matsuka, et al. (2002). "Microdialysis in trigeminal ganglia." *Brain Res Protoc* 10: 102-8.

Norfleet, A. M., C. H. Clarke, et al. (2000). "Antibodies to the estrogen receptor-alpha modulate rapid prolactin release from rat pituitary tumor cells through plasma membrane estrogen receptors." *Faseb J* 14(1): 157-65.

Nowak, R. A., S. Mora, et al. (1999). "Prolactin is an autocrine or paracrine growth factor for human myometrial and leiomyoma cells." *Gynecol Obstet Invest* 48(2): 127-32.

Numazaki et al., "Structural determinant of TRPV1 desensitization interacts with calmodulin." Proc. Natl. Acad. Sci. USA. 2003 Jun 24;100(13):8002-6.

Numazaki, M., T. Tominaga, et al. (2002). "Direct phosphorylation of capsaicin receptor VR1 by protein kinase Cepsilon and identification of two target serine residues." *J Biol Chem* 277: 13375-8.

Oetting, W. and A. Walker (1986). "Differential isoform distribution between stored and secreted prolactin." *Endocrinology* 119: 1377-81.

Ogueta, S., J. Munoz, et al. (2002). "Prolactin is a component of the human synovial liquid and modulates the growth and chondrogenic differentiation of bone marrow-derived mesenchymal stem cells." *Mol Cell Endocrinol* 190(1-2): 51-63.

Oomizu, S., N. Boyadjieva, et al. (2003). "Ethanol and estradiol modulate alternative splicing of dopamine D2 receptor messenger RNA and abolish the inhibitory action of bromocriptine on prolactin release from the pituitary gland." *Alcohol Clin Exp Res* 27(6): 975-80.

Ossipov, M., D. Bian, et al. (1999). "Lack of involvement of capsaicin sensitive neurons in nerve-ligation induced tactile allodynia in rats." *Pain* 79: 127-33.

Pi, X. and J. L. Voogt (2002). "Sex difference and estrous cycle: expression of prolactin receptor mRNA in rat brain." *Brain Res Mol Brain Res* 103(1-2): 130-9.

Pi, X., B. Zhang, et al. (2003). "Promoter usage and estrogen regulation of prolactin receptor gene in the brain of the female rat." *Neuroendocrinology* 77(3): 187-97.

Pi, X. J. and D. R. Grattan (1998). "Differential expression of the two forms of prolactin receptor mRNA within microdissected hypothalamic nuclei of the rat." *Brain Res Mol Brain Res* 59(1): 1-12.

Picazo, R. A., J. P. Garcia Ruiz, et al. (2004). "Cellular localization and changes in expression of prolactin receptor isoforms in sheep ovary throughout the estrous cycle." *Reproduction* 128(5): 545-53.

Price, T., A. Patwardhan, et al. (2004). "Cannabinoid receptor-independent actions of the aminoalkylindole cannabinoid WIN 55,212-2 on trigeminal sensory neurons." *Br J Pharmac* 142: 257-66.

Price, T., A. Patwardhan, et al. (2004). "Modulation of trigeminal sensory neuron activity by the dual cannabinoid-vanilloid agonists anandamide, N-arachidonoyl-dopamine and arachidonyl-2-chloroethylamide." *Br J Pharm* 141: 1118-1130.

Price, T. J., G. Helesic, et al. (2003). "The neuronal distribution of cannabinoid receptor type 1 in the trigeminal ganglion of the rat." *Neuroscience* 120(1): 155-62.

Royster, M., P. Driscoll, et al. (1995). "The prolactin receptor in the fetal rat: cellular localization of mRNA, immunoreactive protein and ligand binding activity and induction of expressin in late gestation." *Endocrinology* 136: 3892-3900.

Schroeder, M. D., J. L. Brockman, et al. (2003). "Inhibition of prolactin (PRL)-induced proliferative signals in breast cancer cells by a molecular mimic of phosphorylated PRL, S179D-PRL." *Endocrinology* 144(12): 5300-7.

Schuler, L. A., J. C. Lu, et al. (2001). "Prolactin receptor heterogeneity: processing and signalling of the long and short isoforms during development." *Biochem Soc Trans* 29(Pt 2): 52-6.

Secondo, A., R. Sirabella, et al. (2003). "Involvement of PI3'-K, mitogen-activated protein kinase and protein kinase B in the up-regulation of the expression of nNOS-alpha and nNOSbeta splicing variants induced by PRL-receptor activation in GH3 cells." *J Neurochem* 84(6): 1367-77.

Skinner, D. C. and A. Caraty (2003). "Prolactin release during the estradiol-induced LH surge in ewes: modulation by progesterone but no evidence for prolactin-releasing peptide involvement." *J Endocrinol* 177(3): 453-60.

Sorin, B., A. M. Vacher, et al. (2000). "Role of protein kinases in the prolactin-induced intracellular calcium rise in Chinese hamster ovary cells expressing the prolactin receptor." *J Neuroendocrinol* 12(9): 910-8.

Southall, M. and M. Vasko (2001). "Prostaglandin receptor subtypes, EP3C and EP4, mediate the prostaglandin E2-induced cAMP production and sensitization of sensory neurons." *J Biol Chem* 276: 16083-91.

Staud, R., M. E. Robinson, et al. (2003). "Diffuse noxious inhibitory controls (DNIC) attenuate temporal summation of second pain in normal males but not in normal females or fibromyalgia patients." *Pain* 101(1-2): 167-74.

Straub, R., J. Georgi, et al. (2002). "In polymyalgia rheumatica serum prolactin is positively correlated with the number of typical symptoms but not with typical inflammatory markers." *Rheumatology* 41: 423-9.

Sweitzer, S., S. Wong, et al. (2004). "Protein kinase C epsilon and gamma: involvement in formalin-induced nociception in neonatal rats." *J Pharm Exp Therap* 309: 616-25.

Szawka, R. E. and J. A. Anselmo-Franci (2004). "A secondary surge of prolactin on the estrus afternoon." *Life Sci* 75(8): 911-22.

Takahashi, H., Nabeshima, Y., Nabeshima, Y., Ogata, K. and Takeuchi, S. "Molecular cloning and nucleotide sequence of DNA complementary tohuman decidual prolactin mRNA" *J Biochem.* 95 (5), 1491-1499 (1984)

Tanaka, M., Y. Hayashida, et al. (2002). "Identification of a novel first exon of prolactin receptor gene expressed in the rat brain." *Endocrinology* 143(6): 2080-4.

Torner, L., N. Toschi, et al. (2002). "Increased hypothalamic expression of prolactin in lactation: involvement in behavioural and neuroendocrine stress responses." *Eur J Neurosci* 15(8): 1381-9.

Torner, L., N. Toschi, et al. (2001). "Anxiolytic and anti-stress effects of brain prolactin: improved efficacy of antisense targeting of the prolactin receptor by molecular modeling." *J Neurosci* 21(9): 3207-14.

Tuchsen, F., H. Hannerz, et al. (2003). "Risk factors predicting hip pain in a 5-year prospective cohort study." *Scandinavian Journal of Work, Environment & Health* 29(1): 35-9.

Tusher, V., Tibshirani R, et al. (2001). "Significance analysis of microarrays applied to the ionizing radiation response." *Proc Natl Acad Sci USA* 98: 5116-21.

Ulrich, Y., C. Flores, et al. (2001). "Capsaicin-evoked release of immunoreactive caclitonin gene-related peptide from rat trigeminal ganglia: evidence for intraganglionic neurotransmission." *Pain* 91: 219-26.

Ulrich-Lai, Y. M., C. M. Flores, et al. (2001). "Capsaicin-evoked release of immunoreactive calcitonin gene-related peptide from rat trigeminal ganglion: evidence for intraganglionic neurotransmission." *Pain* 91(3): 219-26.

Urtishak, S. L., E. A. McKenna, et al. (2001). "Prolactin and prolactin receptor expression in rat, small intestine, intraepithelial lymphocytes during neonatal development." *Dev Immunol* 8(3-4): 319-30.

Van Coppenolle, F. R. Skryma, et al. (2004). "Prolactin stimulates cell proliferation through a long form of prolactin receptor and K+ channel activation." *Biochem J* 377(Pt 3): 569-78.

Walker, A. M. (2001). "Unmodified and phosphorylated prolactin and gamma delta T cell development and function." *Lupus* 10(10): 735-41.

Wallaschofski, H., A. Kobsar, et al. (2003). "Prolactin receptor signaling during platelet activation." *Horm Metab Res* 35(4): 228-35.

Warren, M. P. and J. L. Fried (2001). "Temporomandibular disorders and hormones in women." *Cells Tissues Organs* 169(3): 187-92.

Watson, C. S., A. M. Norfleet, et al. (1999). "Rapid actions of estrogens in GH3/B6 pituitary tumor cells via a plasma membrane version of estrogen receptor-alpha." *Steroids* 64(1-2): 5-13.

Watters, J. J., T. Y. Chun, et al. (2000). "Estrogen modulation of prolactin gene expression requires an intact mitogen-activated protein kinase signal transduction pathway in cultured rat pituitary cells." *Mol Endocrinol* 14(11): 1872-81.

Welch, K. (2001). *Headache*. Philadelphia, Lippincott, Williams and Wilkins.

Wicks, J. R. and C. L. Brooks (1995). "Biological activity of phosphorylated and dephosphorylated bovine prolactin." *Mol Cell Endocrinol* 112: 223-9.

Wu, W., D. Coss, et al. (2003). "Different biological effects of unmodified prolactin and a molecular mimic of phosphorylated prolactin involve different signaling pathways." *Biochemistry* 42(24): 7561-70.

Xu, X., W. Wu, et al. (2003). "Opposite effects of unmodified prolactin and a molecular mimic of phosphorylated prolactin on morphology and the expression of prostate specific genes in the normal rat prostate." *Prostate* 54(1): 25-33.

Yamamoto, I., M. Wakita, et al. (2003). "Tissue distribution of prolactin receptor mRNA during late stage embryogenesis of the chick." *Poult Sci* 82(1): 155-7.

Yamauchi, T., N. Yamauchi, et al. (2000). "Constitutive tyrosine phosphorylation of ErbB-2 via Jak2 by autocrine secretion of prolactin in human breast cancer." *J Biol Chem* 275(43): 33937-44.

Yunus, M. B. (2002). "Gender differences in fibromyalgia and other related syndromes." *Journal of Gender Specific Medicine* 5(2): 42-7.

Zakrzewska, J. (2002). "Facial pain: neurological and non-neurological." *J Neurol Neurosurg Psych* 72(Suppl 2): ii27-ii32.

Zakrzewska, J. (2002). "Trigeminal neuralgia." *Clinical Evidence* 7: 1221-31.

Zakrzewska, J. M. (1996). "Women as dental patients: are there any gender differences?." *International Dental Journal* 46(6): 548-57.

Zhang, J., H. Li, et al. (2002). "Acute topical application of tumor necrosis factor alpha evokes protein kinase A-dependent responses in rat sensory neurons." *J Neurophysiol* 88: 1387-92.

Zhuang, Z.-Y., H. S. Xu, et al. (2004). "Phosphatidylinositol 3-kinase activates ERK in primary sensory neurons and mediates inflammatory heat hyperalgesia throught TRPV1 sensitization." *J Neurosci* 24: 8300-09.

What is claimed is:

1. A method for inhibiting, reducing and/or treating pain in a subject comprising administering to a subject in need thereof an effective amount of a pharmaceutically acceptable formulation comprising a prolactin antagonist, wherein the prolactin antagonist at least partially inhibits the biological activity of prolactin receptors.

2. The method of claim 1, wherein the prolactin antagonist is a polypeptide which comprises a prolactin molecule, or a variant thereof.

3. The method of claim 2, wherein the prolactin molecule comprises at least one mutation.

4. The method of claim 1, wherein the antagonist is G120K-GH or G120R-PL.

5. The method of claim 1, wherein the formulation is administered parenterally.

6. The method of claim 1, wherein the formulation is administered by injection.

7. The method of claim 1, wherein the formulation is administered by tissue injection.

8. The method of claim 1, wherein the formulation is administered intravenously.

9. The method of claim 3, wherein is the prolactin molecule is G129-PRL, S179D-PRL, or Δ1-9-G129R-PRL.

10. The method of claim 1, wherein the subject is an estrogen-sensitized female subject.

* * * * *